(12) United States Patent
Augelli-Szafran et al.

(10) Patent No.: US 6,972,287 B1
(45) Date of Patent: Dec. 6, 2005

US006972287B1

(54) METHOD OF INHIBITING AMYLOID PROTEIN AGGREGATION AND IMAGING AMYLOID DEPOSITS

(75) Inventors: Corinne Elizabeth Augelli-Szafran, Ann Arbor, MI (US); Mark Robert Barvian, Ann Arbor, MI (US); Christopher Franklin Bigge, Ann Arbor, MI (US); Shelly Ann Glase, Ann Arbor, MI (US); Shunichiro Hachiya, Ibaraki (JP); John Steven Kiely, San Diego, CA (US); Takenori Kimura, Ibaraki (JP); Yingjie Lai, Edison, NJ (US); Annette Theresa Sakkab, Northville, MI (US); Mark James Suto, La Jolla, CA (US); Larry Craswell Walker, Ann Arbor, MI (US); Tomoyuki Yasunaga, Ibaraki (JP); Nian Zhuang, Ypsilanti, MI (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/009,611

(22) PCT Filed: May 31, 2000

(86) PCT No.: PCT/US00/15071

§ 371 (c)(1),
(2), (4) Date: May 20, 2002

(87) PCT Pub. No.: WO00/76489

PCT Pub. Date: Dec. 21, 2000

Related U.S. Application Data
(60) Provisional application No. 60/138,550, filed on Jun. 10, 1999.

(51) Int. Cl.[7] .................... C07D 401/10; C07D 403/10; C07D 413/10; A61K 31/41; A61P 25/28
(52) U.S. Cl. ................. 514/227.5; 514/658; 514/237.8; 514/255.02; 514/307; 514/331; 514/281; 514/396; 514/406; 514/427; 564/435; 564/457; 548/254; 548/340.1; 548/335.5; 548/566; 548/375.1; 544/59; 544/162; 544/399; 544/402; 546/147; 546/229
(58) Field of Search ................................ 564/435, 457; 548/254, 340.1, 335.5, 566, 375.1; 544/59, 162, 399, 402; 546/147, 229; 514/658, 227.5, 237.8, 255.02, 307, 331, 381, 396, 406, 427

(56) References Cited

U.S. PATENT DOCUMENTS
5,739,169 A * 4/1998 Ocain et al. ................. 514/658

FOREIGN PATENT DOCUMENTS
| EP | 0459136 | 12/1991 |
|----|---------|---------|
| WO | 0076969 | 12/2000 |

OTHER PUBLICATIONS

Bowman et al. {Journal of the Chemical Society, Perkin Transactions 1: Organic and Bioorganic Chemistry (1972–1999) (1973), (1), 1–4}.*
PCT International Search Report, PCT/US00/15071.
Höppener et al., "The Role of Islet Amyloid Polypeptide (IAPP)/Amylin in the Pathogenesis of Type 2 diabetes Mellitus: Implications From a Transgenic Mouse Study", *European Journal of Endocrinology*, vol. 130, No. Suppl. 2, 1994, p. 63.
Höppener et al., "Extensive islet amyloid formation is induced by development of Type II diabetes mellitus and contributes to its progression: pathogenesis of diabetes in a mouse model", *Diabetologia*, vol. 42, No. 4, 1999, pp. 427–434.
Cooper et al., "Purification and characterization of a peptide from amyloid–rich pancreases of type 2 diabetic patients", *Proc. Natl. Acad. Sci. USA*, vol. 84, No. 23, 1997, pp. 8628–8632.
Cleaveland et al., "Site of Action of Two Novel Pyrimidine Biosynthesis Inhibitors Accurately Predicted by the Compare Program", *Biochemical Pharmacology*, vol. 49, No. 7, 1995, pp. 947–954.
Sturm et al., "Elektrochemische Oxidation von Acridanen", *Chem. Ber.*, vol. 111, No. 1, 1978, pp. 227–239.

* cited by examiner

*Primary Examiner*—Mark Berch
*Assistant Examiner*—Kahsay Habte
(74) *Attorney, Agent, or Firm*—Peter C. Richardson; Lorraine B. Ling; James A. Jubinsky

(57) ABSTRACT

The present invention provides a method of treating Alzheimer's disease using a compound of Formula (I). Also provided is a method of inhibiting the aggregation of amyloid proteins using a compound of the Formula (I) and a method of imaging amyloid deposits, as well as new compounds of Formula (I).

28 Claims, No Drawings

METHOD OF INHIBITING AMYLOID PROTEIN AGGREGATION AND IMAGING AMYLOID DEPOSITS

REFERENCE TO RELATED APPLICATIONS

This is a national stage application, under 35 U.S.C. §371, of International Application No. PCT/US 00/15071, filed May 31, 2000, which claims the benefit of U.S. provisional patent application, Serial No. 60/138,550, filed Jun. 10, 1999.

FIELD OF THE INVENTION

This invention relates to a method of inhibiting amyloid protein aggregation and imaging amyloid deposits. More particularly, this invention relates to a method of inhibiting amyloid protein aggregation in order to treat Alzheimer's disease.

BACKGROUND OF THE INVENTION

Amyloidosis is a condition characterized by the accumulation of various insoluble, fibrillar proteins in the tissues of a patient. The fibrillar proteins that comprise the accumulations or deposits are called amyloid proteins. While the particular proteins or peptides found in the deposits vary, the presence of fibrillar morphology and a large amount of β-sheet secondary suture is common to many types of amyloids. An amyloid deposit is formed by the aggregation of amyloid proteins, followed by the further combination of aggregates and/or amyloid proteins.

The presence of amyloid deposits has been shown in various diseases, each with its particular associated protein, such as Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Alzheimer's disease, Down's syndrome, Scrapie, Creutzfeldt-Jacob disease, Kuru, Gerstmann-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, Sickle Cell Anemia, Parkinson's Disease, and Islets of Langerhans diabetes Type II insulinoma.

Alzheimer's disease is a degenerative brain disorder characterized clinically by progressive loss of memory, cognition, reasoning, judgement, and emotional stability that gradually leads to mental deterioration and ultimately death. Because Alzheimer's disease and related degenerative brain disorders are a major medical issue for an increasingly aging population, the need for new treatments and methods for diagnosing the disorders are needed.

A simple, noninvasive method for detecting and quantitating amyloid deposits in a patient has been eagerly sought. Presently, detection of amyloid deposits involves histological analysis of biopsy or autopsy materials. Both methods have major drawbacks. For example, an autopsy can only be used for a postmortem diagnosis.

The direct imaging of amyloid deposits in vivo is difficult, as the deposits have many of the same physical properties (i.e., density and water content) as normal tissues. Attempts to image amyloid deposits directly using magnetic resonance imaging (MRI) and computer-assisted tomography (CAT) have been disappointing and have detected amyloid deposits only under certain favorable conditions. In addition, efforts to label amyloid deposits with antibodies, serum amyloid P protein, or other probe molecules has provided some selectivity on the periphery of tissues, but has provided for poor imaging of tissue interiors.

Thus, it would be useful to have a noninvasive technique for imaging and quantitating amyloid deposits in a patient. In addition, it would be useful to have compounds that inhibit the aggregation of amyloid proteins to form amyloid deposits.

SUMMARY OF THE INVENTION

The present invention provides a method of treating Alzheimer's disease, the method comprising administering to a patient having Alzheimer's disease a therapeutically effective amount of a compound of Formula I

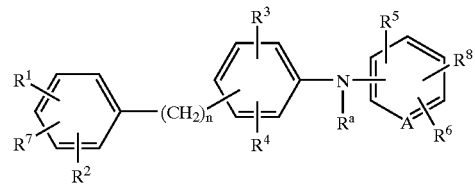

wherein

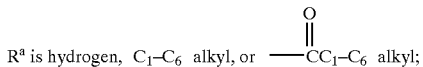

alkyl;

n is 0 to 5 inclusive;

$R^1$, $R^2$, $R^3$, $R^4$, $R^5$, $R^6$, and $R^7$ are independently hydrogen, halogen, —OH, —NH$_2$, NR$^b$R$^c$, —CO$_2$H, —CO$_2$C$_1$-C$_6$ alkyl, —NO$_2$, —OC$_{1-C12}$ alkyl, —C$_1$-C$_8$ alkyl, —CF$_3$, —CN, —OCH$_2$ phenyl, —OCH$_2$-substituted phenyl, —(CH$_2$)$_m$-phenyl, —O-phenyl, —O-substituted phenyl,

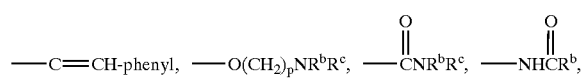

—NH(CH$_2$)$_p$NR$^b$R$^c$, —N(C$_1$-C$_6$alkyl)(CH$_2$)$_p$NR$^b$R$^c$,

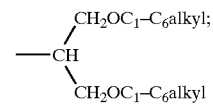

$R^8$ is COOH, tetrazolyl, —SO$_2$R$^d$, or —CONHSO$_2$R$^d$;

$R^b$ and $R^c$ are independently hydrogen, —C$_1$-C$_6$ alkyl, —(CH$_2$)$_m$-phenyl, or R$^b$ and R$^c$ taken together with the nitrogen atom to which they are attached form a cyclic ring selected from piperidinyl, pyrrolyl, imidazolyl, piperazinyl, 4-C$_1$-C$_6$ alkylpiperazinyl, morpholino, thiomorpholino, decahydroisoquinoline, or pyrazolyl;

$R^d$ is hydrogen, —C$_1$-C$_6$ alkyl, —CF$_3$, or phenyl;

m is 0 to 5 inclusive;

p is 1 to 5 inclusive;

A is CH or N;

$R^1$ and $R^2$, when adjacent to one another, can be methylene-dioxy;

or the pharmaceutically acceptable salts thereof.

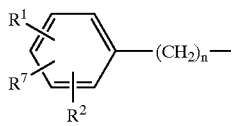

the 4-position of the phenyl ring.

In a preferred embodiment of the method, in the compounds of Formula I $R^a$ is hydrogen;

n is 2; and $R^3$ and $R^4$ are hydrogen.

In a preferred embodiment of the method, in the compounds of Formula I $R^a$ is hydrogen;

$R^1$ is halo;

$R^2$ is hydrogen or halo;

$R^3$, $R^4$, $R^5$, and $R^6$ are hydrogen; and n is 2 to 5 inclusive.

In another preferred embodiment of the method, in the compounds of Formula I $R^a$ is hydrogen;

n is 2 or 3;

$R_1$ is $-NR^bR^c$; and $R^2$, $R^3$, $R^4$, $R^5$, and $R^7$ all are hydrogen.

In a preferred embodiment of the method, in the compounds of Formula I $R^a$ is hydrogen;

n is 2;

$R^3$ and $R^4$ are hydrogen; and $R^1$, $R^2$, and $R^7$ are independently chlorine, —N(CH$_2$CH$_3$)$_2$, —OH, CH$_3$—, fluorine, —CF$_3$, phenyl, hydrogen, —OCH$_2$ phenyl, —O(CH$_2$)$_3$N(CH$_3$)$_2$, —O phenyl, —O(CH$_2$)$_7$CH$_3$, —CH(CH$_2$OCH$_2$CH$_3$)$_2$, pyrrolyl, —CH═CH-phenyl,

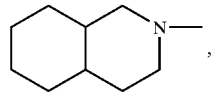

—OCH$_2$-substituted phenyl, pyrrozolyl, or —N(phenyl)$_2$.

In a preferred embodiment of the method, in the compounds of Formula I $R^a$ is hydrogen;

n is 3, 4, or 5;

$R^3$ and $R^4$ are hydrogen; and $R^1$, $R^2$, and $R^7$ are independently chlorine or hydrogen.

In a preferred embodiment of the method, in the compounds of Formula I $R^a$ is hydrogen;

n is 2;

$R^3$ and $R^4$ are hydrogen; and $R^5$, $R^6$, and $R^8$ are independently hydrogen, —CO$_2$H, —NO$_2$, —OCH$_3$,

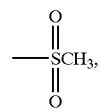

—NH—C$_1$–C$_6$ alkyl, —N(C$_1$–C$_6$alkyl)$_2$, —NH$_2$, or pyrrolyl.

In a preferred embodiment of the method, in the compounds of Formula I $R^a$ is hydrogen;

n is 2;

$R^3$ and $R^4$ are hydrogen; and $R^5$ is —CO$_2$H.

Also preferred is a method of treating Alzheimer's disease, the method comprising administering to a patient having Alzheimer's disease a therapeutically effective amount of a compound of Formula I

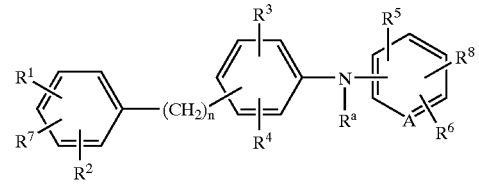

wherein $R^a$ is hydrogen;

n is 1 to 5 inclusive;

$R^3$ and $R^4$ are hydrogen;

$R^1$, $R^7$, and $R^2$ are independently chlorine, —N(CH$_2$CH$_3$)$_2$, —OH, CH$_3$—, fluorine, —CF$_3$, phenyl, hydrogen, —OCH$_2$ phenyl, —O(CH$_2$)$_3$N(CH$_3$)$_2$, —O phenyl, —O(CH$_2$)$_7$CH$_3$, —CH(CH$_2$OCH$_2$CH$_3$)$_2$, pyrrolyl, —CH═CH-phenyl, —N[(CH$_2$)$_3$CH$_3$]$_2$, substituted phenyl, —OCH$_2$-substituted phenyl, pyrazolyl, or —N(phenyl)$_2$;

$R^5$ and $R^6$ are independently hydrogen, —CO$_2$H, —NO$_2$, —OCH$_3$, imidazolyl, —CN, fluorine, —CH$_3$, —CF$_3$, or pyrrolyl;

or the pharmaceutically acceptable salts thereof.

In a preferred embodiment of the method, compounds of Formula I are

2-{4-[2-(3,4-Dichlorophenyl)ethyl]phenylamino}-benzoic acid;

2-{4-[2-(3,4-Dichloro-phenyl)-ethyl]phenylamino}-5-nitrobenzoic acid;

2-{4-[4-(3,4-Dichloro-phenyl)-ethyl]phenylamino}-4-methoxy-5-nitrobenzoic acid;

2-{4-[2-(3,4-Dihydroxy-phenyl)-ethyl]-phenylamino}benzoic acid;

2-{4-[2-(4-Dibutylamino-phenyl)ethyl]phenylamino}benzoic acid;

2-{4-[2-(3,4,5-Trihydroxy-phenyl)ethyl]phenylamino}benzoic acid;

2-{4-[3-(3,4-Dichlorophenyl)propyl]phenylamino}-4-methoxy-5-nitrobenzoic acid;

2-{4-[3-(3,4-Dichlorophenyl)propyl]phenylamino}-4-imidazo-1-yl-5-nitrobenzoic acid;

2-{4-[3-(3,4-Dichlorophenyl)-propyl]phenylamino}benzoic acid;
2-{4-[4-(3,4-Dichlorophenyl)butyl]phenylamino}benzoic acid;
2-{4-[4-(3,4-Dichloro-phenyl)-butyl]-phenylamino}-5-nitro-benzoic acid;
2-{4-[4-(3,4-Dichlorophenyl)-butyl]phenylano}-3,5-dinitrobenzoic acid;
2-{4-[5-(3,4-Dichlorophenyl)pentyl]phenylamino}-5-nitrobenzoic acid;
2-{4-[5-(3,4-Dichloro-phenyl)pentyl]phenylamino}-4-methoxy-5-nitrobenzoic acid;
2-[4-(3,4-Dichloro-benzyl)-phenylamino]-benzoic acid;
2-{4-[2-(3,4-Dimethyl-phenyl)-ethyl]-phenylamino}-5-nitro-benzoic acid;
2-{4-[2-(3,4-Difluoro-phenyl)-ethyl]-phenylamino}-5-nitro-benzoic acid;
2-{4-[2-(4-Chloro-3-trifluoromethyl-phenyl)ethyl]-phenylamino}-benzoic acid;
2-[4-(2-Biphenyl4-yl-ethyl)phenylamino]-5-nitro-benzoic acid;
5-Nitro-2-(4-phenethyl-phenylamino)ibenzoic acid;
2-(4-Phenethyl-phenylamino)-benzoic acid;
2-{4-[2-(3,4-Dichloro-phenyl)ethyl]-phenylamino}-5-methoxy-benzoic acid;
2-{4-[2-(3,4-Dichloro-phenyl)ethyl]-phenylamino}-terephthalic acid;
2-{4-[2-(3,4-Dichloro-phenyl)ethyl]-phenylamino}-5-methyl-benzoic acid;
4-{4-[2-(3,4-Dichloro-phenyl)ethyl]-phenylamino}-isophthalic acid;
2-{4-[2-(3,4-Dichloro-phenyl)ethyl]-phenylamino}-5-methanesulfonyl-benzoic acid;
2-{4-[2-(3,4-Dichloro-phenyl)ethyl]-phenylamino}-5-imidazol-1-yl-benzoic acid;
2-{4-[2-(3,4-Dichloro-phenyl)-ethyl]-phenylamino}-6-nitro-benzoic acid;
2-{4-[2-(3,4-Dichloro-phenyl)-ethyl]-phenylamino}-4-nitro-benzoic acid;
2-{4-[2-(3,4-Dichloro-phenyl)ethyl]-phenylamino}-3-nitro-benzoic acid;
5-Cyano-2-{4-[2-(3,4-dichloro-phenyl)-ethyl]-phenylamino}-benzoic acid;
2-{4-[2-(3,4-Dichloro-phenyl)-ethyl]-phenylamino}-4,6-difluoro-benzoic acid;
6-{4-[2-(3,4-Dichloro-phenyl)-ethyl]-phenylamino}-2,3-difluoro-benzoic acid;
2-{4-[2-(3,4-Dichloro-phenyl)-ethyl]-phenylamino}-6-fluoro-benzoic acid;
2-{4-[2-(3,4-Dichloro-phenyl)-ethyl]-phenylanino}-3-fluoro-benzoic acid;
2-{4-[2-(3,4-Dichloro-phenyl)-ethyl]-phenylamino}-3-methyl-benzoic acid;
2-{4-[2-(3,4-Dichloro-phenyl)ethyl]-phenylamino}-4-fluoro-benzoic acid;
2-{4-[2-(3,4-Dichloro-phenyl)ethyl]-phenylamino}-3,5-difluoro-benzoic acid;
2-{4-[2-(3,4-Dichloro-phenyl)ethyl]-phenylamino}-3-trifluoromethyl-benzoic acid;
2-{4-[2-(3,4-Dichloro-phenyl)ethyl]-phenylamino}-6-trifluoromethyl-benzoic acid;
2-{4-[2-(3,4-Dichloro-phenyl)ethyl]-phenylano}-5-trifluoromethyl-benzoic acid;
2-{4-[2-(3,4-Dichloro-phenyl)ethyl]-phenylamino}-5-pyrrol-1-yl-benzoic acid;
2-{4-[2-(4-Benzyloxy-phenyl)ethyl]-phenylamino}-benzoic acid;
2-(4-{2-[4-(3-Dimethylamino-propoxy)phenyl]-ethyl}-phenylamino)-benzoic acid;
2-{4-[2-(4-Diethylamino-phenyl)-ethyl]-phenylamino}-benzoic acid;
2-{4-[2-(4-Phenoxy-phenyl)-ethyl]-phenylamino}-benzoic acid;
2-{4-[2-(4-Octyloxy-phenyl)-ethyl]-phenylamino}-benzoic acid;
2-(4-{2-[4-(2-Ethoxy-1-ethoxymethyl-ethyl)-phenyl]-ethyl}-phenylamino)benzoic acid;
2-{4-[2-(4-Pyrro-1-yl-phenyl)ethyl]-phenylamino}-benzoic acid;
2-{4-[2-(4-Styryl-phenyl)-ethyl]-phenylamino}-benzoic acid;
2-{4-[2-(4-Dibutylamino-phenyl)-ethyl]-phenylamino}-benzoic acid;
2-{4-[2-(4'-Ethyl-biphenyl-4-yl)-ethyl]-phenylamino}-benzoic acid;
2-{4-[2-(4-Octyl-phenyl)-ethyl]-phenylamino}-benzoic acid;
2-(4-{2-[3-(3,5-Dichloro-phenoxy)-phenyl]-ethyl}-phenylamino)-benzoic acid;
2-(4-{2-[4-(2-Chloro-6-fluoro-benzyloxy)-phenyl]-ethyl}-phenylamino)-benzoic acid;
2-{4-[2-(4-Pyrazol-1-yl-phenyl)-ethyl]-phenylamino}-benzoic acid;
2-{4-[2-(4-Diphenylamino-phenyl)-ethyl]-phenylamino}-benzoic acid;
2-(4-{2-[4-(3,4-Dichloro-benzyloxy)-phenyl]-ethyl}-phenylamino)-benzoic acid;
2-{4-[2-(3,4-Dichloro-phenyl)ethyl]-phenylamino}-5-amino-benzoic acid;
2-{4-[2-(3,4-Dichloro-phenyl)-ethyl]-phenylamino}-5-trifluoromethyl-benzoic acid,
2-{4-[2-(3,4-Dichlorophenyl)]phenylamino}-5-nitrobenzoic acid;
2-{4-[2-[(3,4-Dichlorophenyl)propyl]phenylamino}-5-nitrobenzoic acid;
2-{4-[2-(3,4-Dimethyl-phenyl)-ethyl]phenylamino}-5-nitrobenzoic acid;
2-[[4-[2-(4-Chloro-3-trifluoromethylphenyl)ethyl]phenyl]amino-benzoic acid;
2-{4-[3-(4-Diethylaminophenyl)propyl]phenylamino}benzoic acid;
2-{4-[3-(4-Nitrophenyl)propyl]phenylamino}benzoic acid;
2-{4-[3-(3-Nitrophenyl)propyl]phenylamino}benzoic acid;
2-{4-[3-(4-Aminophenyl)propyl]phenylamino}benzoic acid;
2-{4-[3-(3-Aminophenyl)propyl]phenylamino}benzoic acid;
2-{4-[2-(4-Aminophenyl)ethyl]phenylamino}benzoic acid;
2-{4-[2-(4-Dipropylaminophenyl)ethyl]phenylamino}benzoic acid monohydrochloride;

2-{4-[2-(4-Diethylaminophenyl)ethyl]phenylamino}benzoic acid monohydrochloride monohydrate;
2-{4-[3-(3-Dipropylaminophenyl)propyl]phenylamino}benzoic acid;
2-{4-[3-(3-Dimethylaminophenyl)propyl]phenylamino}benzoic acid;
2-{4-[3-(4-Ethylaminophenyl)propyl]phenylamino}benzoic acid;
2-(N-{4-[3-(4-Diethylaminophenyl)propyl]phenyl}-N-ethylamino)benzoic acid;
2-{4-[2-(3-Dibenzylaminophenyl)ethyl]phenylamino}benzoic acid;
2-{4-[3-(3-Diethylaminophenyl)propyl]phenylamino}benzoic acid;
2-{4-[2-(3-Aminophenyl)ethyl]phenylamino}benzoic acid;
2-{4-[3-(4-Dimethylaminophenyl)propyl]phenylamino}benzoic acid;
2-{4-[2-(4-Acetylamiophenyl)ethyl]phenylamino}benzoic acid;
2-{4-[2-(3-Acetylamiophenyl)ethyl]phenylamino}benzoic acid;
2-{4-[2-(3-Dipropylaminophenyl)ethyl]phenylamino}benzoic acid monohydrochloride;
2-{4-[2-(3-Dibutylaminophenyl)ethyl]phenylamino}benzoic acid monohydrochloride;
2-{4-[3-(4-Acetylaminophenyl)propyl]phenylamino}benzoic acid;
2-{4-[3-(3-Acetylaminophenyl)propyl]phenylamino}benzoic acid;
2-{4-[3-(3-Diethylaminophenyl)ethyl]phenylamino}benzoic acid monohydrochloride;
2-{4-[2-(3-Piperidin-1-ylphenyl)ethyl]phenylamino}benzoic acid monohydrochloride;
2-{4-[3-(4-Dipropylaminophenyl)propyl]phenylamino}benzoic acid;
2-{4-[3-(4-Dibutylaminophenyl)propyl]phenylamino}benzoic acid;
2-{4-[3-(3-Dibutylaminophenyl)propyl]phenylanino}benzoic acid;
2-(4-{3-[4-(1H-Pyrrol-1-yl)phenyl]propyl}phenylamino)benzoic acid;
2-{4-[3-(4-Piperidin-1-ylphenyl)propyl]phenylamino}benzoic acid;
2-{4-[3-(4-Diethylcarbamoylphenyl)propyl]phenylamino}benzoic acid;
2-{4-[3-(4-Carboxyphenyl)propyl]phenylamino}benzoic acid;
2-{4-[3-(4-Diethylaminomethylphenyl)propyl]phenylamino}benzoic acid;
2-{4-[3-(4-Propylaminophenyl)propyl]phenylamino}benzoic acid;
2-{4-[3-(3-Propylaminophenyl)propyl]phenylamino}benzoic acid;
2-{4-[3-(4-Pyrrolidin-1-yl-phenyl)-propyl]-phenylamino}-benzoic acid;
2-{4-[3-(3-Piperidin-1yl-phenyl)-propyl]-phenylamino}-benzoic acid;
2-{4-[3-(4-[2-Diethylaminoethylamino]phenyl)-propyl]-phenylamino}-benzoic acid;
2-{4-[2-(4-[Hydroxycarbonylmethylamino]phenyl)ethyl]phenylamino}-benzoic acid;
2-{4-[2-(4-[2-Diethylaminoethylamino]phenyl)ethyl]phenylamino}-benzoic acid;
2-{4-[3-(4Morpholinophenyl)propyl]phenylamino}-benzoic acid;
2-{4-[3-(4-Piperzinylphenyl)propyl]phenylamino}-benzoic acid; and
2-[4-(3,4-Dichlorophenyl)phenylamino]benzoic acid.

The invention also provides the foregoing compounds wherein the benzoic acid portion is replaced with a pyridyl carboxylic acid, for example, 4-[4-(3,4-dichlorophenyl)phenylamino]-3-hydroxycarbonylpyridine.

Also provided is a method of inhibiting the aggregation of amyloid proteins to form amyloid deposits, the method comprising administering to a patient in need of inhibition of the aggregation of amyloid protein an amyloid protein aggregation inhibiting amount of a compound of Formula I

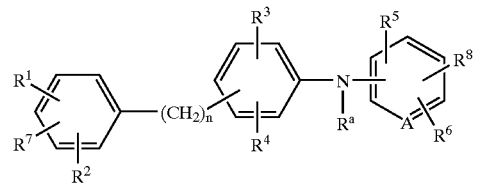

wherein

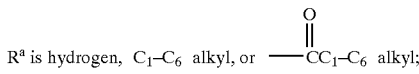

$R^a$ is hydrogen, $C_1$–$C_6$ alkyl, or —CC$_1$–C$_6$ alkyl;

n is 0 to 5 inclusive;
$R^1$, $R^2$, $R^3$, $R^4$, $R^5$, $R^6$, and $R^7$ are independently hydrogen, halogen, —OH, —NH$_2$, NR$^b$R$^c$, —CO$_2$H, —CO$_2$C$_1$–C$_6$ alkyl, —NO$_2$, —OC$_1$–C$_{12}$ alkyl, —C$_1$–C$_8$ alkyl, —CF$_3$, —CN, —OCH$_2$ phenyl, —OCH$_2$-substituted phenyl, —(CH$_2$)$_m$-phenyl, —O-phenyl, —O-substituted phenyl,

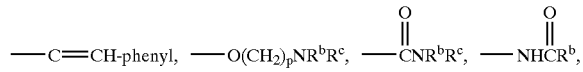

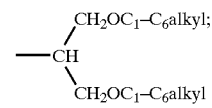

$R^8$ is COOH, tetrazolyl, —SO$_2$R$^d$, or —CONHSO$_2$R$^d$;
$R^b$ and $R^c$ are independently hydrogen, —C$_1$–C$_6$ alkyl, —(CH$_2$)$_m$-phenyl, or $R^b$ and $R^c$ taken together with the nitrogen atom to which they are attached form a cyclic ring selected from piperidinyl, pyrrolyl, imidazolyl, piperazinyl 4-C$_1$–C$_6$ alkylpiperazinyl, morpholino, thiomorpholino, decahydroisoquinoline, or pyrazolyl;
$R^d$ is hydrogen, —C$_1$–C$_6$ alkyl, —CF$_3$, or phenyl;
m is 0 to 5 inclusive;
p is 1 to 5 inclusive;
A is CH or N;
$R^1$ and $R^2$, when adjacent to one another, can be methylene-dioxy;
or the pharmaceutically acceptable salts thereof.

In a preferred embodiment of the method, in the compounds of Formula I $R^a$ is hydrogen;

n is 2; and $R^3$ and $R^4$ are hydrogen.

In a preferred embodiment of the method, in the compounds of Formula I $R^a$ is hydrogen;

$R^3$ and $R^4$ are hydrogen; and n is 2 to 5 inclusive.

In a preferred embodiment of the method, in the compounds of Formula I $R^a$ is hydrogen;

n is 2;

$R^3$ and $R^4$ are hydrogen; and $R^1$, $R^2$, and $R^7$ are independently chlorine, —N(CH$_2$CH$_3$)$_2$, —OH, CH$_3$—, fluorine, —CF$_3$, phenyl, hydrogen, —OCH$_2$ phenyl, —O(CH$_2$)$_3$N(CH$_3$)$_2$, —O phenyl, —O(CH$_2$)$_7$CH$_3$, —CH(CH$_2$OCH$_2$CH$_3$)$_2$, pyrrolyl, —CH=CH-phenyl, —OCH$_2$-substituted phenyl, pyrazolyl, or —N(phenyl)$_2$.

In a preferred embodiment of the method, in the compounds of Formula I $R^a$ is hydrogen;

n is 3, 4, or 5;

$R^3$ and $R^4$ are hydrogen; and $R^1$, $R^2$, and $R^7$ are independently chlorine or hydrogen.

In a preferred embodiment of the method, in the compounds of Formula I $R^a$ is hydrogen;

n is 2;

$R^3$ and $R^4$ are hydrogen; and $R^5$ and $R^6$ are independently hydrogen, —CO$_2$H, —NO$_2$, —OCH$_3$, imidazolyl, —CN, fluorine, —CH$_3$, —CF$_3$, halogen, —NH—C$_1$–C$_6$ alkyl, —N(C$_1$–C$_6$alkyl)$_2$, —NH$_2$, or pyrrolyl.

In a preferred embodiment of the method, in the compounds of Formula I $R^a$ is hydrogen;

n is 2;

$R^3$ and $R^4$ are hydrogen; and $R^5$ is —CO$_2$H.

Also provided is a preferred method of inhibiting the aggregation of amyloid proteins to form amyloid deposits, the method comprising administering to a patient in need of inhibition of the aggregation of amyloid protein an amyloid protein aggregation inhibiting amount of a compound of Formula I wherein $R^a$ is hydrogen;

n is 1 to 5 inclusive;

$R^3$ and $R^4$ are hydrogen;

$R^1$, $R^7$, and $R^2$ are independently chlorine, —N(CH$_2$CH$_3$)$_2$, —OH, CH$_3$—, fluorine, —CF$_3$, phenyl, hydrogen, —OCH$_2$ phenyl, —O(CH$_2$)$_3$N(CH$_3$)$_2$, —O phenyl, —O(CH$_2$)$_7$CH$_3$, —CH(CH$_2$OCH$_2$CH$_3$)$_2$, pyrrolyl, CH=CH-phenyl, —N[(CH$_2$)$_3$CH$_3$]$_2$, substituted phenyl, —OCH$_2$-substituted phenyl, pyrazolyl, or —N(phenyl)$_2$;

$R^5$ and $R^6$ are independently hydrogen, —CO$_2$H, —NO$_2$, —OCH$_3$, imidazolyl, —CN, fluorine, —CH$_3$, —CF$_3$, or pyrrolyl;

$R^8$ is COOH or tetrazolyl;

or the pharmaceutically acceptable salts thereof.

The most preferred compounds provided by the invention have Formula II and pharmaceutically acceptable salts thereof, wherein:

$R^1$ is halo;

$R^2$ is H or halo; and n and $R^6$ are as defined above in Formula I.

Another preferred group of compounds have Formula III and pharmaceutically acceptable salts thereof, wherein:

$R^1$ is halo;

$R^2$ is H or halo; and n and $R^6$ are as defined above in Formula I.

Another group of preferred invention compounds have Formula IV

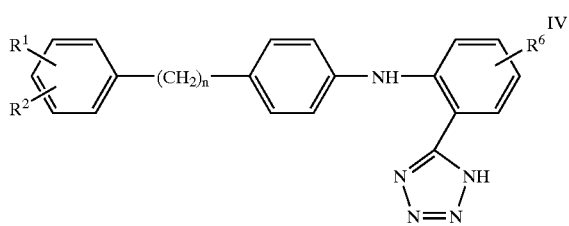

and pharmaceutically acceptable salts thereof, wherein:
R$^1$ is halo;
R$^2$ is H or halo; and
n and R$^6$ are as defined above in Formula I.

In a preferred embodiment of the method, the novel compounds of Formula I are provided which are 2-{4-[2-(3,4-Dichlorophenyl)ethyl]phenylamino}-benzoic acid;
2-{4-[2-(3,4-Dichloro-phenyl)-ethyl]phenylamino}-5-nitrobenzoic acid;
2-{4-[4-(3,4-Dichloro-phenyl)-ethyl]phenylamino}-4-methoxy-5-nitrobenzoic acid;
2-{4-[2-(3,4-Dihydroxy-phenyl)-ethyl]-phenylamino}benzoic acid;
2-{4-[2-(4-Dibutylamino-phenyl)-ethyl]phenylamino}benzoic acid;
2-{4-[2-(3,4,5-Trihydroxy-phenyl)ethyl]phenylamino}benzoic acid;
2-{4-[2-[-(3,4-Dichlorophenyl)propyl]phenylamino}-4-methoxy-5-nitrobenzoic acid;
2-{4-[2-[-(3,4-Dichlorophenyl)propyl]phenylamino}-4-imidazo-1-yl-5-nitrobenzoic acid;
2-{4-[2-[-(3,4-Dichlorophenyl)propyl]phenylamino}benzoic acid;
2-{4-[4-(3,4-Dichlorophenyl)butyl]phenylamino}benzoic acid;
2-{4-[4-(3,4-Dichloro-phenyl)-butyl]-phenylamino}-5-nitro-benzoic acid;
2-{4-[4-(3,4-Dichlorophenyl)-butyl]phenylamino}-3,5-dinitrobenzoic acid;
2-{4-[5-(3,4-Dichlorophenyl)pentyl]phenylamino}-5-nitrobenzoic acid;
2-{4-[5-(3,4-Dichloro-phenyl)pentyl]phenylamino}-4-methoxy-5-nitrobenzoic acid;
2-[4-(3,4-Dichloro-benzyl)-phenylamino]-benzoic acid;
2-{4-[2-(3,4-Dimethyl-phenyl)-ethyl]-phenylamino}-5-nitrobenzoic acid;
2-{4-[2-(3,4-Difluoro-phenyl)-ethyl]-phenylamino}-5-nitro-benzoic acid;
2-{4-[2-(4-Chloro-3-trifluoromethyl-phenyl)-ethyl]-phenylamino}-benzoic acid;
2-[4-(2-Biphenyl-4-yl-ethyl)-phenylamino]-5-nitro-benzoic acid;
5-Nitro-2-(4-phenethyl-phenylamino)-benzoic acid;
2-(4-Phenethyl-phenylamino)-benzoic acid;
2-{4-[2-(3,4-Dichloro-phenyl)-ethyl]-phenylamino}-5-methoxy-benzoic acid;
2-{4-[2-(3,4-Dichloro-phenyl)-ethyl]-phenylamino}-terephthalic acid;
2-{4-[2-(3,4-Dichloro-phenyl)-ethyl]-phenylamino}-5-methyl-benzoic acid;
4-{4-[2-(3,4-Dichloro-phenyl)-ethyl]-phenylamino}-isophthalic acid;
2-{4-[2-(3,4-Dichloro-phenyl)-ethyl]-phenylamino}-5-methanesulfonyl-benzoic acid;
2-{4-[2-(3,4-Dichloro-phenyl)-ethyl]-phenylamino}-5-imidazol-1-yl-benzoic acid;
2-{4-[2-(3,4-Dichloro-phenyl)-ethyl]-phenylamino}-6-nitro-benzoic acid;
2-{4-[2-(3,4-Dichloro-phenyl)-ethyl]-phenylamino}-4-nitro-benzoic acid;
2-{4-[2-(3,4-Dichloro-phenyl)-ethyl]-phenylamino}-3-nitrobenzoic acid;
5-Cyano-2-{4-2-(3,4-chloro-phenyl)-ethyl]-phenylamino}-benzoic acid;
2-{4-[2-(3,4-Dichloro-phenyl)-ethyl]-phenylamino}-4,6-difluoro-benzoic acid;
6-{4-[2-(3,4-Dichloro-phenyl)-ethyl]-phenylamino}-2,3-difluoro-benzoic acid;
2-{4-[2-(3,4-Dichloro-phenyl)-ethyl]-phenylamino}-6-fluoro-benzoic acid;
2-{4-[2-(3,4-Dichloro-phenyl)-ethyl]-phenylamino}-3-fluoro-benzoic acid;
2-{4-[2-(3,4-Dichloro-phenyl)-ethyl]-phenylamino}-3-methyl-benzoic acid;
2-{4-[2-(3,4-Dichloro-phenyl)-ethyl]-phenylamino}-4-fluoro-benzoic acid;
2-{4-[2-(3,4-Dichloro-phenyl)-ethyl]-phenylamino}-3,5-difluoro-benzoic acid;
2-{4-[2-(3,4-Dichloro-phenyl)-ethyl]-phenylamino}-3-trifluoromethyl-benzoic acid;
2-{4-[2-(3,4-Dichloro-phenyl)-ethyl]-phenylamino}-6-trifluoromethyl-benzoic acid;
2-{4-[2-(3,4-Dichloro-phenyl)-ethyl]-phenylamino}-5-trifluoromethyl-benzoic acid;
2-{4-[2-(3,4-Dichloro-phenyl)-ethyl]-phenylamino}-5-pyrrol-1-yl-benzoic acid;
2-{4-[2(4-Benzyloxy-phenyl)-ethyl]-phenylamino}-benzoic acid;
2-(4-{2-[4-(3-Dimethylamino-propoxy)-phenyl]-ethyl}-phenylamino)-benzoic acid;
2-{4-[2-(4-Diethylamino-phenyl)-ethyl]-phenylamino}-benzoic acid;
2-{4-[2-(4-Phenoxy-phenyl)ethyl]-phenylamino}-benzoic acid;
2-{4-[2-(4-Octyloxy-phenyl)-ethyl]-phenylamino}-benzoic acid;
4-{2-[4-(2-Ethoxy-1-ethoxymethyl-ethyl)-phenyl]-ethyl}-phenylamino)-benzoic acid;
2-{4-[2-(4-Pyrrol-1-yl-phenyl)-ethyl]-phenylamino}-benzoic acid;
2-{4-[2-(4-Styryl-phenyl)-ethyl]-phenylamino}-benzoic acid;
2-{4-[2-(4-Dibutylamino-phenyl)-ethyl]-phenylamino}-benzoic acid;
2-{4-[2-(4'-Ethyl-biphenylyl-4-yl)-ethyl]-phenylamino}-benzoic acid;
2-{4-[2-(4-Octyl-phenyl)-ethyl]-phenylamino}-benzoic acid;
2-(4-{2-[3-(3,5-Dichloro-phenoxy)-phenyl]-ethyl}-phenylamino)-benzoic acid;
2-(4-{2-4-(2-Chloro-6-fluoro-benzyloxy)-phenyl]-ethyl}-phenylamino)-benzoic acid;

2-{4-[2-(4-Pyrazol-1-yl-phenyl)-ethyl]-phenylanino}-benzoic acid;
2-{4-[2-(4-Diphenylamino-phenyl)-ethyl]-phenylamino}-benzoic acid;
2-(4-{2-[4-(3,4-Dichloro-benzyloxy)phenyl]-ethyl}-phenylamino)-benzoic acid;
2-{4-[2-[(3,4-Dichlorophenyl)propyl]phenylamino}-5-nitrobenzoic acid;
2-{4-[2-(3,4-Dimethyl-phenyl)-ethyl]phenylamino}-5-nitrobenzoic acid;.
2-[[4-[2-(4-Chloro-3-trifluoromethylphenyl)-ethyl]phenyl]amino-benzoic acid; or
2-[4-(3,4-Dichlorophenyl)phenyl]aminobenzoic acid.

The present invention also provides the compounds:

2-{4-[4-(3,4-Dichloro-phenyl)-ethyl]phenylamino}-4-methoxy-5-nitrobenzoic acid
2-{4-[2-(3,4-Dihydroxy-phenyl)-ethyl]-phenylamino}benzoic acid;
2-{4-[2-(4-Dibutylamino-phenyl)-ethyl]phenylamino}benzoic acid;
2-{4-[2-(3,4,5-Trihydroxy-phenyl)-ethyl]phenylamino}benzoic acid;
2-{4-[2-(3,4-Dichlorophenyl)propyl]phenylamino}-4-methoxy-5-nitrobenzoic acid;
2-{4-[2-[-(3,4-Dichlorophenyl)propyl]phenylamino}-4-imidazo-1-yl-5-nitrobenzoic acid;
2-{4-[4-(3,4-Dichlorophenyl)butyl]phenylamino}benzoic acid;
2-{4-[4-(3,4-Dichloro-phenyl)-butyl]-phenylamino}-5-nitro-benzoic acid;
2-{4-[4-(3,4-Dichlorophenyl)-butyl]phenylamino}-3,5-dinitrobenzoic acid;
2-{4-[5-(3,4-Dichlorophenyl)pentyl]phenylamino}-5-nitrobenzoic acid;
2-{4-[5-(3,4-Dichloro-phenyl)pentyl]phenylamino}-4-methoxy-5-nitrobenzoic acid;
2-[4-(3,4-Dichloro-benzyl)-phenylamino]-benzoic acid;
2-{4-[2-(3,4-Dimethyl-phenyl)-ethyl]-phenylamino}-5-nitro-benzoic acid;
2-{4-[2-(3,4-Difluoro-phenyl)-ethyl]-phenylamino}-5-nitro-benzoic acid;
2-{4-[2-(4-Chloro-3-trifluoromethyl-phenyl)ethyl]-phenylamino}-benzoic acid;
2-[4-(2-Biphenylyl-4-yl-ethyl)-phenylamino]-5-nitro-benzoic acid;
5-Nitro-2-(4-phenethyl-phenylamino)-benzoic acid;
2-{4-[2-(3,4-Dichloro-phenyl)-ethyl]-phenylamino}-5-amino-benzoic acid;
2-{4-[2-(3,4-Dichloro-phenyl)-ethyl]-phenylamino}-5-trifluoromethyl-benzoic acid,
2-{4-[2-(3,4-Dichlorophenyl)]phenylamino}-5-nitrobenzoic acid;
2-(4-Phenethyl-phenylamino)-benzoic acid;
2-{4-[2-(3,4-Dichloro-phenyl)-ethyl]-phenylamino}-5-methoxy-benzoic acid;
2-{4-[2-(3,4-Dichloro-phenyl)-ethyl]-phenylamino}-terephthalic acid;
2-{4-[2-(3,4-Dichloro-phenyl)-ethyl]-phenylamino}-5-methyl-benzoic acid;
4-{4-[2-(3,4-Dichloro-phenyl)-ethyl]-phenylamino}-isophthalic acid;
2-{4-[2-(3,4-Dichloro-phenyl)-ethyl]-phenylamino}-5-methanesulfonyl-benzoic acid;
2-{4-[2-(3,4-Dichloro-phenyl)-ethyl]-phenylamino}-5-imidazol-1-yl-benzoic acid;
2-{4-[2-(3,4-Dichloro-phenyl)-ethyl]-phenylamino}-6-nitro-benzoic acid;
2-{4-[2-(3,4-Dichloro-phenyl)-ethyl]-phenylamino}-4-nitro-benzoic acid;
2-{4-[2-(3,4-Dichloro-phenyl)-ethyl]-phenylamino}-3-nitro-benzoic acid;
5-Cyano-2-{4-[2-(3,4-dichloro-phenyl)-ethyl]-phenylamino}-benzoic acid;
2-{4-[2-(3,4-Dichloro-phenyl)-ethyl]-phenylamino}-4,6-difluoro-benzoic acid;
6-{4-[2-(3,4-Dichloro-phenyl)-ethyl]-phenylamino}-2,3-difluorobenzoic acid;
2-{4-[2-(3,4-Dichloro-phenyl)-ethyl]-phenylamino}-6-fluoro-benzoic acid;
2-{4-[2-(3,4-Dichloro-phenyl)-ethyl]-phenylamino}-3-fluoro-benzoic acid;
2-{4-[2-(3,4-Dichloro-phenyl)-ethyl]-phenylamino}-3-methyl-benzoic acid;
2-{4-[2-(3,4-Dichloro-phenyl)-ethyl]-phenylamino}-4-fluoro-benzoic acid;
2-{4-[2-(3,4-Dichloro-phenyl)-ethyl]-phenylamino}-3,5-difluoro-benzoic acid;
2-{4-[2-(3,4-Dichloro-phenyl)-ethyl]-phenylamino}-3-trifluoromethyl-benzoic acid;
2-{4-[2-(3,4-Dichloro-phenyl)-ethyl]-phenylamino}-6-trifluoromethyl-benzoic acid;
2-{4-[2-(3,4-Dichloro-phenyl)-ethyl]-phenylamino}-5-trifluoromethyl-benzoic acid;
2-{4-[2-(3,4-Dichloro-phenyl)-ethyl]-phenylamino}-5-pyrrol-1-yl-benzoic acid;
2-{4-[2-(4-Benzyloxy-phenyl)-ethyl]-phenylamino}-benzoic acid;
2-(4-{2-[4-(3-Dimethylamino-propoxy)-phenyl]-ethyl}-phenylamino)-benzoic acid;
2-{4-[2-(4-Diethylamino-phenyl)-ethyl]-phenylamino}-benzoic acid;
2-{4-[2-(4-Phenoxy-phenyl)-ethyl]-phenylamino}-benzoic acid;
2-{4-[2-(4-Octyloxy-phenyl)-ethyl]-phenylamino}-benzoic acid;
2-(4-{2-[4-(2-Ethoxy-1-ethoxymethyl-ethyl)-phenyl]-ethyl}-phenylamino)-benzoic acid;
2-{4-[2-(4-Pyrrol-1-yl-phenyl)-ethyl]-phenylamino}-benzoic acid;
2-{4-[2-(4-Styryl-phenyl)-ethyl]-phenylamino}-benzoic acid;
2-{4-[2-(4-Dibutylamino-phenyl)-ethyl]-phenylamino}-benzoic acid;
2-{4-[2-(4'-Ethyl-biphenyl-4-yl)-ethyl]-phenylamino}-benzoic acid;
2-{4-[2-(4-Octyl-phenyl)-ethyl]-phenylamino}-benzoic acid;
2-(4-{2-[3-(3,5-Dichloro-phenoxy)phenyl]-ethyl}-phenylamino)-benzoic acid;
2-(4-{2-[4-Chloro-6-fluoro-benzyloxy)-phenyl]-ethyl}-phenylamino)-benzoic acid;
2-{4-[2-(4-Pyrazol-1-yl-phenyl)-ethyl]-phenylamino}-benzoic acid;

2-{4-[2-(4-Diphenylamino-phenyl)-ethyl]-phenylamino}-benzoic acid;
2-(4-{2-[4-(3,4-Dichloro-benzyloxy)-phenyl]-ethyl}-phenylamino)-benzoic acid;
2-{4-[2-(3,4-Dichloro-phenyl)-ethyl]-phenylamino}-5-amino-benzoic acid;
2-{4-[2-(3,4-Dichloro-phenyl)-ethyl]-phenylamino}-5-trifluoromethyl-benzoic acid;
2-{4-[2-(3,4-Dichlorophenyl)]phenylamino}-5-nitrobenzoic acid;
2-{4-[2-[(3,4-Dichlorophenyl)propyl]phenylamino}-5-nitrobenzoic acid;
2-{4-[2-(3,4-Dimethyl-phenyl)-ethyl]phenylamino}-5-nitrobenzoic acid;
2-{4-[2-(4-Chloro-3-trifluoromethylphenyl)-ethyl]phenylamino}-benzoic acid;
2-{4-[3-(4-Diethylaminophenyl)propyl]phenylamino}benzoic acid;
2-{4-[3-(4-Nitrophenyl)propyl]phenylamino}benzoic acid;
2-{4-[3-(3-Nitrophenyl)propyl]phenylamino}benzoic acid;
2-{4-[3-(4-Aminophenyl)propyl]phenylamino}benzoic acid;
2-{4-[3-(3-Aminophenyl)propyl]phenylamino}benzoic acid;
2-{4-[2-(4-Aminophenyl)ethyl]phenylamino}benzoic acid;
2-{4-[2-(4-Dipropylaminophenyl)ethyl]phenylamino}benzoic acid monohydrochloride;
2-{4-[2-(4-Diethylaminophenyl)ethyl]phenylamino}benzoic acid monohydrochloride monohydrate;
2-{4-[3-(3-Dipropylaminophenyl)propyl]phenylamino}benzoic acid;
2-{4-[3-(3-Dimethylaminophenyl)propyl]phenylamino}benzoic acid;
2-{4-[3-(4-Ethylaminophenyl)propyl]phenylamino}benzoic acid;
2-(N-{4-[3-(4-Diethylaminophenyl)propyl]phenyl}-N-ethylamino)benzoic acid;
2-{4-[2-(3-Dibenzylaminophenyl)ethyl]phenylamino}benzoic acid;
2-{4-[3-(3-Diethylaminophenyl)propyl]phenylamino}benzoic acid;
2-{4-[2-(3-Aminophenyl)-ethyl]phenylamino}benzoic acid;
2-{4-[3-(4-Dimethylaminophenyl)propyl]phenylamino}benzoic acid;
2-{4-[2-(4-Acetylaminophenyl)ethyl]phenylamino}benzoic acid;
2-{4-[2-(3-Acetylaminophenyl)ethyl]phenylanino}benzoic acid;
2-{4-[2-(3-Dipropylaminophenyl)ethyl]phenylamino}benzoic acid monohydrochloride;
2-{4-[2-(3-Dibutylaminophenyl)ethyl]phenylamino}benzoic acid monohydrochloride;
2-{4-[3-(4-Acetylaminophenyl)propyl]phenylamino}benzoic acid;
2-{4-[3-(3-Acetylaminophenyl)propyl]]phenylamino}benzoic acid;
2-{4-[3-(3-Diethylaminophenyl)-ethyl]phenylamino}benzoic acid monohydrochloride;
2-{4-[2-(3-Piperidin-1-ylphenyl)-ethyl]phenylamino}benzoic acid monohydrochloride;
2-{4-[3-(4-Dipropylaminophenyl)propyl]phenylamino}benzoic acid;
2-{4-[3-(4-Dibutylaminophenyl)propyl]phenylamino}benzoic acid;
2-{4-[3-(3-Dibutylaminophenyl)propyl]phenylamino}benzoic acid;
2-(4-{3-[4-(1H-Pyrrol-1-yl)phenyl]propyl}phenylamino)benzoic acid;
2-{4-[3-(4-Piperidin-1-ylphenyl)propyl]phenylamino}benzoic acid;
2-{4-[3-(4-Diethylcarbamoylphenyl)propyl]phenylamino}benzoic acid;
2-{4-[3-(4-Carboxyphenyl)propyl]phenylamino}benzoic acid;
2-{4-[3-(4-Diethylaminomethylphenyl)propyl]phenylamino}benzoic acid;
2-{4-[3-(4-Propylaminophenyl)propyl]phenylamino}benzoic acid;
2-{4-[3-(3-Propylaminophenyl)propyl]phenylamino}benzoic acid;
2-{4-[3-(4-Pyrrolidin-1-yl-phenyl)propyl]-phenylano}-benzoic acid;
2-{4-[3-(3-Piperidin-1-yl-phenyl)propyl]-phenylamino}-benzoic acid;
{5-[(1-Butyl-1,2,3,4-tetrahydro-6-quinolyl)methylidene]-4-oxo-2-thioxothiazolidin-3-yl}acetic acid;
{5-[(1-Butyl-2,3-dihydro-1H-indol-5-yl)methylidene]-4-oxo-2-thioxothiazolidin-3-yl}acetic acid;
3-{5-[(1-Butyl-1,2,3,4-tetrahydroquinolin-6-yl)methylidene]-4-oxo-2-thioxothiazolidin-3-yl}propanoic acid;
4-{5-[(1-Butyl-1,2,3,4-tetrahydroquinolin-6-yl)methylidene-]4-oxo-2-thioxothiazolidin-3-yl}butanoic acid; or 2-[4-(3,4-Dichlorophenyl)phenyl]aminobenzoic acid.

Also provided are the foregoing compounds wherein the terminal phenylalkyl group is attached at the 2- or 3-position of the central phenyl ring, i.e., compounds of the Formula Ia

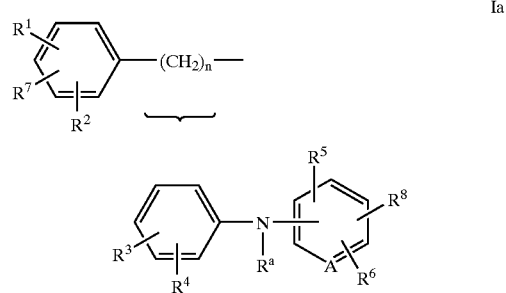

Typical 2- and 3-substituted compounds are:
2-{3-[2-(3,4-Dichlorophenyl)ethyl]phenylamino}-benzoic acid;
2-{2-[2-(3,4-Dichlorophenyl)ethyl]phenylamino}-benzoic acid;
2-{3-[3-(4-Diethylaminophenyl)propyl]phenylamino}-benzoic acid;
2-{3-[3-(4-Di-n-propylaminophenyl)propyl]phenylamino}-benzoic acid;

2-{3-[3-(4-n-Propylaminophenyl)propyl]phenylamino}-benzoic acid;

2-{3-[3-(4-[2-Diethylaminoethylamino]phenyl)propyl]phenylamino}-benzoic acid;

2-{2-[3-(4-[Hydroxycarbonylmethylamino]phenyl)propyl]phenylamino}-benzoic acid;

2-{2-[2-(3-[2-Diethylaminoethylamino]phenyl)-ethyl]phenylamino}-benzoic acid;

2-{3-[3-(4-Morpholinophenyl)propyl]phenylamino}-benzoic acid;

2-{3-[3-(4-Piperazinylphenyl)propyl]phenylamino}-benzoic acid;

2-{3-[2-(4-Chlorophenyl)ethyl]phenylamino}-benzoic acid;

2-{3-[3-(3,4-Dichlorophenyl)propyl]phenylamino}-benzoic acid; and

2-{4-[4-(4-{4-Methylpiperazinyl}phenyl)butyl]phenylamino}-benzoic acid.

Pharmaceutical formulations of the novel compounds admixed with a pharmaceutically acceptable diluent, carrier, or excipient are also provided.

Also provided is a method of imaging amyloid deposits, the method comprising:

a. introducing into a patient a detectable quantity of a labeled compound having the Formula I or a pharmaceutically acceptable salt thereof:

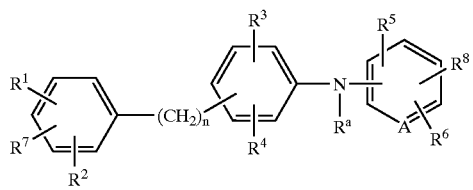

wherein

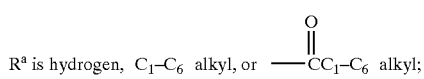

$R^a$ is hydrogen, $C_1$–$C_6$ alkyl, or —$\overset{O}{\overset{\|}{C}}C_1$–$C_6$ alkyl;

n is 0 to 5 inclusive;
$R^1$, $R^2$, $R^3$, $R^4$, $R^5$, $R^6$, and $R^7$ are independently hydrogen, halogen, —OH, —$NH_2$, $NR^bR^c$, —$CO_2H$, —$CO_2C_1$–$C_6$ alkyl, —$NO_2$, —$OC_1$–$C_{12}$ alkyl, —$C_1$–$C_8$ alkyl, —$CF_3$, —CN, —$OCH_2$ phenyl, —$OCH_2$-substituted phenyl, —$(CH_2)_m$-phenyl, —O-phenyl, —O-substituted phenyl,

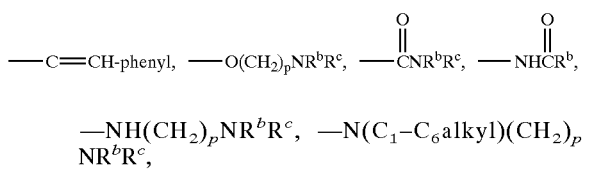
—C≡CH-phenyl, —O(CH$_2$)$_p$NR$^b$R$^c$, —CNR$^b$R$^c$, —NHCR$^b$,

—NH(CH$_2$)$_p$NR$^b$R$^c$, —N(C$_1$–C$_6$alkyl)(CH$_2$)$_p$NR$^b$R$^c$,

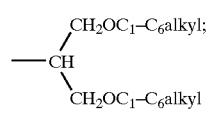

$R^8$ is COOH, tetrazolyl, —$SO_2R^d$, or —$CONHSO_2R^d$;
$R^b$ and $R^c$ are independently hydrogen, —$C_1$–$C_6$ alkyl, —$(CH_2)_m$-phenyl, or $R^b$ and $R^c$ taken together with the nitrogen atom to which they are attached form a cyclic ring selected from piperidinyl, pyrrolyl, imidazolyl, piperazinyl, 4-$C_1$–$C_6$ alkylpiperazinyl, morpholino, thiomorpholino, decahydroisoquinoline, or pyrazolyl;
$R^d$ is hydrogen, —$C_1$–$C_6$ alkyl, —$CF_3$, or phenyl;
m is 0 to 5 inclusive;
p is 1 to 5 inclusive;
A is CH or N;
$R^1$ and $R^2$, when adjacent to one another, can be methylene-dioxy;
or the pharmaceutically acceptable salts thereof;

b. allowing sufficient time for the labeled compound to become associated with amyloid deposits; and c. detecting the labeled compound associated with the amyloid deposits.

In a preferred embodiment of the method, the patient has or is suspected to have Alzheimer's disease.

In a preferred embodiment of the method, the labeled compound is a radio labeled compound.

In a preferred embodiment of the method, the labeled compound is detected using MRI.

The present invention also provides the preferred compounds:

2-{4-[2-(3,4-Dichlorophenyl)ethyl]phenylamino}-benzoic acid;

2-{4-[2-(3,4-Dichloro-phenyl)ethyl]phenylamino}-5-nitrobenzoic acid;

2-{4-[3-(3,4-Dichlorophenyl)propyl]phenylamino}benzoic acid;

2-[[4-[2-(4-Chloro-3-trifluoromethylphenyl)-ethyl]phenyl]amino-benzoic acid;

2-{4-[3-(4-Diethylaminophenyl)propyl]phenylamino}-benzoic acid;

and pharmaceutical formulations thereof.

Pharmaceutically acceptable acid addition salts, amides, and prodrugs of the foregoing compounds are also provided by this invention.

DETAILED DESCRIPTION OF THE INVENTION

The term "alkyl" means a straight or branched chain hydrocarbon having from 1 to 12 carbon atoms. Representative examples of alkyl groups are methyl, ethyl, propyl, isopropyl, isobutyl, butyl, tert-butyl, sec-butyl, pentyl, hexyl, octyl, decyl, and 1,1-dimethyloctyl.

Preferred alkyl groups are $C_1$–$C_8$ alkyl, and especially $C_1$–$C_6$ alkyl.

The term "alkoxy" means an alkyl group attached to an oxygen atom. Representative examples of alkoxy groups include methoxy, ethoxy, tert-butoxy, propoxy, and isobutoxy. Preferred alkoxy groups are $C_1$–$C_{12}$ alkoxy, and especially $C_1$–$C_6$ alkoxy.

The term "halogen" includes chlorine, fluorine, bromine, and iodine.

The term "substituted" means that one or more hydrogen atom in a molecule has been replaced with another atom or group of atoms. For example, substituents include halogen, especially chloro, —OH, —$CF_3$, —$NO_2$, —$NH_2$, —NH($C_1$–$C_6$alkyl), —N($C_1$–$C_6$alkyl)$_2$, $C_1$–$C_6$ alkyl, —$OC_1$–$C_6$ alkyl, —CN, —$CF_3$, —$CO_2H$, and —$CO_2C_1$–$C_6$ alkyl.

The term "substituted phenyl" means a phenyl ring in which from 1 to 4 hydrogen atoms have been independently replaced with a substituent, preferably one selected from the list above. Typical "substituted phenyl" groups include 4-chlorophenyl, 3,4-dibromophenyl, 3-fluoro-4-methylphenyl, 3,4-dichlorophenyl, 3,4-methylenedioxyphenyl, and 4-dimethylaminophenyl.

The symbol "—" means a covalent bond.

Substituent groups represented by $R^1$, $R^3$, and $R^5$, for example, include amino($NR^bR^c$) and acylamino (—$NHCOR^b$). $R^b$ and $R^c$ can be hydrogen, alkyl and phenylalkyl and substituted phenylalkyl, and typical $NR^bR^c$ groups include methylamino, diethylamino, isobutylpropylamino, benzylamino, and 3,4-dimethoxybenzylamino. Examples of acylamino groups include formamido, acetamido, 2-phenylacetamido, and 2-(3-nitrophenyl)acetamido. $R^1$, $R^3$, and $R^5$ can also be aminoalkoxy (—O(CH$_2$)$_p$NR$^b$R$^c$) such as N-methylaminomethoxy and 2-(N-benzylamino)ethoxy, as well as aminoalkylamino (—NH(CH$_2$)$_p$NR$^b$R$^c$) such as 3-(dimethylamino)propylamino and 2-(N-ethyl-N-benzylamino)-ethylamino. Substituent groups such as $R^1$, $R^3$, and $R^5$ additionally can be cyclic structures, for instance when $NR^bR^c$ is part of the substituent group, and $R^b$ and $R^c$ are taken together with the nitrogen to which they are attached to form a cyclic ring selected from imidazole, pyrrole, piperidine, piperazine, 4-$C_1$-$C_6$ alkylpiperazine, morpholine, thiomorpholine, pyrazole, and decahydroisoquinoline.

Substituent groups such as $R^1$, $R^2$, $R^5$, $R^6$, and $R^7$ also can be —CH=CH-phenyl (i.e., styryl), phenoxy, O-substituted phenyl such as 3-iodophenoxy, 2,4,6-trihydroxyphenoxy, 2-fluoro-3-nitrophenoxy, as well as —O-benzyl and —O-substituted benzyl such as 2-trifluoromethylbenzyloxy and 4-aminobenzyloxy.

The term "pharmaceutically acceptable salt, ester, amide, and prodrug" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetraethylammonium, tetraethylammonium, methylamine, dimethylamine, trimethylamine, triethylamine, ethylamine, and the like. (See, for example, Berge S. M., et al., Pharmaceutical Salts, *J. Pharm. Sci.*, 66:1–19 (1977) which is incorporated herein by reference.)

Examples of pharmaceutically acceptable, nontoxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods, for example by reacting a carboxylic acid of Formula I with an alcohol such as ethanol or benzyl alcohol.

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amides and $C_1$–$C_2$ dialkyl secondary amides are preferred. Amides of the compounds of the invention may be prepared according to conventional methods.

The term "prodrug" refers to compounds that are rapidly transformed in vivo to yield the parent compound of the above formulas, for example, by hydrolysis in blood. A thorough discussion is provided in T. Higuchi and V. Stella, *Prodrugs as Novel Delivery Systems*, Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisometric forms by virtue of the presence of asymmetric centers in the compounds. It is contemplated that all stereoisometric forms of the compounds, as well as mixture thereof, including racemic mixtures, form part of this invention.

In the first step of the present method of imaging, a labeled compound of Formula I is introduced into a tissue or a patient in a detectable quantity. The compound is typically part of a pharmaceutical composition and is administered to the tissue or the patient by methods well-known to those skilled in the art.

In the methods of the present invention, a compound can be administered either orally, rectally, parenterally (intravenous, by intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents.

Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar, as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers or propellants as may be required. Ophthalmic formulations, eye ointments, powders, and solutions are also contemplated as being within the scope of this invention.

In a preferred embodiment of the invention, the labeled compound is introduced into a patient in a detectable quantity and after sufficient time has passed for the compound to become associated with amyloid deposits, the labeled compound is detected noninvasively inside the patient. In another embodiment of the invention, a labeled compound of Formula I is introduced into a patient, sufficient time is allowed for the compound to become associated with amyloid deposits, and then a sample of tissue from the patient is removed and the labeled compound in the tissue is detected apart from the patient. In a third embodiment of the invention, a tissue sample is removed from a patient and a labeled compound of Formula I is introduced into the tissue sample. After a sufficient amount of time for the compound to become bound to amyloid deposits, the compound is detected.

The administration of the labeled compound to a patient can be by a general or local administration route. For example, the labeled compound may be administered to the patient such that it is delivered throughout the body. Alternatively, the labeled compound can be administered to a specific organ or tissue of interest. For example, it is desirable to locate and quantitate amyloid deposits in the brain in order to diagnose or track the progress of Alzheimer's disease in a patient.

The term "tissue" means a part of a patient's body. Examples of tissues include the brain, heart, liver, blood vessels, and arteries. A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The term "patient" means humans and other animals. Those skilled in the art are also familiar with determining the amount of time sufficient for a compound to become associated with amyloid deposits. The amount of time necessary can easily be determined by introducing a detectable amount of a labeled compound of Formula I into a patient and then detecting the labeled compound at various times after administration.

The term "associated" means a chemical interaction between the labeled compound and the amyloid deposit. Examples of associations include covalent bonds, ionic bonds, hydrophilic-hydrophilic interactions, hydrophobic-hydrophobic interactions, and complexes.

Those skilled in the art are familiar with the various ways to detect labeled compounds. For example, magnetic resonance imaging (MRI), positron emission tomography (PET), or single photon emission computed tomography (SPECT) can be used to detect radiolabeled compounds. The label that is introduced into the compound will depend on the detection method desired. For example, if PET is selected as a detection method, the compound must possess a positron-emitting atom, such as $^{11}C$ or $^{18}F$.

Another example of a suitable label in a compound of Formula I is an atom such as $^{13}C$, $^{15}N$, or $^{19}F$ which can be detected using magnetic resonance imaging (MRI) which is also sometimes called nuclear magnetic resonance (NMR). In addition, the labeled compounds of Formula I may also be detected by MRI using paramagnetic contrast agents.

Another example of detection is electron paramagnetic resonance (EPR). In this case, EPR probes which are well-known in the art, such as nitroxides, can be used.

The imaging of amyloid deposits can also be carried out quantitatively so that the amount of amyloid deposits can be determined.

The present invention also provides a method of inhibiting the aggregation of amyloid proteins to form amyloid deposits, by administering to a patient in need of inhibition of the aggregation of amyloid protein an amyloid protein inhibiting amount of a compound of Formula I. Those skilled in the art are readily able to determine an amyloid inhibiting amount by simply administering a compound of Formula I to a patient in increasing amounts until the growth of amyloid deposits is decreased or stopped. The rate of growth can be assessed using imaging or by taking a tissue sample from a patient and observing the amyloid deposits therein.

A patient in need of inhibition of the aggregation of amyloid proteins is a patient having a disease or condition in which amyloid proteins aggregate. Examples of such diseases and conditions include Mediterranean fever, Muckle-Wells syndrome, idiopathetic myeloma, amyloid polyneuropathy, amyloid cardiomyopathy, systemic senile amyloidosis, amyloid polyneuropathy, hereditary cerebral hemorrhage with amyloidosis, Alzheimer's disease, Down's syndrome, Scrapie, Creutzfeldt-Jacob disease, Kuru, Gerstmann-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, and Islets of Langerhans diabetes Type II insulinoma.

Also provided by the present invention are compounds of Formula I wherein one or more atom in the compound has been replaced with a radioisotope (a labeled compound). The radioisotope can be any radioisotope. However, $^{3}H$, $^{123}I$, $^{125}I$, $^{131}I$, $^{11}C$, and $^{18}F$ are preferred. Those skilled in the art are familiar with the procedure used to introduce a radioisotope into a compound. For example, a compound of Formula I wherein one carbon atom is $^{11}C$ or $^{14}C$ is readily prepared.

The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient The specific dosage used, however, can vary. For example, the dosage can depend on a number of factors including the requirements of the patient, the severity of the condition being treated, and the pharmacological activity of the compound being used. The determination of optimum dosages for a particular patient is well-known to those skilled in the art.

The examples presented below are intended to illustrate particular embodiments of the invention and are not intended to limit the scope of the specification, including the claims, in any manner.

EXAMPLES

Synthesis

Compounds of Formula I can be prepared by several routes as illustrated in Schemes 6 through 9. Schemes 1 through 5 show synthetic routes that can be used to obtain the desired starting amines (IV), (VIII), (XV), and (XXI).

In Scheme 1, the appropriately substituted aldehyde (I) and a nitrophenylacetic acid (II) yield olefin (III) when heated in piperidine at 150° C. Standard hydrogenation conditions, such as Raney nickel, give desired amine (IV).

Scheme 2 depicts the synthesis of amine (VIII) which contains a three methylene tether. Condensation of aldehyde (I) and nitro-ketone (V) in the presence of sodium hydroxide gives the desired alpha, beta-unsaturated ketone, which upon standard hydrogenation conditions (Raney nickel) gives (VII) and then Wolff-Kishner conditions yields the desired amine (VIII).

Scheme 3 is very similar to Scheme 2, except that the aldehyde (I) is condensed with a substituted aniline (IX).

Scheme 4 illustrates standard Wittig conditions in which the starting materials (XII) and (XIII) are obtained via aldol condensation and ylide chemistry, respectively. Reaction of aldehyde (XII) and bromophosphorane (XIII) in the presence of a base, such as butyl lithium, gives diene (XIV). Standard reduction conditions (e.g., Raney nickel) of (XIV) yields the desired amine (XV).

Scheme 5 illustrates the synthesis of amine (XXI) which contains a 5-methylene tether. Wittig reaction of the bromophosporane (XVII), which is formed from the corresponding substituted bromide (XVI), and nitro aldehyde (XIX), obtained from Swem oxidation of the corresponding alcohol (XVIII), using a base (e.g., LHDMS) yields olefin (XX). Reduction of (XX) using standard conditions (Raney nickel) gives amine (XXI).

Scheme 6 illustrates one route to obtain compounds of Formula I. Either by Buchwald coupling (Method A) followed by saponification or utilizing the Ullman reaction (Method B), compounds of Formula I can be isolated from amines such as (IV), (VIII), and (XV). Compounds of Formula I that contain hydroxy groups, such as Examples 4 and 6, require demethylation of the hydroxy protecting groups with reagents such as boron tribromide in the final step of the synthesis.

Protecting groups will also be used when reactive functional groups such as amino and carboxylic acids are present, so as to avoid unwanted side reactions. Carboxy groups typically are converted to esters (e.g., tert-butyl, benzyl), and amino groups generally are acylated (e.g., acetyl or trimethylsilyl). These and other such protecting groups are well-known to organic chemists, and are fully described by Greene and Wuts in *Protective Groups in Organic Synthesis*, John Wiley and Sons, New York ($2^{nd}$ Ed. 1991). All citations are incorporated herein by reference.

Scheme 7 illustrates the synthesis of compounds of Formula I by reacting amines such as (IV), (VIII), and (XXI) with fluoro-nitro intermediate (XXIV), in the presence of a base (e.g., LHMDS or $Et_3N$) to give ester (XXV). This ester can then be saponified using standard conditions, such as sodium hydroxide.

In Scheme 8, amine (XV) can be coupled with readily available fluoro-substituted carboxylic acids [e.g., (XXVI)

or (XXVII)] in the presence of various bases (such as DBU or triethylamine) to yield compounds of Formula I.

Scheme 9 depicts coupling of amine (VIII) with readily available methyl ester (XXVIII) in the presence of a base, such as imidazole, to give ester (XXIX).

This ester can then be saponified as usual to give compounds of Formula I.

Scheme 10 illustates the synthesis of fluoro-intermediate (XXIV) which is obtained by nitration of readily available methyl ester (XXX) to give (XXVIII). Treatment of (XXVII) with potassium cyanide gives (XXIV).

In Scheme 11, the synthesis of compounds related to Example 18 is illustrated. Reaction of the potassium salts of ortho-substituted benzoic acids (XXVI) with substituted anilines (XXVII) in the presence of potassium carbonate and cupric acetate yields various iodo-substituted aminobenzoic acids (XXVIII). Reaction of (XXVIII) with substituted boronic acids and palladium chloride gives the desired substituted aminobenzoic acids (XXX).

It should, of course, be recognized that several invention compounds of Formula I can be prepared from other compounds defined by Formula I, utilizing standard organic reactions such as oxidation, reduction, alkylation, condensation, elimination, and similar well-known synthetic processes. For example, compounds of Formula I wherein $R^a$ is hydrogen are readily alkylated to form compounds wherein $R^a$ is $C_1$–$C_6$ alkyl. Compounds wherein $R^1$ is $NH_2$ are readily acylated by reaction with an acid halide or acid anhydride to provide compounds wherein $R^1$ is —$NHCOR^b$. Similarly, compounds wherein $R^1$ is $NO_2$ are easily reduced to provide compounds wherein $R^1$ is $NH_2$. The benzoic acids (where $R^8$ is COOH) are readily converted to esters and amides, as well as salts and other prodrugs by routine processes. For example, the benzoic acid can be reacted with oxalylchloride to form the acid chloride, which then readily reacts with a sulfonamide such as methanesulfonamide to produce the corresponding invention compound where $R^8$ is —$CONHSO_2CH_3$.

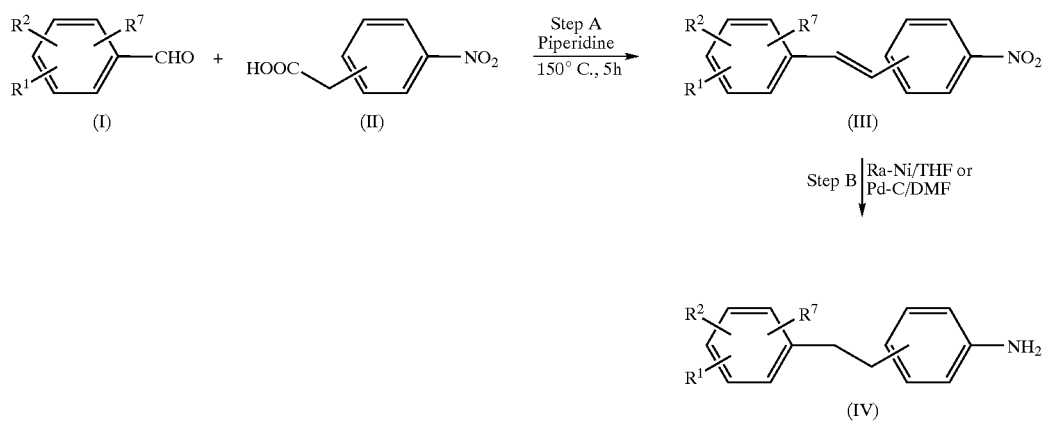

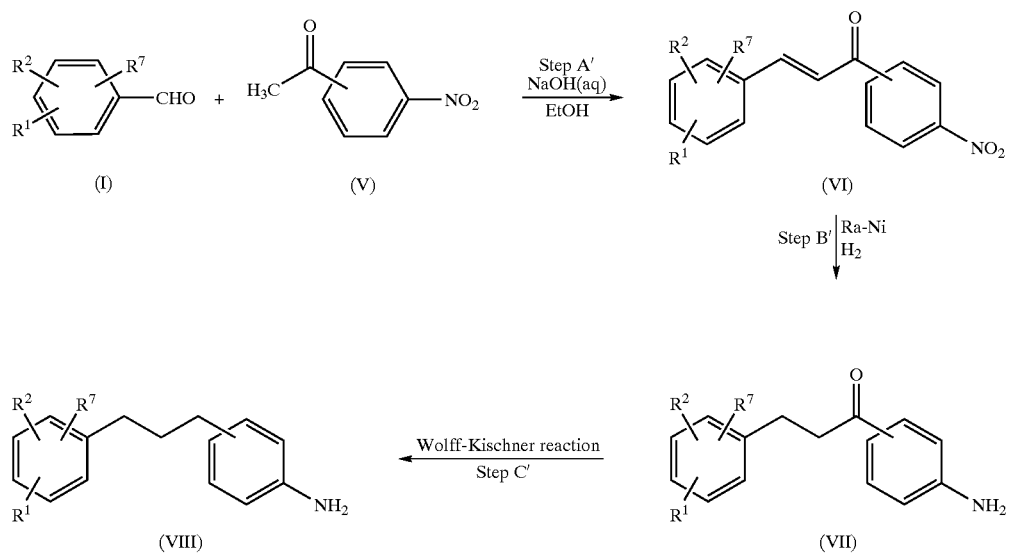

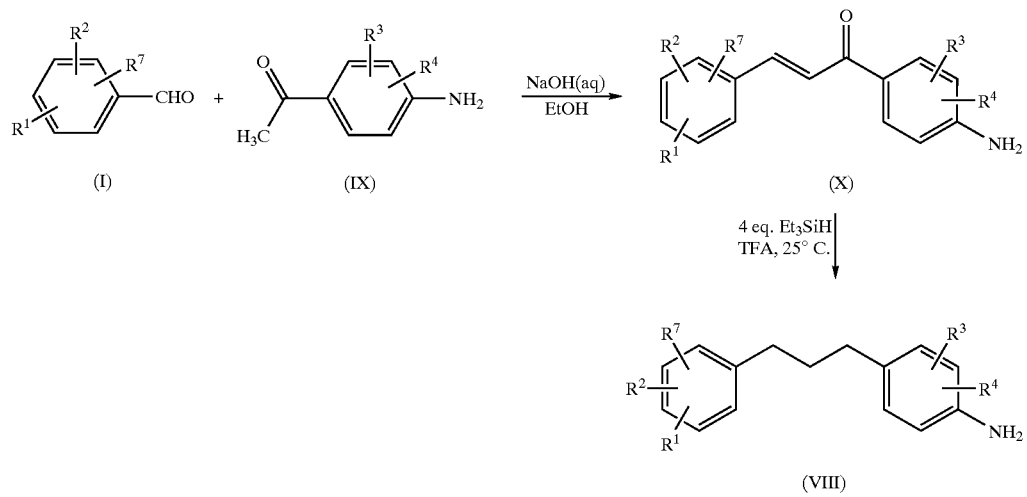
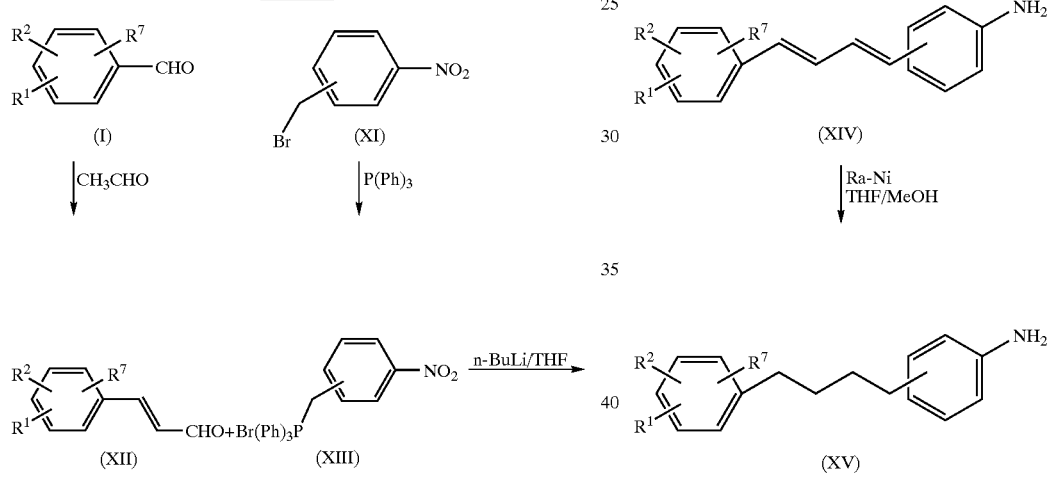
Scheme 5
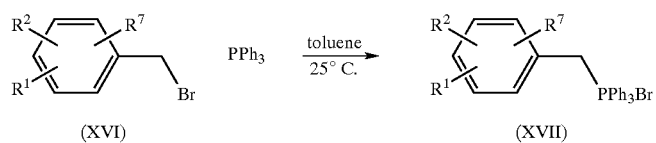
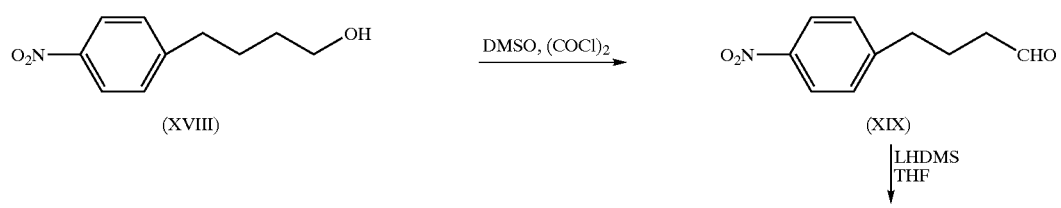

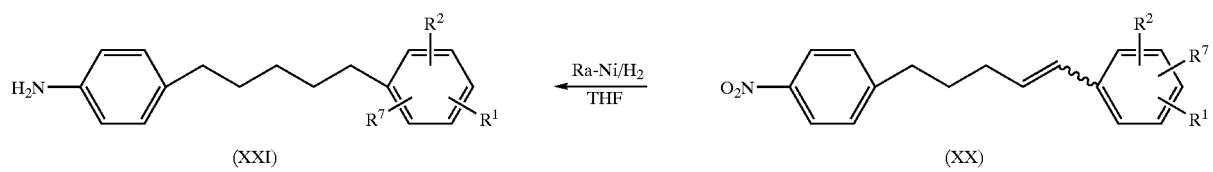
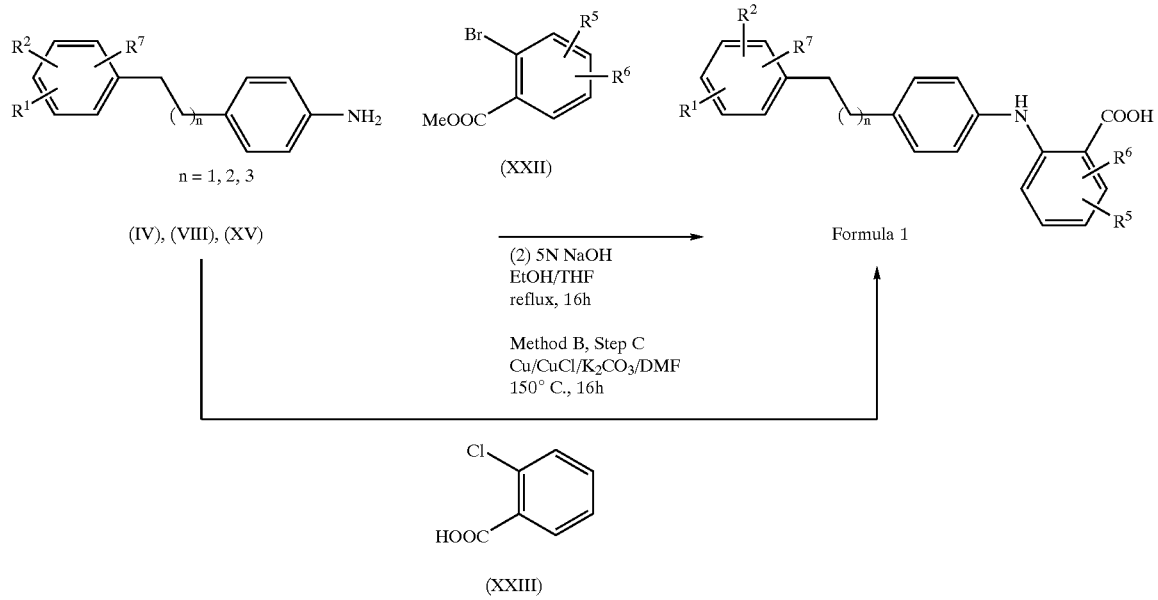
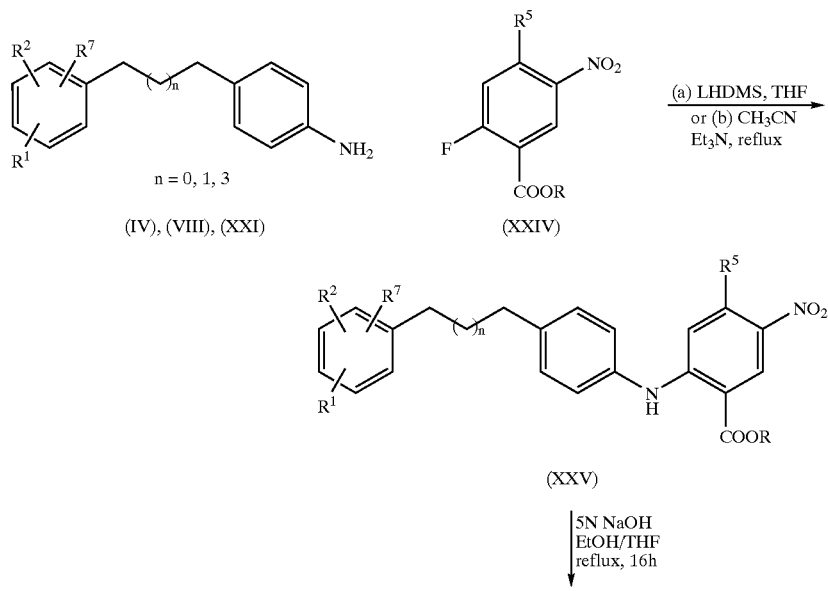

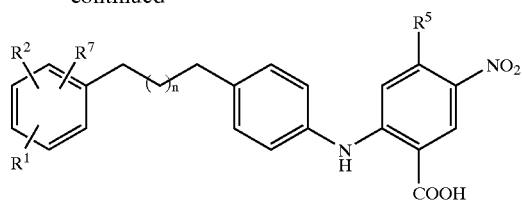
(Compound of Formula I)
Scheme 8
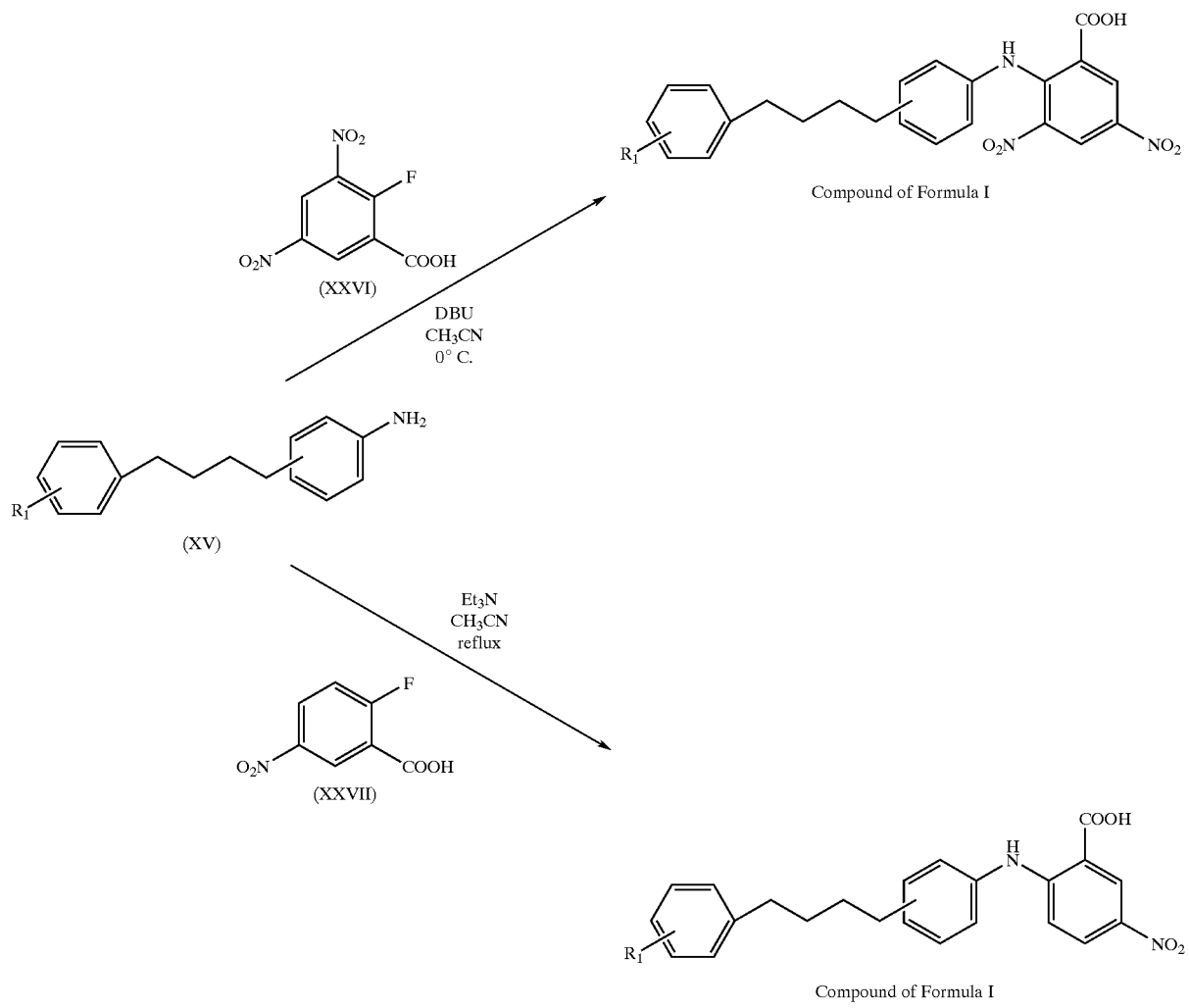
Scheme 9
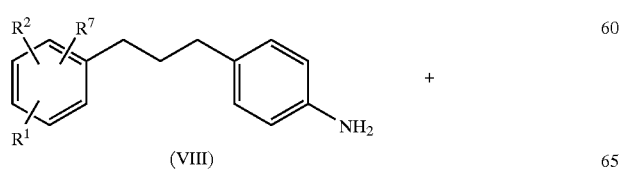
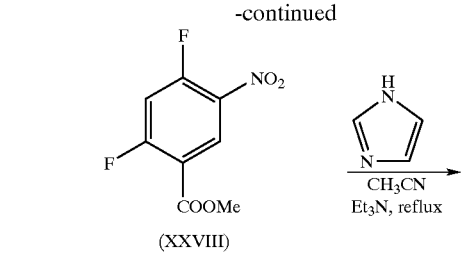

33
-continued

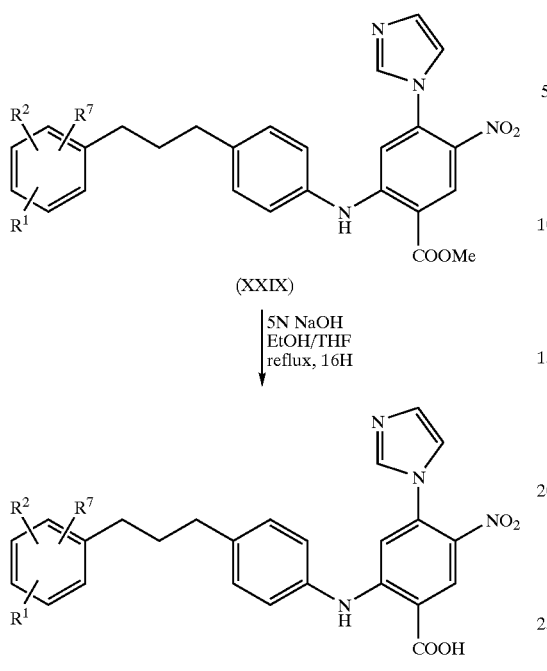

Compound of Formula I

Scheme 10

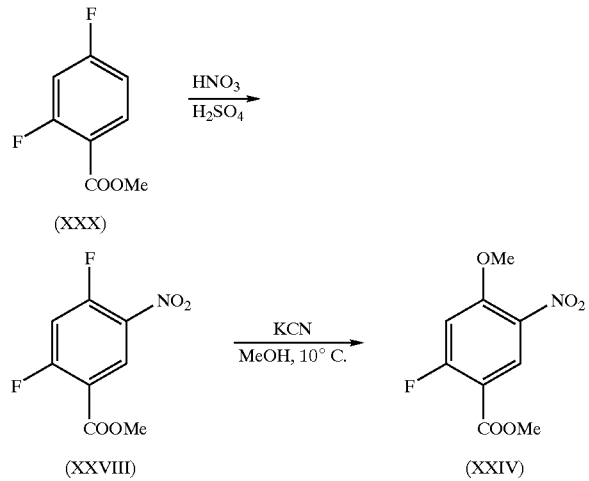

Scheme 11

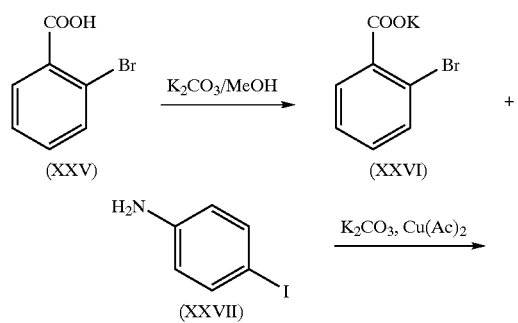

34
-continued

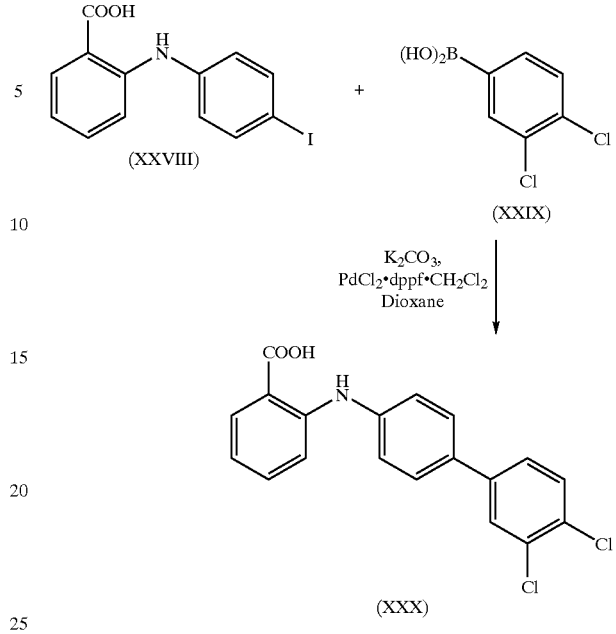

Example 1

Preparation of 2-{4-[2-(3,4-Dichlorophenyl)ethyl] phenylamino}-benzoic acid

Step A (Scheme 1): Preparation of 1,2-Dichloro-4-[2-(4-nitrophenyl)ethenyl]-benzene A mixture of p-nitrophenylacetic acid (51.23 g, 0.28 mol) and 3,4-dichlorobenzaldehyde (49.50 g, 0.28 mol) in piperidine (50 mL) was heated to 150–160° C. for 5 hours under a $N_2$ atmosphere. After cooling the reaction mixture, the precipitate was triturated in boiling methanol (MeOH) (50 mL) and then cooled to –5° C. for 12 hours. The crystalline precipitate was filtered off, rinsed with cold MeOH and dried at room temperature in a vacuum oven overnight to yield an orange solid, 22.71 g (0.077 mol, 27%) of the desired product.

mp 190–191° C. MS:294.9 ($M^+$).

Step B (Scheme 1): Preparation of 4-[2-(3,4-Dichlorophenyl)ethyl]benzenamine

A sample of 1,2-dichloro-4-[2-(4nitrophenyl)ethenyl]benzene (98.0 g, 0.33 mol) in tetrahydrofuran (THF) (1.6 L) was reduced in the presence of Raney Nickel (Ra—Ni) (20 g) at 25° C. to 40° C. ($\Delta P=13.5$ psi) under a hydrogen atmosphere. The reaction mixture was filtered, and the filtrate was concentrated in vacuo to give an orange solid, 85.0 g (0.32 mol, 95.8%) of the desired product.

mp 68–70° C. MS: 266.1 ($M^+$).

Step C (Scheme 6): Preparation of 2-{4-[2-(3,4-Dichlorophenyl)ethyl]phenylamino}-benzoic acid Method A A mixture of 4-[2-(3,4-dichlorophenyl)-ethyl] benzenamine (28.37 g, 106.59 mmol), methyl 2-bromobenzoate (19.10 g, 88.82 mmol), cesium carbonate (40.52 g, 124.35 mmol), tris(dibenzylideneacetone-dipaladium(0) (2.44 g, 2.67 mmol) and (S)-(2,2'-bis(di-p-tolylphosphino-1,1'-binaphthyl (98%, (S)-tol-BINAP) (2.71 g, 4.00 mmol) (Ligand/Pd=1.5) in anhydrous toluene (300 mL) was heated to 100° C. for 34 hours under $N_2$. After cooling to room temperature, the reaction mixture was diluted with ether, filtered through celite and rinsed thoroughly with ether. The filtrate was evaporated to dryness to give a brown residue (68 g). The resulted residue was dissolved in ethanol (EtOH) (50 mL) and THF (100 mL), and then 5N NaOH (aq.) (200 mL) was added, and the mixture was refluxed for 16 hours. The solvent was removed in vacuum. The residue was acidified with concentrated HCl to pH 3. The resulting precipitate was collected by filtration, triturated with boiling MeOH—$H_2O$ (4:1) and dried in a vacuum at room temperature for 16 hours to give Example 1, an orange solid (31.95 g, 0.083 mol, 77.6%). mp 175.0–177.0° C.

Analysis for $C_{21}H_{17}N_1O_2Cl_2$: Calcd: C, 65.30; H, 4.44; N, 3.63. Found: C, 65.40; H, 4.54; N, 3.50.

Method B

A mixture of 2-chlorobenzoic acid (5.4 g, 0.034 mol), 4-[2-(3,4-dichlorophenyl)-ethyl]benzenamine (10.0 g, 0.037 mol), anhydrous potassium carbonate (16.9 g, 0.12 mol), copper powder (4.94 g, 0.077 mol), and copper(I) chloride (0.37 g, 0.0037 mol) in dry dimethylformamide (DMF) (85 mL) was heated to reflux for 24 hours at 150° C. The reaction mixture was poured into hot $H_2O$ (150 mL) and heated to 90° C. on a hot plate. Charcoal was added, and this mixture was stirred at 90° C. for 5 minutes. The warm brown mixture was filtered through filter paper. The cooled filtrate was then acidified with concentrated HCl (pH 1), and the precipitate was collected by filtration, triturated with boiling MeOH—$H_2O$ (1:2) and dried under vacuum at room temperature for 16 hours to give Example 1, an orange solid (2.3 g, 0.006 mol, 17.5%). mp 165.0–173.0° C.

Analysis for $C_{21}H_{17}N_1O_2Cl_2$: Calcd: C, 65.30; H, 4.44; N, 3.63. Found: C, 65.68; H, 4.58; N, 3.60.

Example 2

Preparation of 2-{4-[2-(3,4-Dichloro-phenyl)-ethyl] phenylamino}-5-nitrobenzoic acid Step C (Scheme 6): Preparation of 2-{4-[2-(3,4-Dichloro-phenyl)-ethyl]phenylamino}-5-nitrobenzoic acid methyl ester A mixture of 4-[2-(3,4-dichlorophenyl)-ethyl]benzenamine (600 mg, 2.25 mmol), 2-bromo-5-nitrobenzoic acid methyl ester (489 mg, 1.88 mmol), cesium carbonate (857 mg, 2.62 mmol), tris(dibenzylideneacetone-dipaladium (0) (51 mg, 0.056 mmol) and (S)-(2,2'-bis(di-p-tolylphosphino-1,1'-binaphthyl (98%, (S)-tol-BINAP) (58 mg, 0.085 mmol) (Ligand/Pd=1.5) in anhydrous toluene (16 mL) was heated to 100° C. for 12 hours under $N_2$. After cooling, the reaction mixture was diluted with ether, filtered through celite and rinsed thoroughly with ether. The filtrate was evaporated to dryness to give a brown residue. Purification by flash chromatography (silica gel, 5% EtOAc/hexane) yielded 540 mg (1.21 mmol, 64%) of the desired product. mp 107–108° C.

Analysis for $C_{22}H_{18}N_2Cl_2O_4$: Calcd: C, 59.34; H, 4.07; N, 6.29. Found: C, 59.03; H, 4.04; N, 5.99.

Preparation of 2-{4-[2-(3,4-Dichloro-phenyl)-ethyl] phenylamino}-5-nitrobenzoic acid A solution of 2-{4-[2-(3,4-dichloro-phenyl)-ethyl] phenylamino}-5-nitrobenzoic acid methyl ester (340 mg, 0.76 mmol) and 1N NaOH (aq.) (4.0 mL) in EtOH (4.0 mL) and THF (4.0 mL) was heated to reflux for 16 hours. The solvent was removed in vacuum. The residue was diluted with $H_2O$ and acidified with concentrated HCl to pH 1. The mixture was then extracted with methylene chloride, dried ($Na_2SO_4$), filtered and concentrated in vacuo to yield a yellow solid, 329 mg (0.76 mmol, 100%) of the desired product mp 214–217° C.

Analysis for $C_{21}H_{16}N_2Cl_2O_4$: Calcd: C, 58.49; H, 3.74; N, 6.50. Found: C, 58.24; H, 3.81; N, 6.28.

Example 3

Preparation of 2-{4-[4-(3,4-Dichloro-phenyl)-ethyl] phenylamino}-4-methoxy-5-nitrobenzoic acid To a cooled (−78° C.) solution of 4-[2-(3,4-dichloro-phenyl)-ethyl]phenylamine (0.836 g, 3.14 mmol) in THF (20 mL), LHDMS (6.28 mL, 1 M in THF, 6.28 mmol) was added dropwise. The reaction mixture was allowed to stir at −78° C. for 10 minutes. A solution of 2-flouro-4-methoxy-5-nitrobenzoic acid methyl ester (0.72 g, 3.14 mmol) in THF (30 mL) was added dropwise, and this solution was stirred for 30 minutes at −78° C. The reaction mixture was allowed to gradually warm to room temperature and stir for 2 hours under a $N_2$ atmosphere. The reaction mixture was diluted with ethyl acetate (EtOAc), and acidified with 5N HCl (pH 3). The organic layer was dried ($Na_2SO_4$), filtered and concentrated in vacuo to yield a brown residue. To a solution of this residue in EtOH (20 mL) and THF (40 mL), 5N NaOH (50 mL) was added, and the mixture was refluxed for overnight The solvent was removed in vacuum, and the residue was acidified with concentrated HCl (pH 3). The precipitate was collected by filtration, triturated with boiling MeOH—$H_2O$ (1:1), and dried in a vacuum oven for 16 hours to give Example 3, an orange solid (0.70 g, 1.51 mmol, 48%). mp 208–209° C.

Analysis for $C_{22}H_{18}N_2O_5Cl_2$: Calcd: C, 57.28; H, 3.93; N, 6.07. Found: C, 57.43; H, 3.69; N, 5.86.

Example 4

Preparation of 2-{4-[2-(3,4-Dihydroxy-phenyl)-ethyl]-phenylamino}benzoic acid

Step A (Scheme 1): Preparation of 1,2-Dimethoxy-4-[2-(4-nitrophenyl)ethenyl]-benzene The title compound was prepared from p-nitrophenylacetic acid (25.0 g, 0.14 mol), and 3,4-dimethoxybenzaldehyde (21.0 g, 0.14 mol) in piperidine (5 mL) using the procedure described in Example 1, Step A, to yield a yellow solid, 13.4 g (0.047 mol, 34%) of the desired product. mp: 133–134° C.

Analysis of $C_{16}H_{15}N_1O_4$: Calcd: C, 67.36; H, 5.30; N, 4.91. Found: C, 66.81; H, 5.27; N, 4.84.

Step B (Scheme 1): Preparation of 4-[2-(3,4-Dimethoxy-phenyl)ethyl]-phenylamine 1,2-Dimethoxy-4-[2-(4-nitrophenyl)ethenyl]benzene (12.1 g, 0.042 mol) was reduced in the presence of 10% Pd—C (2.0 g) in dimethylformamide (DMF) (120 mL) at 25° C. under a hydrogen atmosphere. The reaction mixture was concentrated in vacuo to give a solid. The solid was recrystallized from MeOH (400 mL) to yield a white crystalline product, 6.8 g (0.026 mol, 63%) of the desired product. mp 115–116° C.

Analysis for $C_{16}H_{19}N_1O_2$: Calcd: C, 74.68; H, 7.44; N, 5.44. Found: C, 74.60; H, 7.39; N, 5.35.

Step C (Scheme 6): Preparation of 2-{4-[2-(3,4-Dimethoxy-phenyl)-ethyl]-phenylamino}benzoic acid The title compound was prepared from 4-[2-(3,4-dimethoxy-phenyl)-ethyl]phenylamine (9.25 g, 0.036 mol), 2-chlorobenzoic acid (5.2 g, 0.036 mol), anhydrous potassium carbonate (15.0 g, 0.11 mol), copper powder (0.45 g, 0.007 mol), and a catalytic amount of copper(I) chloride in dry DMF (75 mL) using the procedure described in Example 1, Step C, Method B. After crystallization with MeOH/$H_2O$, 4.5 g (0.012 mol, 33%) of the desired product was obtained mp: 137–139° C.

Analysis for $C_{23}H_{23}N_1O_4$: Calcd: C, 73.19; H, 6.14; N, 3.71. Found: C, 73.47; H, 6.03; N, 3.78.

Step D: Preparation of 2-{4-[2-(3,4-Dihydroxy-phenyl)-ethyl]-phenylamino}-benzoic acid To a solution of 2-{4-[2-(3,4-dimethoxy-phenyl)-ethyl] phenylamino}-benzoic acid (0.28 g, 0.74 mmol) in $CH_2Cl_2$ (20 mL), $BBr_3$ (3.5 mL, 1$\underline{M}$ in $CH_2Cl_2$, 3.5 mmol) was added at room temperature under a $N_2$ atmosphere. The reaction mixture was allowed to stir at room temperature for 2 hours and then poured into ice water (50 mL). This mixture was extracted with EtOAc, and the organic layer was washed two times with water, dried ($Na_2SO_4$), filtered and concentrated in vacuo to yield 0.24 g (0.69 mmol, 93%) of the desired product. mp 215–217° C.

Analysis for $C_{21}H_{19}NO_4$: Calcd: C, 72.19; H, 5.48; N, 4.00. Found: C, 71.80; H, 5.46; N, 3.99.

Example 5

Preparation of 2-{4-[2-(4-Dibutylamino-phenyl)-ethyl]phenylamino}benzoic acid

Step A (Scheme 1): Preparation of 1,1-Dibutylamino-4-[2-(4-nitrophenyl)ethenyl]benzene The title compound was prepared from p-nitrophenylacetic acid (9.92 g, 0.055 mol) and 4-dibutylamino-benzaldehyde (14.32 g, 0.055 mol) in piperidine (5 mL) using the procedure described in Example 1, Step A. This procedure yielded a red solid, 4.12 g (0.012 mol, 16%) of the desired product.

MS: 352.2. ($M^+$); 353.2. ($MH^+$).

Step B (Scheme 1): Preparation of 4-[2-(4,4-Dibutylaminophenyl)ethyl]-phenylamine The title compound was prepared from 1,1-dibutylamino-4-[2-(4-nitrophenyl)ethenyl]benzene (4.10 g, 11.63 mmol) and Ra—Ni (2.0 g) in MeOH (100 mL) at 21° C. to 32° C. ($\Delta P=3.6$ psi) under a hydrogen atmosphere using the procedure described in Example 1, Step B. This procedure yielded a colorless oil, 3.49 g (10.76 mmol, 92.6%) of the desired product.

MS: 325.3 ($MH^+$).

Step C (Scheme 6): Preparation of 2-{4-[2-(4-Dibutylamino-phenyl)-ethyl]phenylamino}-benzoic acid The title compound was prepared from 2-chlorobenzoic acid (1.46 g, 9.36 mmol), 4-[2-(4,4-dibutylaminophenyl) ethyl]phenylamine (3.31 g, 10.20 mmol), anhydrous potassium carbonate (4.27 g, 30.88 mmol), copper powder (1.25 g, 19.65 mmol), and copper(I) chloride (0.092 g, 0.93 mmol) in dry DMF (30 mL) using the procedure described in Example 1, Step C, Method B. This procedure yielded a 0.39 g (0.87 mmol, 8.6%) of the desired product. mp 115–117° C.

Analysis for $C_{29}H_{36}N_2O_2$: Calcd: C, 78.34; H, 8.16; N, 6.30. Found: C, 78.15; H, 8.07; N, 6.10.

Example 6

Preparation of 2-{4-[2-(3,4,5-Trihydroxy-phenyl)-ethyl]phenylamino}benzoic acid

Step A (Scheme 1): Preparation of 1,2,3-Trimethoxy-5-[2-(4-nitrophenyl)ethenyl]benzene The title compound was prepared from p-nitrophenylacetic acid (18.6 g, 0.10 mol), 3,4,5-trimethoxy-benzaldehyde (19.6 g, 0.10 mol) and piperidine (5 mL) using the procedure described in Example 1, Step A. This procedure yielded a solid, 13.0 g (0.041 mol, 41%) of the desired product. mp: 192–195° C.

Step B (Scheme 1): Preparation of 4-[2-(3,4,5-Trimethoxy-phenyl)-ethyl]-phenylamine The title compound was prepared from 1,2,3-trimethoxy-5-[2-(4-nitrophenyl)ethenyl]benzene (9.5 g, 0.03 mol) and Ra—Ni (1.0 g) in THF (50 mL) at 21–26° C. ($\Delta P=9.6$ psi) under a hydrogen atmosphere using the procedure described in Example 1, Step B. This procedure yielded a tan powder, 6.6 g (0.023 mol, 74%) of the desired product. mp 91–93° C.

Step C (Scheme 6): Preparation of 2-{4-[2-(3,4,5-Trimethoxy-phenyl)-ethyl]phenylamino}-benzoic acid methyl ester The title compound was prepared from 4-[2-(3,4,5-trmethoxyphenyl)-ethyl]phenylamine (0.75 g, 2.61 mmol), methyl 2-bromobenzoate (0.47 g, 2.17 mmol), cesium carbonate (0.99 g, 3.04 mmol), tris(dibenzylideneacetone-dipaladium(0) (0.06 g, 0.065 mmol) and (S)-(-0-2,2'-bis(di-p-tolylphosphino-1,1'-binaphthyl (98% (S)-Tol-BINAP) (0.066 g, 0.098 mmol) (Ligand/Pd=1.5) in anhydrous toluene (100 mL) using the procedure described in Example 1, Step C, Method A to yield a yellow oil, 0.69 g (1.63 mmol, 76%) of the desired product.

Analysis for $C_{25}H_{27}N_1O_5$: Calcd: C, 71.24; H, 6.46; N, 3.32. Found: C, 71.53; H, 6.24; N, 3.14.

Preparation of 2-{4-[2-(3,4,5-Trimethoxy-phenyl) ethyl]phenylamino}-benzoic acid To a solution of 2-{4-[2-(3,4,5-trimethoxyphenyl)ethyl] phenylamino}-benzoic acid methyl ester (0.62 g, 1.47 mmol) in THF-EtOH (2:1, 6 mL), 1N NaOH solution (4 mL) was added, and the reaction mixture was heated to reflux for 5 hours. The reaction mixture was then concentrated in vacuo to remove the organic solvent. The residue was acidified with concentrated HCl (pH 3). This precipitate was collected by filtration, triturated with boiling MeOH—$H_2O$ (4:1) and dried in vacuum at room temperature for 16 hours to give the title compound as a white solid, 0.59 g (1.45 mmol, 98.5%). mp 146.0–147.0° C.

Analysis for $C_{24}H_{25}N_1O_5$: Calcd: C, 70.75; H, 6.18; N, 3.44. Found: C, 70.54; H, 6.43; N, 3.15.

Step D: Preparation of 2-{4-[2-(3,4,5-Trihydroxyphenyl)-ethyl]phenylamino}-benzoic acid The title compound was prepared from 2-{4-[2-(3,4,5-trimethoxy-phenyl)-ethyl]phenylamino}benzoic acid (0.50 g, 1.23 mmol) in $CH_2Cl_2$ (40 mL) and $BBr_3$ (10 mL, 1M in $CH_2Cl_2$, 10.0 mmol) using the procedure described in Example 4, Step D. This procedure yielded a green solid, 0.25 g (0.68 mmol, 65%) of the desired product. mp: 160.0–162.0° C.

Analysis for $C_{21}H_{19}N_1O_5.1.44\ H_2O$: Calcd: C, 64.46; H, 5.64; N, 3.58. Found: C, 64.07; H, 5.27; N, 3.39.

Example 7

Preparation of 2-{4-[2-[-(3,4-Dichlorophenyl) propyl]phenylamino}-4-methoxy-5-nitrobenzoic acid Step A' (Scheme 2): Preparation of 3-(3,4-Dichlorophenyl)-1-(4-nitro-phenyl)propenone Sodium hydroxide (7.3 g, 0.18 mol) was dissolved in water (80 mL) and 95% EtOH (80 mL) and cooled to 10° C. with an ice-$H_2O$ bath. 3,4-Dichlorobenzaldehyde (31.8 g, 0.18 mol) was added in one portion. After the addition, the mixture was warmed to 15° C. 1-(4-Nitrophenyl)ethanone (30.0 g, 0.18 mol) was added at this temperature with rigorous stirring. After stirring for 5 minutes, the reaction mixture was diluted with 95% EtOH (300 mL). The resulting tan mixture was stirred at room temperature for 30 minutes, then stirred with an ice-$H_2O$ bath underneath the flask for 2 hours. The light brown solid was filtered off, washed with $H_2O$, and air-dried. The solid was dissolved in hot THF (1.5 L) and treated with charcoal. The resulting mixture was filtered off, and the filtrate was diluted with 95% EtOH (500 mL). This solution was filtered and oven-dried (40° C.) to yield a light brown solid, 38.56 g (0.12 mol, 66%) of the title compound. mp 220–223° C.

Analysis for $C_{15}H_9Cl_2NO_3$: Calcd: C, 55.93; H, 2.82; Cl, 22.01; N, 4.35. Found: C, 55.79; H, 2.93; Cl, 22.16; N, 4.32.

Step B' (Scheme 2): Preparation of 1-(4-Amino-phenyl)-3-(3,4-dichlorophenyl)propan-1-one 3-(3,4-Dichlorophenyl)-1-(4nitro-phenyl)propenone (34.56 g, 0.11 mol) was reduced in the presence of Ra—Ni (3.0 g) in THF (250 mL) at 20° C. to 32° C. (ΔP=33.4 psi) under a hydrogen atmosphere. The reaction mixture was concentrated in vacuo and recrystallized from MeOH (100 mL) to give a light yellow solid, 23.5 g (0.080 mol, 75%) of the desired product mp 127–129° C. Analysis for $C_{15}H_{13}Cl_2NO$: Calcd: C, 61.24; H, 4.45; N, 4.76; Cl, 24.10. Found: C, 60.91; H, 4.60; N, 4.70; Cl, 23.98.

Step C' (Scheme 2): Preparation of 4-[3-(3,4-Dichlorophenyl)propyl]phenylamine

A mixture of 1-(4-aminophenyl)-3-(3,4-dichlorophenyl)propan-1-one (20.0 g, 0.068 mol), $NH_2NH_2$—$H_2O$ (16 mL), and KOH (85%, 5.6 g) in ethylene glycol (160 mL) was heated to reflux under a N2 atmosphere for 16 hours. After cooling to room temperature, the reaction mixture was poured into ice-$H_2O$ and extracted with $CH_2Cl_2$ (2 L). The layers were separated, and the organic layer was dried ($Na_2SO_4$) and concentrated in vacuo to afford an oil. Purification by flash chromatography (silica gel, $CH_2Cl_2$) yielded an oil, 14.00 g (0.05 mol, 73%) of the desired product.

Analysis for $C_{15}H_{15}Cl_2N$: Calcd: C, 64.30; H, 5.40; N, 4.99; Cl, 25.31. Found: C, 64.21; H, 5.59; N, 5.24; Cl, 24.87.

Preparation of 2,4-Difluoro-5-nitrobenzoic acid methyl ester

Fuming nitric acid 90% (8.5 mL, 0.19 mol) was added with gentle stirring to concentrated sulfuric acid 98% (125 mL) in a 1 L beaker. After stirring for 10 minutes at room temperature, 2,4-difluorobenzoic acid methyl ester (21.9 g, 0.127 mol) was added dropwise. After the addition, the reaction mixture was allowed to stir gently for 40 minutes at room temperature. The reaction mixture was then poured into ice-$H_2O$ (1 L) and stirred for 10 minutes. The mixture was extracted with EtOAc. The layers were separated, and the organic layer was washed sequentially with 1$\underline{N}$ NaCl, saturated $NaHCO_3$, $H_2O$ and brine, dried ($Na_2SO_4$), filtered and concentrated in vacuo to afford a yellow residue. This residue was washed with 10% EtOAc/hexane, filtered, and dried to yield a pale yellow solid, 29.0 g (0.133 mol, 82%). mp 78–80° C. Analysis for $C_8H_5F_2NO_4$: Calcd: C, 44.25; H, 2.32; N, 6.45. Found: C, 44.18; H, 2.39; N, 6.14.

Preparation of 2-Fluoro-4-methoxy-5-nitrobenzoic acid methyl ester

A mixture of sodium metal (1.27 g, 0.055 mol) and MeOH (250 mL) was stirred at 0° C. for 10 minutes. This solution was added to a solution of 2-fluoro-5-nitrobenzoic acid methyl ester (10.0 g, 0.046 mol) in MeOH (250 mL), and the mixture was stirred for 20 minutes at 0° C. to 5° C. The reaction mixture was then allowed to warm to room temperature and stir for 2 hours. The mixture was then filtered to give an off-white precipitate. Recrystallization with $CHCl_3$ (70 ml) yielded an off-white crystalline solid, 1.825 g (0.008 mol, 17%) of the title compound.

Analysis for $C_9H_8F_1N_1O_5$: Calcd: C, 47.17; H, 3.52; N, 6.11. Found: C, 47.09; H, 3.47; N, 6.00.

Preparation of 2-{4-[3-(3,4-Dichlorophenyl)propyl]phenylamino}-4-methoxy-5-nitrobenzoic acid methyl ester A mixture of 4-[3-(3,4-dichloro-phenyl)propyl]phenylamine (0.94 g, 3.3 mmol), 2-fluoro-4-methoxy-5-nitro-benzoic acid methyl ester (0.75 g, 3.3 mmol), and $Et_3N$ (0.46 mL) in $CH_3CN$ (30 mL) was heated to reflux for 120 hours. The reaction mixture was cooled to room temperature, diluted with $CH_2Cl_2$ and washed with saturated $NaHCO_3$. The organic layer was dried ($Na_2SO_4$) and concentrated to give a solid. Recrystallization with MeOH yielded 0.67 g (1.37 mmol, 42%) of the desired product.

Analysis for $C_{24}H22N_2Cl_2O_5$·0.42$H_2O$: Calcd: C, 58.01; H, 4.63. N, 5.64; Found: C, 57.61; H, 4.51; N, 5.94.

Preparation of 2-{4-[3-(3,4-Dichlorophenyl)propyl]phenylamino}-4-methoxy-5-nitrobenzoic acid To a solution of 2-{4-[3-(3,4-dichlorophenyl)propyl]phenylamino}-4-methoxy-5-nitrobenzoic acid methyl ester (0.30 g, 0.061 mol) in THF (5 mL), 1N NaOH (aq.) (2.5 mL) was added, and the mixture was stirred for 36 hours at room temperature. The solvent was removed, and the residue was acidified with concentrated HCl to pH 3. The precipitate was collected by filtration and dried in vacuum for 16 hours. Recrystallization with MeOH gave the title compound as an orange solid 0.21 g (0.043 mol. 70%). mp 200–201° C.

Analysis for $C_{23}H_{20}N_2O_5Cl_2$·0.2$H_2O$: Calcd: C, 57.68; H, 4.29; N, 5.85; Cl, 14.81. Found: C, 57.71; H, 4.34; N, 5.58; Cl, 14.56.

Example 8

Preparation of 2-{4-[2-[-(3,4-Dichlorophenyl)propyl]phenylamino}-4-imidazo-1-yl-5-nitrobenzoic acid Preparation of 2-{4-[2-[-(3,4-Dichlorophenyl)propyl]phenylamino}-4-imidazo-1-yl-5-nitrobenzoic acid methyl ester A mixture of 2,4-difluoro-5-nitrobenzoic acid methyl ester (1.63 g, 7.5 mmol), imidazole (0.56 g, 8.25 mmol), and $Et_3N$ (1.14 mL, 8.25 mmol) in $CH_3CN$ (50 mL) was stirred for 16 hours at room temperature. To this deep orange solution, 4-[3-(3,4dichlorophenyl)propyl]phenylamine (2.10 g, 7.5 mmol) and triethylamine ($Et_3N$) (1.14 mL, 8.25 mmol) was added, and the mixture was heated to reflux for overnight. The reaction mixture was cooled and concentrated in vacuo to afford a residue. This residue was diluted with $CH_2Cl_2$ and washed with a saturated $K_2HCO_3$ solution. The organic layer was dried ($Na_2SO_4$), filtered, and concentrated in vacuo to give a crude oil. Purification by flash chromatography (silica gel, 10% EtOAc/hexane) yielded 1.0 g (1.90 mmol, 25%) of the desired product.

MS: 524.1 ($M^+$).

Preparation of 2-{4-[2-[-(3,4-Dichlorophenyl)propyl]phenylamino}-4-imidazo-1-1-yl-5-nitrobenzoic acid The title compound was prepared from 2-{4-[2-[3,4-dichlorophenyl)propyl]phenylamino}-4-imidazo-1-yl-5-nitrobenzoic acid methyl ester (1.0 g, 1.9 mmol), 1$\underline{N}$ NaOH (2.0 mL) in THF (30 mL) using the procedure described in Example 8. This procedure yielded an orange solid, 0.30 g (0.6 mmol, 32%) of the desired product.

Analysis for $C_{25}H_{20}Cl_2N_4O_4$·0.2$H_2O$: Calcd: C, 58.31; H, 3.99; N, 10.88; Cl, 13.89. Found: C, 58.34; H, 4.07; N, 10.73; Cl, 13.41.

Example 9

Preparation of 2-{4-[3-(3,4-Dichlorophenyl)-propyl]phenylamino}-benzoic acid

Preparation of 2-{4-[3-(3,4-Dichlorophenyl)propyl]phenylamino}-benzoic acid methyl ester The title compound was prepared from 4-[3-(3,4-dichlorophenyl)propyl]-phenylamine (600 mg, 2.14 mmol), 2-bromobenzoic acid methyl ester (380 mg, 1.78 mmol), cesium carbonate (812 mg, 2.49 mmol), tris(dibenzylideneacetone-dipaladium(0) (49 mg, 0.053 mmol) and (S)-2,2'-bis(di-p-tolylphosphino-1,1'-binaphthyl (98%, (S)-tol-BINAP) (54 mg, 0.080 mmol) (Ligand/Pd=1.5) in anhydrous toluene (15 mL) using the procedure described in Example 2, Step C. This procedure yielded an yellow oil, 0.61 g (1.47 mmol, 69%) of the desired product.

MS: 414 ($M^+$), 416 ($MH^+$). Analysis for $C_{23}H_{21}Cl_2O_2N \cdot 0.4\ H_2O$: Calcd: C, 65.25; H, 5.23; N, 3.30. Found: C, 65.76; H, 5.18; N, 3.10.

Preparation of 2-{4-[3-(3,4-Dichlorophenyl)propyl]phenylamino}-benzoic acid

The title compound was prepared from 2-{4-[3-(3,4-dichlorophenyl)-propyl]phenylamino}benzoic acid methyl ester (0.41 g, 0.99 mmol), 1$\underline{N}$ NaOH (4.0 mL) in EtOH (4 mL) and THF (4 mL) using the procedure described in Example 2. This procedure yielded a yellow solid, 0.32 g (0.80 mmol, 81%) of the desired product mp 120–126° C.

Analysis for $C_{22}H_{19}Cl_2O_2N_1 \cdot 0.75\ H_2O$: Calcd: C, 64.04; H, 5.00; N, 3.39. Found: C, 64.17; H, 4.69; N, 3.18.

Example 10

Preparation of 2-{4-[4-(3,4-Dichlorophenyl)butyl]phenylamino}benzoic acid

Preparation of (trans)-3-(3,4-Dichlorophenyl)-2-propenal

A mixture of 3,4-dichlorobenzaldehyde (140.0 g, 0.8 mol) and acetaldehyde (300 mL) was cooled to 5° C. Potassium hydroxide (5.1 g, 0.091 mol) was dissolved in hot MeOH (40 mL), and the resulting solution was added to the above cooled mixture while maintaining the internal temperature at 25° C. to 30° C. The mixture was allowed to stir in ice-$H_2O$ bath for 40 minutes and then treated with acetic anhydride (400 mL). After the addition, the mixture was heated to 100° C. with string for 30 minutes and then cooled to 30° C. To this mixture, 12$\underline{N}$ HCl/$H_2O$ (102 mL/1.2 L) was added, and the resulting mixture was heated to reflux for 30 minutes and then cooled to room temperature. This heterogeneous mixture was filtered and washed with $H_2O$ to afford a brown solid. The crude product was dissolved in EtOAc and washed with H2O, dried $Na_2SO_4$), and concentrated to dryness. Recrystallization from hexane/EtOAc (9:1) yielded 76.5 g (0.38 mol, 48%) of the title compound. mp: 91–93° C.

Analysis for $C_9H_6Cl_2O$: Calcd: C, 53.77; H, 3.01; Cl, 35.27. Found: C, 53.75; H, 3.10; Cl, 35.58.

Preparation of (trans), (trans)-1,2-Dichloro-4-[4-(4-nitrophenyl)-1,3-butadienyl]benzene A mixture of 4-nitro-benzyl bromide (200.0 g, 0.93 mol) and triphenylphosphine (244.0 g, 0.93 mol) in $CHCl_3$ (1.5 L) was heated to reflux for overnight. The reaction mixture was cooled to room temperature, concentrated in vacuo to remove $CHCl_3$ and then suspended in $Et_2O$ and stirred rigorously. The suspension was filtered, and the off-white solid was washed with $Et_2O$, dried at 80° C. for 16 hours to give 433.0 g (0.91 mol, 98%) of bromo[(4-nitrophenyl)methyl]triphenylphosphine. A solution of bromo[(4-nitrophenyl)methyl]triphenylphosphine (100.0 g, 0.23 mol) in dry THF (500 mL) was cooled to 5° C. n-Butyl lithium (n-BuLi) (2.4 M, 96 mL, 0.23 mol) was added dropwise to maintain the temperature between 5° C. to 10° C. The cooling bath was then removed, and the reaction mixture was allowed to warm to room temperature. After 4 hours, a solution of (trans)-3-(3,4-dichlorophenyl)-2-propenal (36.2 g, 0.18 mol) in THF (100 mL) was added dropwise, and the resulting mixture was stirred at room temperature for 16 hours. The mixture was filtered, and the filtrate was concentrated in vacuo to give a residue. Purification by flash chromatography (silica gel, 20% EtOAc/hexane) yielded 16.0 g (0.05 mol, 28%) of the desired product. mp 125–135° C.

Analysis for $C_{16}H_{11}Cl_2NO_2$: Calcd: C, 60.02; H, 3.46; N, 4.37, Cl, 22.15. Found: C, 59.77; H, 3.47; N, 4.40; Cl, 22.39.

Preparation of 4-[4-(3,4-Dichloro-phenyl)-butyl]-phenylamine

The title compound was prepared from (trans), (trans)-1,2-dichloro-4-[4-(4-nitrophenyl)-1,3-butadienyl]benzene (15.42 g, 0.048 mol), Ra—Ni (1 g) at 20° C. to 26° C. (ΔP=19.3 psi) under a hydrogen atmosphere in THF (75 mL) and MeOH (75 mL) using the procedure described in Example 1, Step B. This procedure yield a solid, 10.97 g (0.037 mol, 78%) of the desired product. mp 50–52° C.

Analysis of $C_{16}H_{17}N_1Cl_2$: Calcd: C, 65.32; H, 5.82; N, 4.76. Found: C, 65.43; H, 5.84; N, 4.61.

Preparation of 2-{4-[4-(3,4-Dichlorophenyl)butyl]phenylamino}benzoic acid

The title compound, mp 98–105° C., was prepared from 4-[4-(3,4-dichlorophenyl)butyl]phenylamine (0.50 g, 1.7 mmol), 2-chlorobenzoic acid (0.24 g, 1.56 mmol), anhydrous potassium carbonate (0.71 g, 5.15 mmol), copper powder (0.21 g, 3.28 mmol), and copper(I) chloride (0.015 g, 0.15 mmol) in dry DMF (5 mL) using the procedure described in Example 1, Step C, Method B.

Example 11

Preparation of 2-{4-[4-(3,4-Dichloro-phenyl)-butyl]-phenylamino}-5-nitro-benzoic acid

A mixture of 2-fluoro-5-nitrobenzoic acid (1.85 g, 0.01 mol), 4-[4-(3,4-dichlorophenyl)butyl]-phenylamine (2.94 g, 0.01 mol) and $Et_3N$ (2.80 mL) in acetonitrile (110 mL) was heated to reflux for 48 hours. The reaction mixture was cooled and concentrated in vacuo to remove the solvent. The residue was dissolved in $CH_2C_2$ and washed with diluted HCl. The organic layer was dried $Na_2SO_4$), concentrated in vacuo to give a crude solid. Purification by flash chromatography (silica gel, $CH_2Cl_2$) yielded 1.40 g (0.003 mol, 30%) of the desired product.

Analysis for $C_{23}H_{19}N_2O_4Cl_2$: Calcd: C, 60.27; H, 4.18; N, 6.11; Cl, 14.47. Found: C, 60.16; H, 4.41; N, 6.09; Cl, 15.69.

Example 12

Preparation of 2-{4-[4-(3,4-Dichlorophenyl)butyl]phenylamino}-3,5-dinitrobenzoic acid

To a cooled (0° C.) solution of 4-[4-(3,4-dichlorophenyl)butyl]-phenylamine (1.47 g, 5.0 mmol) and DBU (0.75 mL, 7.5 mmol) in acetonitrile (25 mL), a solution of 2-fluoro-2,5-dinitrobenzoic acid (1.15 g, 5.0 mmol) in acetonitrile (15 mL) was added dropwise. After stirring for 30 minutes at 0° C., the reaction mixture was neutralized with dilute HCl and extracted with EtOAc, dried ($Na_2SO_4$), filtered and concentrated in vacuo to afford a crude residue. Recrystallization with EtOH yielded a bright orange solid, 2.06 g (4.1 mmol, 82%) of the title compound.

Analysis for $C_{23}H_{19}Cl_2N_3O_6$: Calcd: C, 54.77; H, 3.80; N, 8.33; Cl, 14.06. Found: C, 54.68; H, 4.00; N, 8.12; Cl, 13.81.

Example 13

Preparation of 2-{4-[5-(3,4-Dichlorophenyl)pentyl] phenylamino}-5-nitrobenzoic acid Preparation of Bromo[(3,4-dichlorophenyl)methyl] triphenylphosphine A mixture of 4-bromomethyl-1,2-dichlorobenzene (2.40 g, 0.01 mol), and triphenylphosphine (5.24 g, 0.02 mol) in toluene (30 mL) was stirred for 16 hours at room temperature. The solid was filtered, rinsed with toluene, and oven-dried at room temperature to yield a white powder, 3.95 g (0.0078 mol, 78%) of the desired product.

$^1$H NMR [dimethylsulfoxide (DMSO):ppm]:7.89–7.61 (m, 15H), 7.50 (d, J=8.3 Hz, 1H), 7.04 (t, J=2.3 Hz, 1H), 6.97 (m, 1H), 5.20 (d, J=15.9 Hz, 2H).

Preparation of 4-(4-Nitrophenyl)butyraldehyde

To a cooled solution (−70° C.) of oxalyl chloride (2.0 M in $CH_2Cl_2$, 14.1 mL, 28.2 mmol), dimethylsulfoxide (DMSO) (4.40 g, 56.32 mmol) in $CH_2Cl_2$ (20 mL) was added dropwise. The resulting reaction mixture was then stirred for 30 minutes at −70° C. under a nitrogen atmosphere. A solution of 4-(4-nitrophenyl)butan-1-ol (5.00 g, 25.6 mmol) in $CH_2Cl_2$ (3 mL) was added dropwise, and the reaction mixture was stirred for 1 hour at −70° C. $Et_3N$ (16 mL, 115 mmol) was added, and the reaction mixture was then allowed to gradually warm to room temperature and stir for 30 minutes. The mixture was then quenched with $H_2O$ and extracted with EtOAc. The organic layers were washed with 0.1N HCl solution, $H_2O$, brine, dried ($Na_2SO_4$), filtered, and concentrated in vacuo to give a lightly brown oil. Purification by flash chromatography (silica gel, 50% EtOAc/hexane) yielded 3.20 g (16.56 mmol, 65%) of the desired product.

$^1$H NMR (DMSO:ppm): 9.75 (s, 1H), 8.12 (d, J=8.3 Hz, 2H), 7.30 (d, J=8.3 Hz, 2H), 2.72 (t, J=7.7 Hz, 2H), 2.47 (t, J=7.1 Hz, 2H), 1.94 (m, 2H).

Preparation of 1,2-Dichloro-4-[5-(4-nitrophenyl)-1-pentenyl]benzene

A solution of bromo[(3,4-dichlorophenyl)methyl] triphenylphosphine (3.95 g, 7.9 mmol) in dry THF (20 mL) was cooled to 0° C. LHDMS (1.0 M/THF, 9 ml, 9.0 mol) was added dropwise to maintain the temperature at 0° C. After stirring for 30 minutes, a solution of 4-(4-nitro-phenyl) butyraldehyde (1.45 g, 7.5 mmol) in TBF (5 mL) was added dropwise, and the mixture was allowed to warm to room temperature within 2 hours. The mixture was then quenched with $H_2O$ and extracted with EtOAc. The organic layers were washed with 0.1N HCl solution, $H_2O$, brine, dried ($Na_2SO_4$), filtered, and concentrated in vacuo to give a lightly brown oil. Purification by flash chromatography (silica gel, 10% EtOAc/hexane) yielded 2.5 g (7.4 mmol, 99%) of the desired product.

MS: 335 (M$^+$), 337 (MH$^+$).

Preparation of 4-[5-(3,4-Dichlorophenyl)pentyl] phenylamine

The title compound was prepared from 1,2-dichloro-4-[5-(4-nitrophenyl)-1-pentenyl]benzene (2.5 g, 7.4 mmol), Ra—Ni (1 g) in TBF (50 mL) at 25° C. to 40° C. (ΔP=9.9 psi) using the procedure described in Example 1, Step B. This procedure yielded 1.06 g (3.4 mmol, 46%) of the desired product.

$^1$H NMR (DMSO:ppm): 7.45 (d, J=78.3 Hz, 1H), 7.41 (d, J=2.2 Hz, 1H), 7.12 (m, 1H), 6.74 (d, J=8.3 Hz, 2H), 6.40 (d, J=78.3 Hz, 2H), 4.73 (s, 2H), 2.50 (t, J=7.7 Hz, 2H), 2.31 (t, J=7.6 Hz, 2H), 1.6–1.5 (m, 4H), 1.5–1.4 (m, 2H).

Preparation of 2-{4-[5-(3,4-Dichloro-phenyl)pentyl] phenylamino}-5-nitrobenzoic acid To a cooled (−78° C.) solution of 4-[5-(3,4-dichlorophenyl)pentyl]-phenylamine (0.231 g, 0.75 mmol) in THF (2 mL), LHDMS (2.25 mL, 1 M in hexane, 2.25 mmol) was added dropwise. The reaction mixture was allowed to stir at −78° C. for 10 minutes. A solution of 2-fluoro-5-nitrobenzoic acid (0.139 g, 0.75 mmol) in THF (2 mL) was added dropwise, and this solution was stirred for 30 minutes at −78° C. The reaction mixture was allowed to gradually warm to room temperature and stir for 2 hours under $N_2$ atmosphere. The reaction mixture was diluted with EtOAc, and acidified with 1N HCl (pH 3). The organic layer was dried ($Na_2SO_4$), filtered and concentrated in vacuo to yield a brown residue. Purification by flash chromatography (silica gel, 2% MeOH/$CH_2Cl_2$) then recrystallization with MeOH yielded 265 mg (0.56 mmol, 75%) of the desired product. mp 147–148° C.

Analysis for $C_{24}H_{22}Cl_2N_2O_4 \cdot 0.37H_2O$: Calcd: C, 60.05; H, 4.77; N, 5.84. Found: C, 59.67; H, 4.64; N, 5.51.

Example 14

Preparation of 2-{4-[5-(3,4-Dichloro-phenyl)pentyl] phenylamino}methoxy-5-nitrobenzoic acid Preparation of 2-{4-[5-(3,4-Dichlorophenyl)pentyl] phenylamino}-4-methoxy-5-nitrobenzoic acid methyl ester The title compound was prepared from 4-[5-(3,4-dichlorophenyl)pentyl]phenylamine (231 mg, 0.75 mmol), LHDMS (6.28 mL, 1 M in THF, 6.28 mmol) and 2-fluoro-4-methoxy-5-nitrobenzoic acid methyl ester (172 g, 0.75 mmol) in THF (5 mL) using the procedure described in Example 13. Purification by flash chromatography (silica gel, 10% EtOAc/hexane) yielded 145 mg (0.28 mmol, 37%) of the desired product

MS: 515.2 (M$^+$), 517.2 (MH$^+$).

Preparation of 2-{4-[5-(3,4-Dichlorophenyl)pentyl] phenylamino}-4-methoxy-5-nitrobenzoic acid The title compound was prepared from 2-{4-[5-(3,4-dichlorophenyl)-pentyl]phenylamino}-4-methoxy-5-nitrobenzoic acid methyl ester (145 mg, 0.28 mmol) and 1N NaOH (aq.) (0.56 mL) in THF (1.2 mL) using the procedure described in Example 2. Purification by flash chromatography (silica gel, 10% MeOH/$CH_2Cl_2$), then recrystallization with MeOH yielded 58 mg (0.12 mmol, 41%) of the desired product. mp 192–193° C.

Analysis for $C_{25}H_{24}Cl_2N_2O_5$: Calcd: C, 59.65; H, 4.81; N, 5.56. Found: C, 59.29; H, 4.58; N, 5.36.

Example 15

Preparation of 2-{4-[3-(3,4-Dichlorophenyl)propyl] phenylanino}-5-nitrobenzoic acid Preparation of 2-{4-[3-(3,4-Dichlorophenyl)propyl] phenylamino}-5-nitrobenzoic acid methyl ester The title compound was prepared from 4-[3-(3,4-dichlorophenyl)propyl]-phenylamine (420 mg, 1.50 mmol), 2-bromobenzoic acid methyl ester (310 mg, 1.25 mmol), cesium carbonate (569 mg, 1.75 mmol), tris (dibenzylideneacetone-dipaladium(0) (34 mg, 0.037 mmol) and (S)-(2,2'-bis(di-p-tolylphosphino-1,1'-binaphthyl (98%, (S)-tol-BINAP) (38 mg, 0.056 mmol) (Ligand/Pd=1.5) in anhydrous toluene (15 mL) using the procedure described in Example 2, Step C. This procedure yielded an orange solid 0.51 g (1.11 mmol, 74%) of the desired product. mp 117–118° C.

MS: 457.1 (M$^+$); 459.1 (MH$^+$)

Preparation of 2-{4-[3-(3,4-Dichlorophenyl)propyl] phenylamino}-5-nitrobenzoic acid The title compound was 2-{4-[3-(3,4-dichlorophenyl)-propyl]phenylamino}-5-nitrobenzoic acid methyl ester (0.50 g, 1.09 mmol), 2N NaOH (5.0 mL) in EtOH (2 mL) and THF (4 mL) using the procedure described in Example 2. This procedure yielded an orange solid, 0.49 g (1.10 mmol, 100%) of the desired product. mp 153–155° C.

MS: 443.2 (M$^+$), 445.2 (MH$^+$)

Example 16

Preparation of 2-{4-[2-(3,4-Dimethyl-phenyl)-ethyl]phenylamino}-5-nitrobenzoic acid Preparation of 2-{4-[2-(3,4-Dimethyl-phenyl)-ethyl]phenylamino}-5-nitrobenzoic acid methyl ester The title compound was prepared from 4-[2-(3,4-dimethylphenyl)ethyl]-benzenamine (1.0 g, 4.43 mmol), 2-bromo-5-nitrobenzoic acid methyl ester (0.96 g, 3.69 mmol), cesium carbonate (1.68 g, 5.17 mmol), tris(dibenzylideneacetone-dipaladium(0) (101 mg, 0.11 mmol) and (S)-(2,2'-bis(di-p-tolylphosphino-1,1'-binaphthyl (98%, (S)-tol-BINAP) (113 mg, 0.17 mmol) (Ligand/Pd=1.5) in anhydrous toluene (32 mL) using the procedure described in Example 2, step C. This procedure yielded an yellow solid, 1.31 g (3.24 mmol, 73%) of the desired product. mp 115–117° C.

MS: 405 (M$^+$) Analysis for $C_{24}H_{24}O_4N_2 \cdot 0.25\ H_2O$: Calcd: C, 71.27; H, 5.98; N, 6.93. Found: C, 70.48; H, 6.03; N, 6.85.

Preparation of 2-{4-[2-(3,4-Dimethyl-phenyl)-ethyl]phenylamino}-5-nitrobenzoic acid The title compound was prepared 2-{4-[2-(3,4 dimethyl-phenyl)-ethyl]phenylamino}-5-nitrobenzoic acid methyl ester (1.12 g, 2.76 mmol), 1N NaOH (50 mL) in EtOH (50 mL) and THF (50 mL) using the procedure described in Example 2. This procedure yielded a yellow solid, 1.03 g (2.63 mmol, 81%) of the desired product. mp 214–216° C.

Analysis for $C_{23}H_{22}O_4N_2 \cdot 0.25\ H_2O$: Calcd: C, 69.99; H, 5.74; N, 7.18. Found: C, 69.90; H, 5.82; N, 6.81.

Example 17

Preparation of 2-[[4-[2-(4-Chloro-3-trifluromethylphenyl)ethyl]phenyl]amino-benzoic acid Step A (Scheme 1): Preparation of trans-1-Chloro-2-trifluoromethyl-4-[2-(4-nitrophenyl)ethenyl]benzene A mixture of p-nitrophenylacetic acid (51.85 g, 0.29 mol) and 4-chloro-3-trifluoromethylbenzaldehyde (47.85 g, 0.23 mol) in piperidine (19.5 g, 0.23 mol) was heated under $N_2$ atmosphere to 150° C. to 160° C. for 1 hour. The reaction mixture was cooled to 80° C. to 100° C. and refluxing i-PrOH (150 mL) was added. The mixture was continued to cool to room temperature and then placed under refrigeration for 5 hours. The crystalline precipitate was filtered off, rinsed with cold i-PrOH, and dried at room temperature in a vacuum oven overnight to yield trans-1-chloro-2-tifluoromethyl-4-[2-(4-nitrophenyl)ethenyl]benzene as an orange solid, 22.53 g (68.75 mmol, 30%). mp 173–174° C.

MS: 327.0 (M$^+$)

Step B (Scheme 1): Preparation of 4-[2-(4-Chloro-3-trifluoromethylphenyl)ethyl]-benzenamine The title compound was prepared from trans-1-chloro-2-trifluoromethyl-4-[2-(4-nitrophenyl)ethenyl]benzene (22.53 g, 0.069 mol) and Ra—Ni (22 g) in THF (0.5 L) at 18° C. to 29° C. (ΔP=20.5 psi) under a hydrogen atmosphere using the procedure described in Example 1, Step B. This procedure yielded a white solid, 20.0 g (66.73 mmol, 97%) of the desired product. mp 62–64° C.

MS: 298.1 (M$^+$)

Preparation of 2-[[4-[2-(4-Chloro-3-trifluromethylphenyl)ethyl]phenyl]-aminobenzoic acid To a cold solution of 4-[2-(4-chloro-3-trifluoromethylphenyl)ethyl]-benzenamine (4.33 g, 14.45 mmol) in THF (50 mL) at −78° C., was added LHMDS (43.35 mL, 43.35 mmol) (1M/THF) dropwise. Allowed the reaction mixture to stir for 10 minutes at −78° C. A solution of 2-fluorobenzoic acid (2.02 g, 14.45 mmol) in THF (50 mL) was added dropwise. The mixture was stirred for 2 hours at −78° C., then warmed to room temperature and let stir for additional 3 hours. The reaction mixture was concentrated in vacuo (40° C.) to remove the organic solvent. This residue was acidified to pH 3 with 3N HCl (aq.). This precipitate was collected by filtration, rinsed with 10% HCl (40 mL), and dried in vacuum for overnight to give as a pale solid, 4.3 g (10.24 mmol, 70%) of the desired product. mp 150–152° C.

Analysis for $C_{22}H_{17}O_2N_1ClF_3 \cdot 0.59\ H_2O$: Calcd: C, 61.39; H, 4.26; N, 3.25. Found: C, 61.01; H, 4.34; N, 3.30.

Example 18

Preparation of 2-[4-(3,4-Dichlorophenyl)phenylamino]benzoic acid

Preparation of o-Bromobenzoic Acid Potassium Salt

To a solution of o-bromobenzoic acid (201.03 g, 1.0 mol) in MeOH (500 mL), $K_2CO_3$ (69 g, 1.0 mol) was added. The mixture was concentrated to give the desired product (239.1 g, 1.0 mol, 100%).

Preparation of 2-[(4-Iodophenyl)amino]benzoic acid

A mixture of o-bromobenzoic acid potassium salt (47.8 g, 0.2 mol), 4-iodoaniline (43.8 g, 0.2 mol), $K_2CO_3$ (13.8 g, 0.1 mol), and cupric acetate (2.87 g, 6%) in diglyme (100 mL) was heated to reflux for 30 minutes. The reaction mixture was diluted with $H_2O$ (1.0 L) and filtered. The filtrate was acidified with diluted AcOH. The resulting precipitate was collected by filtration, washed with $H_2O$ and dried in a vacuum at 50° C. for 16 hours. Recrystallization from EtOAc gave the desired product, a solid (29.7 g, 0.087 mol, 44%). mp 205–206° C.

Analysis for $C_{13}H_{10}N_1O_2I$: Calcd: C,45.05; H, 2.97; N, 4.13. Found: C, 45.05; H, 2.97; N, 3.92.

Preparation of 2-[4-(3,4-Dichlorophenyl)phenylamino]benzoic acid

A mixture of 3,4-dichlorophenylboronic acid (880 mg, 2.3 mmol), 2-[(4-iodophenyl)amino]benzoic acid (339 mg, 1 mmol), $PdCl_2 \cdot dppf \cdot CH_2Cl_2$ [1,1'-bis(diphenylphosphino)ferrocene palladium (II) chloride, complexed with dichloromethane (1:1)] (67 mg, 0.082 mmol), $K_2CO_3$ (829 mg, 6 mmol), and $H_2O$ (2 mL) in dioxane (15 mL) was heated to reflux for 1 hour. The reaction mixture was diluted with EtOAc and filtered. The filtrate was treated with 1N HCl, washed with $H_2O$, brine, dried ($Na_2SO_4$), and concentrated in vacuum to give a yellow solid. Purification by flash chromatography (silica gel, 10% MeOH/$CH_2Cl_2$) yielded 272 mg (0.76 mmol, 76%) of the desired product. mp>220° C.

Analysis for $C_{19}H_{13}O_2N_1Cl_2$: Calcd: C; 63.23; H, 3.71; N, 3.88. Found: C, 62.95; H, 3.73; N, 3.63.

By following the general procedures described above, the following additional invention compounds were prepared:

Example 19

2-{4-[3-(4-Diethylaminophenyl)propyl] phenylamino}benzoic acid

MS: 403 (M$^+$). Analysis for C$_{26}$H$_{30}$N$_2$O$_2$.0.40 mol H$_2$O: Calcd: C, 69.31; H, 6.87; N, 6.12. Found: C, 69.29; H, 7.04; N, 6.35.

Example 20

2-{4-[3-(4-Nitrophenyl)propyl] phenylamino}benzoic acid. mp 150–153° C.

MS: 376 (M$^+$).

Example 21

2-{4-[3-(3-Nitrophenyl)propyl] phenylamino}benzoic acid. mp 164–167° C.

MS: 376 (M$^+$). Analysis for C$_{22}$H$_{20}$N$_2$O$_4$.2.20 mol H$_2$O: Calcd: C, 63.51; H, 5.91; N, 6.73. Found: C, 63.56; H, 5.45; N, 6.46.

Example 22

2-{4-[3-(4-Aminophenyl)propyl] phenylamino}benzoic acid. mp 110–112° C.

MS: 347 (M$^+$1$^+$).

Example 23

2-{4-[3-(3-Aminophenyl)propyl] phenylamino}benzoic acid. mp 109° C.

MS: 333 (M$^+$1$^+$).

Example 24

2-{4-[2-(4-Aminophenyl)phenylamino}benzoic acid. mp 198–201° C.

MS: 333 (M$^+$1$^+$). Analysis for C$_{21}$H$_{20}$N$_2$O$_2$.0.1 mol H$_2$O: Calcd: C, 75.47; H, 6.09; N, 8.38. Found: C, 75.32; H, 6.12; N, 8.27. Found: C, 75.32; H 6.12; N, 8.27.

Example 25

2-{4-[2-(4-Dipropylaminophenyl)ethyl] phenylamino}benzoic acid monohydrochloride. mp 176–177° C.

MS: 417 (M$^+$1$^+$). Analysis for C$_{27}$H$_{32}$N$_2$O$_2$: Calcd: C, 71.59; H, 7.34; N, 6.18; Cl, 7.83. Found: C, 71.31; H, 7.24; N, 6.19; Cl, 7.74.

Example 26

2-{4-[2-(4-Diethylaminophenyl)ethyl] phenylamino}benzoic acid monohydrochloride monohydrate MS: 389 (M$^+$1$^+$). Analysis for C$_{25}$H$_{28}$N$_2$O$_2$.HCl.H$_2$O: Calcd: C, 67.78; H, 7.05; N, 6.32; Cl, 8.00. Found: C, 67.83; H, 7.01; N, 6.30; Cl, 7.75.

Example 27

2-{4-[3-(3-Dipropylaminophenyl)propyl] phenylamino}benzoic acid

MS: 431 (M$^+$1$^+$). Analysis for C$_{28}$H$_{34}$N$_2$O$_2$.0.2 H$_2$O: Calcd: C, 77.46; H, 7.99; N, 6.45. Found: C, 77.43; H, 7.86; N, 6.40.

Example 28

2-{4-[3-(3-Dimethylaminophenyl)propyl] phenylamino}benzoic acid. mp 115–117° C.

MS: 374 (M$^+$), 375 (M$^+$1$^+$). Analysis for C$_{24}$H$_{26}$N$_2$O$_2$.0.1 H$_2$O: Calcd: C, 76.61; H, 7.02; N, 7.44. Found: C, 76.57; H, 7.21; N, 7.47.

Example 29

2-{4-[3-(4-Ethylaminophenyl)propyl] phenylamino}benzoic acid. mp 133° C.

MS: 375 (M$^+$1$^+$). Analysis for C$_{24}$H$_{26}$N$_2$O$_2$.0.1 H$_2$O: Calcd: C, 76.61; H, 7.02; N, 7.44. Found: C, 76.62; H, 7.06; N, 7.36.

Example 30

2-(N-{4-[3-(4-Diethylaminophenyl)propyl]phenyl}-N-ethylamino)benzoic acid

MS: 431 (M$^+$1$^+$). Analysis for C$_{28}$H$_{34}$N$_2$O$_2$: Calcd: C, 78.10; H, 7.96; N, 6.51. Found: C, 78.02; H, 8.17; N, 6.50.

Example 31

2-{4-[2-(3-Dibenzylaminophenyl)ethyl] phenylamino}benzoic acid. mp 95.5–97.5° C.

Analysis for C$_{35}$H$_{32}$N$_2$O$_2$O: Calcd: C, 82.00; H, 6.29; N, 5.46. Found: C, 81.81; H, 6.58; N, 5.44.

Example 32

2-{4-[3-(3-Diethylaminophenyl)propyl] phenylamino}benzoic acid

MS: 403 (M$^+$1$^+$). Analysis for C$_{26}$H$_{30}$N$_2$O$_2$.0.1 H$_2$O: Calcd: C, 77.23; H, 7.53; N, 6.93. Found: C, 77.14; H, 7.82; N, 6.88.

Example 33

2-{4-[2-(3-Aminophenyl)ethyl] phenylamino}benzoic acid. mp 182–184° C.

MS: 333 (M$^+$1$^+$). Analysis for C$_{21}$H$_{20}$N$_2$O$_2$.0.25 H$_2$O: Calcd: C, 74.87; H, 6.13; N, 8.43. Found: C, 74.86; H, 6.16; N, 8.32.

Example 34

2-{4-[3-(4-Dimethylaminophenyl)propyl] phenylamino}benzoic acid

MS: 375 (M$^+$1$^+$). Analysis for C$_{24}$H$_{26}$N$_2$O$_2$.0.1 H$_2$O: Calcd: C, 76.61; H, 7.02; N, 7.44. Found: C, 76.52; H, 7.22; N, 7.49.

Example 35

2-{4-[2-(4-Acetylaminophenyl)ethyl] phenylamino}benzoic acid. mp 224° C.

MS: 375 (M$^+$1$^+$).

Example 36

2-{4-[2-(3-Acetylaminopheny)ethyl] phenylamino}benzoic acid. mp 213–215° C.

MS: 375 (M$^+$1$^+$).

Example 37

2-{4-[2-(3-Dipropylaminophenyl)ethyl]
phenylamino}benzoic acid monohydrochloride. mp
189–193° C.

MS: 417 (M$^+$1$^+$). Analysis for $C_{27}H_{32}N_2O_2$·HCl: Calcd:
C, 71.58; H, 7.34; N, 6.18; Cl, 7.83. Found: C, 71.48; H,
7.35; N, 6.10; Cl, 7.66.

Example 38

2-{4-[2-(3-Dibutylaminophenyl)ethyl]
phenylamino}benzoic acid monohydrochloride. mp
175–180° C.

MS: 445 (M$^+$). Analysis for $C_{29}H_{36}N_2O_2$·HCl: Calcd: C,
72.40; H, 7.75; N, 5.82; Cl, 7.37. Found: C, 72.61; H, 7.95;
N, 5.78; Cl, 7.23.

Example 39

2-{4-[3-(4-Acetylaminophenyl)propyl]
phenylamino}benzoic acid. mp 176–178° C.

MS: 389 (M$^+$1$^+$).

Example 40

2-{4-[3-(3-Acetylaminophenyl)propyl]
phenylamino}benzoic acid. mp 140–145° C.

MS: 389 (M$^+$1$^+$).

Example 41

2-{4-[2-(3-Diethylaminophenyl)ethyl]
phenylamino}benzoic acid monohydrochloride. mp
166–171° C.

MS: 389 (M$^+$1$^+$). Analysis for $C_{25}H_{28}N_2O_2$·HCl: Calcd:
C, 70.66; H, 6.88; N, 6.59; Cl, 8.34. Found: C, 70.48; H,
6.89; N, 6.57; Cl, 18.39.

Example 42

2-{4-[2-(3-Piperidin-1-ylphenyl)ethyl]
phenylamino}benzoic acid monohydrochloride. mp
187–193° C.

MS: 401 (M$^+$1$^+$). Analysis for $C_{26}H_{28}N_2O_2$·HCl: Calcd:
C, 71.46; H, 6.69; N, 6.41; Cl, 8.11. Found: C, 71.28; H,
6.73; N, 6.35; Cl, 8.30.

Example 43

2-{4-[3-(4-Dipropylaminophenyl)propyl]
phenylamino}benzoic acid

MS: 431 (M$^+$1$^+$). Analysis for $C_{28}H_{34}N_2O_2$: Calcd: C,
78.10; H, 7.96; N, 6.51. Found: C, 77.91; H, 8.03; N, 6.43.

Example 44

2-{4-[3-(4-Dibutylaminophenyl)propyl]
phenylanino}benzoic acid

MS: 459 (M$^+$1$^+$). Analysis for $C_{30}H_{38}N_2O_2$: Calcd: C,
78.56; H, 8.35; N, 6.11. Found: C, 78.40; H, 8.50; N, 6.19.

Example 45

2-{4-[3-(3-Dibutylaminophenyl)propyl]
phenylamino}benzoic acid

MS: 459 (M$^+$1$^+$). Analysis for $C_{30}H_{38}N_2O_2$: Calcd: C,
78.56; H, 8.35; N, 6.11. Found: C, 78.40; H, 8.43; N, 6.11.

Example 46

2-(4-{3-[4-(1H-Pyrrol-1-yl)phenyl]
propyl}phenylamino)benzoic acid. mp 131–136° C.

MS: 397 (M$^+$1$^+$). Analysis for $C_{26}H_{24}N_2O_2$·0.2 $H_2O$:
Calcd: C, 78.05; H, 6.15; N, 7.00. Found: C, 77.95; H, 6.17;
N, 7.08.

Example 47

2-{4-[3-(4-Piperidin-1-ylphenyl)propyl]
phenylamino}benzoic acid

MS: 415 (M$^+$1$^+$). Analysis for $C_{27}H_{30}N_2O_2$·0.2 $H_2O$:
Calcd: C, 77.55; H, 7.33; N, 6.70. Found: C, 77.37; H, 7.35;
N, 6.63.

Example 48

2-{4-[3-(4-Diethylcarbamoylphenyl)propyl]
phenylamino}benzoic acid. mp 57–62° C.

MS: 431 (M$^+$1$^+$). Analysis for $C_{27}H_{30}N_2O_3$·0.3 $H_2O$:
Calcd: C, 74.39; H, 7.07; N, 6.43. Found: C, 74.23; H, 6.97;
N, 6.27.

Example 49

2-{4-[3-(4-Carboxyphenyl)propyl]
phenylamino}benzoic acid. mp 236–239° C.

MS: 375 (M$^+$).

Example 50

2-{4-[3-(4-Diethylaminomethylphenyl)propyl]
phenylamino}benzoic acid. mp 137° C.

MS: 417 (M$^+$1$^+$).

Example 51

2-{4-[3-(4-Propylaminophenyl)propyl]
phenylamino}benzoic acid

MS: 389 (M$^+$1$^+$). Analysis for $C_{25}H_{28}N_2O_2$·0.2 $H_2O$:
Calcd: C, 76.58; H, 7.30; N, 7.14. Found: C, 76.61; H, 7.29;
N, 7.03.

Example 52

2-{4-[3-(3-Propylaminophenyl)propyl]
phenylamino}benzoic acid

MS: 389 (M$^+$1$^+$). Analysis for $C_{25}H_{28}N_2O_2O_2$·0.1 $H_2O$:
Calcd: C, 76.93; H, 7.28; N, 7.18. Found: C, 76.85; H, 7.44;
N, 7.06.

Example 53

2-{4-[3-(4-Pyrrolidin-1-yl-phenyl)-propyl]-
phenylamino}-benzoic acid. mp 171–177° C.

MS: 401 (M$^+$1$^+$). Analysis for $C_{26}H_{28}N_2O_2$·0.2 $H_2O$:
Calcd: C, 77.27; H, 7.08; N, 6.93. Found: C, 77.09; H, 6.97;
N, 6.96.

Example 54

2-{4-[3-(3-Piperidin-1yl-phenyl)-propyl]-
phenylamino}-benzoic acid. mp 59–61° C.

MS: 415 (M$^+$1$^+$). Analysis for $C_{27}H_{30}N_2O_2$·0.3 $H_2O$:
Calcd: C, 77.22; H, 7.34; N, 6.67. Found: C, 77.18; H, 7.25;
N, 6.49.

Example 55

{5-[(1-Butyl-1,2,3,4-tetrahydro-6-quinolyl)methylidene]-4-oxo-2-thioxothiazolidin-3-yl}acetic acid. mp 222–224° C.

MS: 391 (M$^+$1$^+$).

Example 56

{5-[(1-Butyl-2,3-dihydro-1H-indol-5-yl)methylidene]-4-oxo-2-thioxothiazolidin-3-yl}acetic acid. mp>250° C.

MS: 377 (M$^+$1$^+$). Analysis for $C_{18}H_{20}N_2O_3S_2.0.4\ H_2O$: Calcd: C, 56.34; H, 5.46; N, 7.30; S, 16.71. Found: C, 56.27; H, 5.18; N, 7.31; S, 16.74.

Example 57

3-{5-[(1-Butyl-1,2,3,4-tetrahydroquinolin-6-yl)methylidene]-4-oxo-2-thioxo-thiazolidin-3-yl)propanoic acid. mp 214–215° C.

MS: 405 (M$^+$1$^+$).

Example 58

4-{5-[(1-Butyl-1,2,3,4-tetrahydroquinolin-6-yl)methylidene]-4oxo-2-thioxo-thiazolidin-3-yl)butanoic acid. mp 152–154° C.

MS: 417 (M$^-$1$^+$), 418 (M$^+$), 419 (M$^+$1$^+$). Analysis for $C_{21}H_{26}N_2O_3S_2.0.2\ H_2O$: Calcd: C, 59.74; H, 6.30; N, 6.64; S, 15.19. Found: C, 59.59; H, 6.16; N, 6.52; S, 15.38.

Example 59

2-{4-[3-(3,4-Dichloro-phenyl)propyl]phenylamino}-5-methyl-benzoic acid. mp 98–99° C.

MS: 414 (M$^+$).

Example 60

N-(2-{4-[3-(3,4-Dichloro-phenyl)-propyl]-phenylamino}-benzoyl)-methanesulfonamide was prepared by reacting the product from Example 9 with methanesulfonamide. mp 53–61° C.

Analysis for $C_{23}H_{22}Cl_2N_2O_3S.0.13\ H_2O$: Calcd: C, 57.58; H, 4.68; N, 5.84. Found: C, 57.20; H, 4.66; N, 5.51.

Example 61

2-{4-[2-(3,4-Dimethyl-phenyl)-ethyl]-phenylamino}-5-nitro-benzoic acid. mp 214–216° C.

Analysis for $C_{23}H_{22}N_2O_4.0.25\ H_2O$: Calcd: C, 69.99; H, 5.74; N, 7.18. Found: C, 69.90; H, 5.82; N, 6.81.

Example 62

2-[4-(2-Biphenyl-4-yl-ethyl)phenylamino]-5-nitro-benzoic acid. mp 239–244° C.

MS: 439 (MH$^+$).

Example 63

2-{4-[2-Chloro-3-trifluoromethyl-phenyl)-ethyl]-phenylamino}-5-nitro-benzoic acid. mp 207–209° C.

Analysis for $C_{22}H_{16}ClF_3N_2O_4$: Calcd: C, 56.85; H, 3.47; N, 6.03. Found: C, 56.75; H, 3.71; N, 5.83.

Example 64

5-Amino-2-{4-[2-(3,4-Dichloro-phenyl)-ethyl]-phenylamino}-benzoic acid was prepared by reacting the product from Example 2 with hydrogen gas in the presence of Raney nickel. mp 137–142° C.

Analysis for $C_{21}H_{18}Cl_2N_2O_2.0.96\ mol\ THF$: Calcd: C, 63.94; H, 4.72; N, 6.00. Found: C, 64.33; H, 4.91; N, 6.35.

Example 65

5-Nitro-2-(4-phenethyl-phenylamino)-benzoic acid. mp 198–202° C.

Analysis for $C_{21}H_{18}N_2O_4.0.11\ H_2O$: Calcd: C, 69.22; H, 5.04; N, 7.69. Found: C, 69.59; H, 5.27; N, 7.22.

Example 66

2-{4-[2-(4-Fluoro-3-trifluoromethyl-phenyl)-ethyl]-phenylamino}-benzoic acid. mp 148–150° C.

Analysis for $C_{22}H_{17}F_4NO_2$: Calcd: C, 65.51; H, 4.25; N, 3.47. Found: C, 65.51; H, 4.13; N, 3.46.

Example 67

2-{4-[2-(3,4-Difluoro-phenyl)-ethyl]-phenylamino}-5-nitro-benzoic acid mp 203–208° C.

Analysis for $C_{21}H_{16}F_2N_2O_4$: Calcd: C, 63.32; H, 4.05; N, 7.03. Found: C, 62.94; H, 4.37; N, 6.87.

Example 68

{4-[2-(3,4-Dichloro-phenyl)-ethyl]-phenyl}-[2-(1H-tetrazol-5-yl)phenyl]-amine was prepared as described in Example 1, using a tetrazole fluoro intermediate that was synthesized from commercially available 2-fluorobenzonitrile and sodium azide under standard reaction conditions. mp 129 shrink, 152–157° C.

Analysis for $C_{21}H_{17}Cl_2N_5.0.15\ EtOAc.0.15\ Hexane$: Calcd: C, 61.80; H, 4.64; N, 16.12. Found: C, 61.61; H, 4.28; N, 15.83.

Example 69

2-{4-[2-(4-Fluoro-3-trifluoromethyl-phenyl)-ethyl]-phenylamino}-5-nitro-benzoic acid. mp 190–193° C.

Analysis for $C_{22}H_{16}F_4N_2O_4$: Calcd: C, 58.93; H, 3.60; N, 6.25. Found: C, 58.69; H, 3.42; N, 6.57.

Example 70

2-(4-Phenethyl-phenylamino)-benzoic acid. mp 173–182° C.

Analysis for $C_{21}H_{19}NO_2$: Calcd: C, 79.47; H, 6.03; N, 4.41. Found: C, 79.42; H, 5.97; N, 4.47. Found: C, 79.59; H, 6.03; N, 4.50.

Example 71

2-{4-[2-(3,4-Dichloro-phenyl)-ethyl]-phenylamino}-5-fluoro-benzoic acid. mp 180–182° C.

Analysis for $C_{21}H_{16}Cl_2FNO_2.0.06\ H_2O$: Calcd: C, 62.23; H, 4.01; N, 3.46. Found: C, 61.83; H, 4.04; N, 3.29.

Example 72

2-{4-[2-(3,4-Dichloro-phenyl)-ethyl]-phenylamino}-nicotinic acid. mp 168–171° C.

Analysis for $C_{20}H_{16}Cl_2N_2O_2$: Calcd: C, 62.03; H, 4.16; N, 7.23. Found: C, 62.11; H, 4.17; N, 7.07.

Example 73

2-{4-[2-(3-Chloro-phenyl)-ethyl]-phenylamino}-5-nitro-benzoic acid. mp 192.5–194.5° C.

Analysis for $C_{21}H_{17}ClN_2O_4$: Calcd: C, 63.56; H, 4.32; N, 7.06. Found: C, 63.83; H, 4.62; N, 6.79.

Example 74

2-{4-[2-(4-Chloro-phenyl)-ethyl]-phenylamino}-5-nitro-benzoic acid. mp 210–212° C.

Analysis for $C_{21}H_{17}ClN_2O_4 \cdot 0.26 \, H_2O$: Calcd: C, 62.82; H, 4.40; N, 6.98. Found: C, 62.51; H, 4.34; N, 6.58.

Example 75

2-{4-[2-(3,4-Dichloro-phenyl)-ethyl]-phenylamino}-5-methyl-benzoic acid. mp 153–160° C.

Analysis for $C_{22}H_{19}Cl_2NO_2 \cdot 0.61 \, H_2O$: Calcd: C, 64.25; H, 4.96; N, 3.41. Found: C, 63.87; H, 4.64; N, 3.55.

Example 76

2-{4-[2-(2-Chloro-phenyl)-ethyl]-phenylamino}-5-nitrobenzoic acid. mp 236–238° C.

Example 77

2-{4-[2-(2,4-Dichloro-phenyl)-ethyl]-phenylamino}-5-nitro-benzoic acid. mp 200.5–202.5° C.

Analysis for $C_{21}H_{16}Cl_2N_2O_4$: Calcd: C, 58.49; H, 3.74; N, 6.50. Found: C, 58.33; H, 3.67; N, 6.29.

Example 78

2-{4-[2-(3,4-Dichloro-phenyl)-ethyl]-phenylamino}-6-trifluoromethyl-benzoic acid. mp 130–132° C.

Analysis for $C_{22}H_{16}Cl_2F_3NO_2$: Calcd: C, 58.17; H, 3.55; N, 3.08. Found: C, 58.25; H, 3.65; N, 3.05.

Example 79

2-{4-[2-(4-Dibutylamino-phenyl)-ethyl]-phenylamino}-5-nitro-benzoic acid. mp>260° C.

Example 80

2-{4-[2-(3,4-Dichloro-phenyl)-ethyl]-phenylamino}-5-dimethylamino-benzoic acid. mp 75–80° C.

Example 81

2-{4-[2-(3,5-Dichloro-phenyl)-ethyl]-phenylamino}-benzoic acid. mp 191–194° C.

Analysis for $C_{21}H_{17}Cl_2NO_2$: Calcd: C, 65.30; H, 4.44; N, 3.63. Found: C, 65.38; H, 4.29; N, 3.52.

Example 82

2(4-{2-[(4aS,8aR)-4-(Octahydro-isoquinolin-2-yl)-phenyl]-ethyl}-phenylamino)-benzoic acid was prepared according to Example 1 using a decahydroisoquinoline aldehyde which was prepared from trans-decahydroisoquinoline and para-fluorobenzaldehyde under standard reaction conditions mp 203–206° C.

Analysis for $C_{30}H_{34}N_2O_2 \cdot 0.12 \, H_2O$: Calcd: C, 78.89; H, 7.56; N, 6.13. Found: C, 78.49; H, 7.58; N, 5.90.

The following examples are prepared according to the foregoing methods, or by utilizing standard combinatorial synthetic methodology by reacting halo substituted benzoate esters with a substituted aniline to form the corresponding diarylamine, followed by saponification to the benzoic acid of Formula I. The reactions are carried out on 0.15 mmol scale as follows. Solutions of each halo benzoate reactant (0.18 M) in toluene are placed in 2 dram reaction vials. Each aniline reactant is dissolved in anhydrous toluene to give 0.15 M solutions. A Distriman pipet is used to add 1 mL (0.15 mmol, 1 eq) of each halo benzoate solution to the appropriate vials containing 1 mL (0.18 mmol, 1.2 eq) of the aniline reactants. A catalyst solution is prepared by dissolving 0.025 M of $Pd_2(dba)_3$ (dipalladium-tridibenzylidene acetone) and 0.075 M of BINAP (2,2'-bis (diphenylphosphino)-1,1'-binapthyl) in toluene, and 0.25 mL of the catalyst solution is added to each reaction vial. A base, generally cesium carbonate (68 mg, 0.21 mmol, 1.40 eq) is added to each reaction vial, and the vials are capped and placed in a shaker oven and heated at 100° C. for 48 hours. The reaction mixtures are then cooled, and the reaction solvents are removed by evaporation. The solid residue is suspended in 400 µL of ethyl acetate and filtered to remove all catalyst. The filtrates are concentrated to dryness by evaporation to provide compounds of Formula I, wherein the benzoic acid portion is esterified (e.g., benzyl or methyl ester). The esters are dissolved in 500 µL of THF/ethanol (1:1 v/v) to which is added 300 µL of 5 M sodium hydroxide. The solutions are shaken for 5 hours at 60° C. and then cooled and concentrated to dryness by evaporation of the solvents to provide the desired compounds of Formula I. Typical compounds prepared by this method are as follows. The structure of the compounds are generally confirmed by mass spectral analysis.

Example 83

2-(3',5'-Dichloro-3-methyl-biphenyl-4-ylamino)-benzoic acid

MS: 371; MW: 372.2495.

Example 84

2-(3',5'-Dibromo-3-methyl-biphenyl-4-ylamino)-
benzoic acid

MS: 459; MW: 461.1515.

Example 85

2-(4-1,3-Benzodioxol-5-yl-2-methyl-phenylamino)-
benzoic acid

MS: 347; MW: 347.3683.

Example 86

2-(2,2',4'-Trichloro-biphenyl-4-ylamino)-benzoic
acid

MS: 391; MW: 392.6678.

Example 87

2-(2-Chloro-3',4'-difluoro-biphenyl-4-ylamino)-
benzoic acid

MS: 359; MW: 359.7578.

Example 88

2-(3'-Bromo-2-chloro-biphenyl-4-ylamino)-benzoic
acid

MS: 401; MW: 402.6737.

Example 89

2-{4-[2-(3,4-Dichloro-phenyl)-ethyl]-phenylamino}-
5-nitrobenzoic acid

Example 90

2-{4-[2-(3,4-Dichloro-phenyl)-ethyl]-phenylamino}-
3-nitrobenzoic acid

Example 91

3-{4-[2-(3,4-Dichloro-phenyl)-ethyl]-phenylamino}-
benzoic acid

Example 92

5-{4-[2-(3,4-Dichloro-phenyl)-ethyl]-phenylamino}-
isophthalic acid

Example 93

2-{4-[2-(3,4-Dichloro-phenyl)-ethyl]-phenylamino}-
benzoic acid

Example 94

2-{4-[2-(3,4-Dichloro-phenyl)-ethyl]-phenylamino}-
4,5-dimethoxy-benzoic acid

Example 95

2-{4-[2-(3-Chloro-4-methyl-phenyl)-ethyl]-
phenylamino}-3-nitro-benzoic acid

Example 96

3-{4-[2-(3-Chloro-4-methyl-phenyl)-ethyl]-
phenylamino}-benzoic acid

Example 97

5-{4-[2-(3-Chloro-4-methyl-phenyl)-ethyl]-
phenylamino}-isophthalic acid

Example 98

2-{4-[2-(3-Chloro-4-methyl-phenyl)-ethyl]-
phenylamino}-benzoic acid

Example 99

4-(4-{2-[(4aS,8aR)-4-(Octahydro-isoquinolin-2-yl)-
phenyl]-ethyl}-phenylamino)-benzoic acid

Example 100

2-{4-[3-(4-Diethylamino-phenyl)propyl]-
phenylamino}-5-methoxy-benzoic acid

Example 101

2-{4-[2-(3-Methoxy-phenyl)-ethyl]-phenylamino}-
benzoic acid

Example 102

2-{4-[2-(3-Bromo-phenyl)-ethyl]-phenylamino}-
benzoic acid

Example 103

2-{4-[2-(3-Fluoro-phenyl)-ethyl]-phenylamino}-benzoic acid

Example 104

2-{4-[2-(3,4-Dichloro-phenyl)-ethyl]-phenylamino}-5-methoxy-benzoic acid

Example 105

4-{4-[2-(3,4-Dichloro-phenyl)-ethyl]-phenylamino}-nicotinic acid

Example 106

2-[2-(4-Fluoro-3-trifluoromethyl-phenyl)-2,3dihydro-1H-isoindol-5-ylamino]-benzoic acid

Example 107

2-{4-[2-(3-Fluoro-4-methyl-phenyl)-ethyl]-phenylamino}-benzoic acid

Example 108

2-{4-[3-(4-Diethylamino-phenyl)-propyl]-phenylamino}-5-nitro-benzoic acid

Example 109

4-{4-[3-(4-Diethylamino-phenyl)-propyl]-phenylamino}-benzoic acid

Example 110

4-{4-[3-(4-Diethylamino-phenyl)-propyl]-phenylamino}-3-methoxy-6-nitro-benzoic acid

Example 111

4-{4-[3-(4-Diethylamino-phenyl)-propyl]-phenylamino}-3-methoxy-benzoic acid

Example 112

2-{4-[2-(3-Chloro-4-methyl-phenyl)-ethyl]-phenylamino}-5-methoxy-benzoic acid

Example 113

{4-[2-(3-Chloro-4-methyl-phenyl)-ethyl]-phenyl}-(2-methoxy-5-nitro-phenyl)-amine

Example 114

2-{4-[3-(4-Diethylamino-phenyl)-propyl]-phenylamino}-3-nitro-benzoic acid

Example 115

3-{4-[3-(4-Diethylamino-phenyl)-propyl]-phenylamino}-benzoic acid

Example 116

2-{4-[2-(3,4-Dimethoxy-phenyl)-ethyl]-phenylamino}-benzoic acid; mp 159–161° C.

Example 117

2-{4-[2-(3,4-Dichloro-phenyl)-ethyl]-phenylamino}-benzoic acid monosodium; mp 107–108° C.

Example 118

2-{4-[2-(3,4-Dichloro-phenyl)-ethyl]-phenylamino}-benzoic acid monopotassium; mp>200° C.

Example 119

2-{4-[2-(3,4-Dichloro-phenyl)-ethyl]-phenylamino}-benzoic acid calcium salt (1:1); mp>220° C.

Example 120

2-{4-[2-(3,4-Dichloro-phenyl)-ethyl]-phenylamino}-benzoate-2-hydroxy-1,1-bis hydroxymethyl-ethyl-ammonium; mp 185–187° C.

Example 121

2-{4-[4-(3,4-Dichloro-phenyl)-butyl]-phenylamino}-5-methoxy-benzoic acid; mp 155–158° C.

Example 122

2-{4-[2-(3,4-Difluoro-phenyl)-ethyl]-phenylamino}-benzoic acid; mp 184–185° C.

Example 123

2-{3-[2-(4-Chloro-phenyl)-ethyl]-phenylamino}-benzoic acid; mp 155–157° C.

Example 124

2-{3-[2-(3,4-Dimethyl-phenyl)-ethyl]-phenylamino}-benzoic acid; mp 182–184° C.

Example 125

2-{4-[2-(2,4-Dimethoxy-phenyl)-ethyl]-phenylamino}-benzoic acid; mp 180–181° C.

Example 126

2-{4-[2-(2-Chloro-phenyl)-ethyl]-phenylamino}-benzoic acid; mp 140–143° C.

Example 127

2-{4-[2-(2-Hydroxy-phenyl)-ethyl]-phenylamino}-benzoic acid; mp 218–219° C.

Example 128

2-{4-[2-(3-Chloro-phenyl)-ethyl]-phenylamino}-benzoic acid; mp 152–154° C.

Example 129

2-[4-(2-Biphenyl-4-yl-ethyl)-phenylamino]-benzoic acid; mp 200–202° C.

Example 130

2-{4-[2-(2,4-Dichloro-phenyl)-ethyl]-phenylamino}-benzoic acid; mp 181–183° C.

Example 131

3-{4-[2-(3,4-Dichloro-phenyl)-ethyl]-phenylamino}-benzoic acid; mp 137–138° C.

Example 132

4-{4-[2-(3,4-Dichloro-phenyl)-ethyl]-phenylamino}-benzoic acid; mp 214–215° C.

Example 133

2-{4-[2-(3,4,5-Trimethoxy-phenyl)-ethyl]-phenylamino}-benzoic acid; mp 146–147° C.

Example 134

2-{4-[2-(4-Phenoxy-phenyl)-ethyl]-phenylamino}-benzoic acid; mp 153–154° C.

Example 135

2-{4-[5-(3,4-Dichloro-phenyl)-pentyl]-phenylamino}-benzoic acid; mp 106–108° C.

Example 136

2-{4-[2-(4-{2-Hydroxycarbonylphenylamino}phenyl)ethyl]-phenylamino}-benzoic acid; MS 451 ($M^{-1}$).

Example 137

2-(3',5'-Dichloro-biphenyl-4-ylamino)-benzoic acid; mp>220° C.

Example 138

4-{4-[3-(3,4-Dichloro-phenyl)propyl]-phenylamino}-2-methoxy-5-nitro-benzoic acid; mp 74–78° C.

Example 139

2-{4-[3-(3,4-Dichloro-phenyl)-propyl]-phenylamino}-5-fluoro-benzoic acid; mp 122–123° C.

Example 140

5-Amino-2-{4-[5-(3,4-dichloro-phenyl)pentyl]-phenylamino}-benzoic acid; mp 182–184° C.

Example 141

N-(2-{4-[3-(3,4-Dichloro-phenyl)-propyl]-phenylamino}-benzoyl)-C,C,C,-trifluoro-methanesulfonamide; MS 531 ($M^-$).

Example 142

N-(2-{4-[3-(3,4-Dichloro-phenyl)propyl]-phenylamino}-benzoyl)-benzenesulfonamide; MS 539.

Example 143

2-{4-[2-(3,4-Dichlorophenyl)-ethyl]-phenylamino}-5-trifuoromethyl-benzoic acid; mp 190–192° C. MS 453 (M$^{-1}$).

Example 144

4-{4-[2-(3,4-Dichloro-phenyl)-ethyl]-phenylamino}-isophthalic acid; mp 264–266° C.

Example 145

2-{4-[2-(3,4-Dichloro-phenyl)-ethyl]-phenylamino}-4-trifluoromethyl-benzoic acid; mp 134–136° C.; MS 454 (M$^+$).

Example 146

2-{4-[2-(3,4-Dichloro-phenyl)-ethyl]-phenylamino}-3-trifluoromethyl-benzoic acid; MS 454 (M$^+$).

Example 147

2-({4-[2-(3,4-Dichloro-phenyl)-ethyl]-phenyl}-methyl-amino)-5-dimethylamino-benzoic acid; mp 128–131° C.

Example 148

2-({4-[2-(3,4-Dichloro-phenyl)-ethyl]-phenyl}-methyl-amino)-benzoic acid; MS 400 (M$^+$).

Example 149

2-{4-[2-(3,4-Dichlorophenyl)-ethyl]-phenylamino}-5-dipropylamino-benzoic acid; MS 485 (M$^+$).

Example 150

5-Dibutylamino-2-{4-[2-(3,4-dichloro-phenyl)-ethyl]-phenylamino}-benzoic acid; MS 513 (M$^+$).

Example 151

2-{4-[2-(3,4-Dichloro-phenyl)-ethyl]-phenylamino}-5-diethylamino-benzoic acid; mp 106–110° C.

Example 152

2,2'-[1,2-Ethanediylbis(4,1-phenyleneimino)]bis-benzoic acid

Example 153

4-[3-[4-Diethylamino)phenyl]propyl]-N-(2-methoxy-5-nitrophenyl)-benzinamine

Example 154

2-{3-[2-(4-Chlorophenyl)ethyl]phenylamino}-benzoic acid

Example 155

2-{3-[3-(3,4-Dichlorophenyl)propyl]phenylamino}-benzoic acid

Example 156

2-{3-[3-(4-Diethylaminophenyl)propyl]phenylamino}-benzoic acid

Example 157

2-{3-[3-(4-Di-n-propylaminophenyl)propyl]phenylamino}-benzoic acid

The following Examples 158–163 illustrate the use of invention compounds as starting materials and intermediates in the synthesis of other invention compounds and derivatives. The examples illustrate reduction of nitro groups to amino groups, alkylation of amino group, and esterification of carboxylic acid groups. These reactions are depicted in the following generalized Scheme 12.

Scheme 12

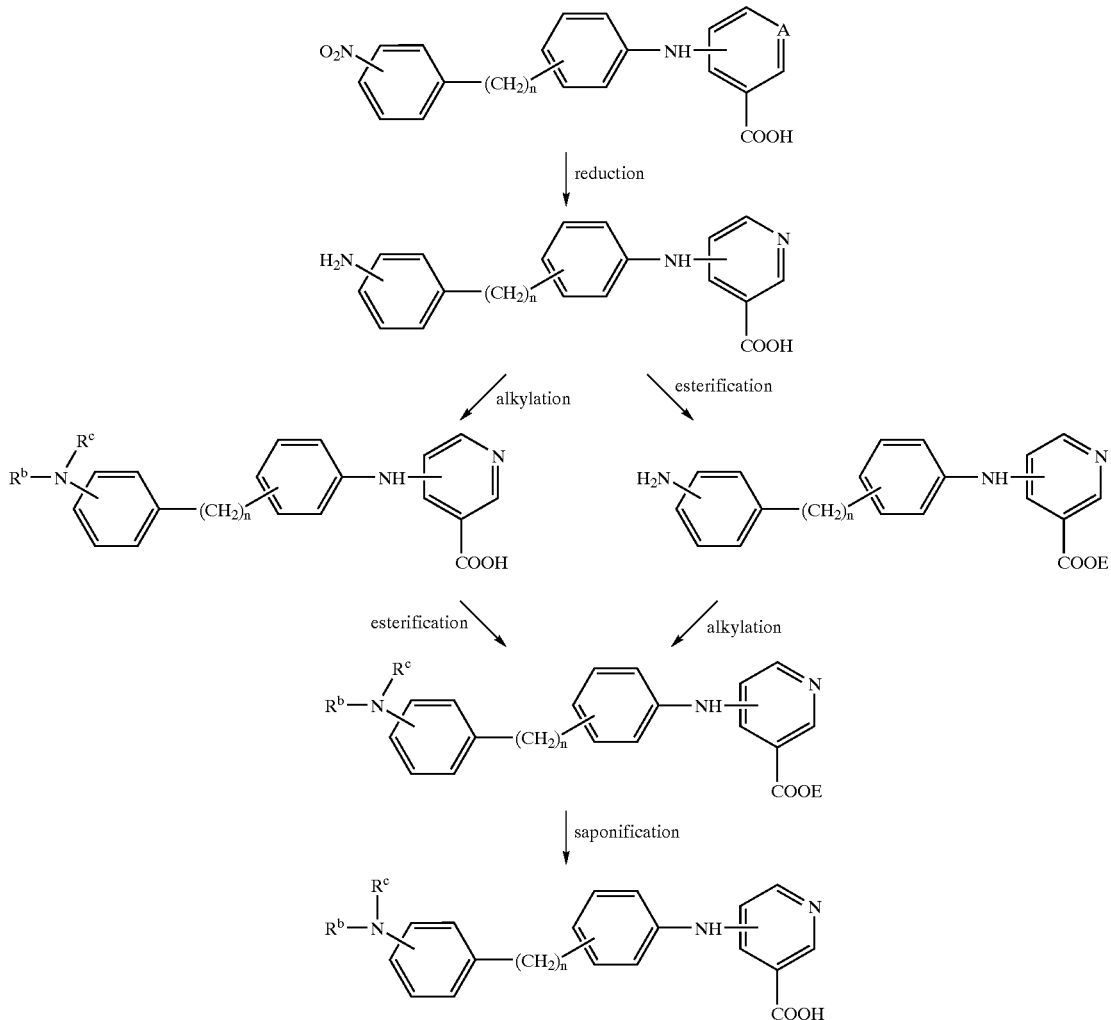

where $R^b$ and $R^c$ are as defined above, and E is an ester forming group such as $C_1$–$C_6$ alkyl (e.g., methyl, 2,2,2-trichloroethyl), benzyl, diphenylmethyl, or the like.

Example 158

2-{4-[3-(4-Nitrophenyl)propyl]phenylamino}benzoic acid

To a slurry of 4-[3-(4-nitrophenyl)propyl]aniline (4.08 g, 15.9 mmol) and 2-bromobenzoic acid (3.52 g, 17.5 mmol) in i-PrOH (100 mL) was added Cu(OAc)$_2$ (87 mg, 0.478 mmol) and KOAc (3.44 g, 35.0 mmol) at room temperature. The resulting mixture was allowed to heat under reflux for 23 hours, then cooled to room temperature. After removing the solvent under reduced pressure, the residue was diluted with water (100 mL) and basified with aqueous 1.0 M-NaOH solution to pH 9.0. The aqueous layer was washed with Et$_2$O (20 ml, twice) and acidified with aqueous 1.0 M-HCl solution to pH 3.0. The precipitate formed was filtered by suction and dried at 60° C. in vacuo, affording the title compound as a beige solid (5.75 g, 96% yield). mp 150–153° C. MS (Fab): 376 (MH$^+$).

Example 159

2-{4-[3-(4-Aminophenyl)propyl]phenylamino}benzoic acid

To a solution of 2-{4-[3-(4-nitrophenyl)propyl]phenylamino}benzoic acid (Example 158) (3.0 g, 7.97 mmol) in DMF (40 mL) was added 10% Pd—C (300 mg) at room temperature under argon atmosphere. Hydrogen gas (1 atm) was introduced into the flask and the mixture was stirred for 14 hours at room temperature. The reaction mixture was filtered through a Celite pad to remove Pd—C and concentrated in vacuo. The residue was diluted with MeOH (ca. 50 mL) and concentrated in vacuo. This operation was repeated 3 times to remove any trace of DMF. The residue was diluted with McOH again, and insoluble stuff was removed by filtration. Removing the solvent of the filtrate in vacuo afforded an oil, which was diluted with CH$_3$CN (50 mL) and added dropwise water (100 mL) slowly. The precipitate formed was filtered and dried at 60° C. in vacuo, affording the title compound as a white solid (2.34 g, 85% yield). mp 110–112° C. MS (Fab): 347 (MH$^+$).

Example 160

2-{4-[3-(4-Aminophenyl)propyl] phenylamino}benzoic acid methyl ester

To a solution of 2-{4-[3-(4-aminophenyl)propyl] phenylamino}benzoic acid (Example 159) (2.34 g, 6.75 mmol) in MeOH (50 mL) was added concentrated $H_2SO_4$ (1.0 mL) at room temperature. The mixture was stirred under reflux for 3.0 days. The reaction was quenched with $Et_3N$ (10 mL) at 5° C., and the solvent was removed under reduced pressure. The residue was diluted with water (20 mL) and extracted with $Et_2O$ (20 mL, 4 times). The combined ether layer was washed with water (10 mL) and brine (10 mL), and dried over anhydrous $Na_2SO_4$. The solvent was removed under reduced pressure and purification by column chromatography afforded crude title compound as a yellow amorphous material (2.59 g). This material was used without further purification.

Example 161

2-{4-[3-(4-Diethylaminophenyl)propyl] phenylamino}benzoic acid methyl ester and 2-{4-[3-(4-Ethylaminophenyl)propyl] phenylamino}benzoic acid methyl ester To a solution of the crude ester described above (2.59 g, ca. 6.75 mmol) and $CH_3CHO$ (2.0 mL, 35.1 mmol) in $CH_3CN$ (50 mL) was added $NaBH_3CN$ (1.70 g, 27.0 mmol) at 5° C., and the suspension was stirred for 30 minutes while the pH was monitored and aqueous 1.0 M-HCl solution was added to maintain the mixture moderately acidic (pH 3.0–4.0). The reaction mixture was allowed to warm up to room temperature over 1.0 hour and then basified with aqueous 1.0 M-NaOH solution to pH 9.0. The reaction mixture was concentrated under reduced pressure to remove $CH_3CN$, and the resulting aqueous solution was acidified with aqueous 1.0 M-HCl solution to pH 3.0. The aqueous solution was extracted with $CHCl_3$ (20 mL, 3 times), and the combined extract was washed with brine (5 mL). After drying over anhydrous $Na_2SO_4$, the solvent was removed under reduced pressure and purified by column chromatography (silica gel 60N, n-hexane/$CHCl_3$/$Et_3N$ 50:98:2). First eluted was the dialkylated product as a yellow amorphous material (1.07 g, 38%).

MS (Fab): 417 ($MH^+$).

Subsequently eluted was the monoalkylated product as a yellow amorphous material (0.79 g, 30%).

MS (Fab): 389 ($MH^+$).

Example 162

2-{4-[3-(4-Diethylaminophenyl)propyl] phenylamino}benzoic acid

To an emulsion of 2-{4-[3-(4-diethylaminophenyl) propyl]phenylamino}-benzoic acid methyl ester (1.68 g, 4.03 mmol) in EtOH (50 mL) was added aqueous 3 M-KOH solution (4.0 mL, 12.0 mmol) at room temperature, then the mixture was allowed to heat under reflux for 40 minutes. The reaction mixture was cooled to room temperature and neutralized with aqueous 1.0 M-HCl solution to pH 9.0. The mixture was concentrated under reduced pressure to remove EtOH, and the resulting aqueous solution was extracted with $CHCl_3$ (50 mL, 3 times). The combined extract was washed with brine (10 mL) and dried over anhydrous $Na_2SO_4$. The solvent was removed under reduced pressure and purification by column chromatography (silica gel 60N, conc $NH_4OH/MeOH/CHCl_3$ 0.2:2:100 to 0.5:5:100) afforded a yellow oil. This oil was diluted with acetone, and the solution was concentrated under reduced pressure at room temperature to give the title compound as an amorphous solid (1.62 g, 99% for 0.2 hydrate).

MS (Fab) 403 ($MH^+$). Analysis for $C_{26}H_{30}N_2O_2 \cdot 0.20$ $H_2O$: Calcd: C, 76.89; H, 7.54; N, 6.90. Found: C, 76.73; H, 7.67; N, 7.10.

Example 163

2-{4-[3-(4-Ethylaminophenyl)propyl] phenylamino}benzoic acid

The title compound was prepared from 2-{4-[3-(4-ethylaminophenyl)-propyl]phenylamino}benzoic acid methyl ester (from Example 161), EtOH (10 mL), and 3 M-KOH solution (1.0 mL) using the procedure described in Example 162. This procedure yielded a yellow solid, 253 mg of the desired product (90% for 0.1 hydrate).

MS (Fab): 375 ($MH^+$). Analysis for $C_{24}H_{26}N_2O_2 \cdot 0.10$ $H_2O$: Calcd: C, 76.61; H, 7.02; N, 7.44. Found: C, 76.62; H, 7.06; N, 7.36.

Biological Examples

Representative compounds of Formula I have been evaluated in several in vitro and in vivo assays which are well-established as indicative of clinical usefulness in treating Alzheimer's disease.

Amyloid Assays

BASSR (Beta-Amyloid Self-Seeding Radioassay)

An assay for inhibitors of self-seeded amyloid fibril growth

Materials:

Stock Solutions:

Assay Buffer—50 mM sodium phosphate, pH 7.5, 100 mM NaCl, 0.02% $NaN_3$, 1 M urea (filter and store at 4° C.).

Soluble Aβ(1–40) peptide (Bachem, Torrance, Calif.)—2.2 mg/mL in deionized $H_2O$ (stored in aliquots at −20° C., keep on ice when thawed) will self-seed after 1 week storage. Typically, the solution should be stored until no lag phase is seen in the assay.

$^{125}$I-labeled Aβ(1–40)—150K–350K cpm/μL in 100% acetonitrile—0.1% trifluoroacetic acid (TFA)—1% β-mercaptoethanol (aliquots stored at −20° C.). $^{125}$I-labeled Aβ(1–40) can be made in accordance with the procedure set forth by H. LeVine, III in *Neurobiol. Aging*, 16, 755, (1995), which is hereby incorporated by reference, or this reagent may be purchased from Amersham, Arlington Heights, Ill.

Final assay conditions: 30 μM soluble Aβ(1–40) in deionized water in assay buffer+20K–50K cpm $^{125}$I-labeled Aβ(1–40) per assay. Compound to be tested is dissolved in dimethylsulfoxide (DMSO), typically 5 to 50 mM stock, such that the final concentration of DMSO is <1% v/v in the assay.

Assay: Reaction mixture for 50 assays (on ice) is comprised of 0.1 to 0.2 μL of $^{125}$I-labeled A$^{125}$I-labeled Aβ(1–40)+1 μL of soluble Aβ(1–40)+13.5 μL assay buffer per assay. The following are the amounts of the components of the reaction mixture sufficient for 50 assay wells:

5–10 μL $^{125}$I-labeled Aβ(1–40) dried down

675 μL assay buffer

50 μL soluble Aβ(1–40)

Assay Method

1) Prepare reaction mixture above by mixing components and storing on ice.

2) Pipet 14.5 µL of reaction mixture into each of 50 wells on a polypropylene U-bottom 96-well microtiter plate on ice. (Costar 3794).
3) Add 1.7 µL of diluted compound to be tested to each well in a column of eight, including solvent control. Serial 3-fold dilutions from 1 mM (100 µM final) in assay buffer–urea=7 dilutions+zero. Each 96-well plate can therefore accommodate 11 samples+1 Congo Red control (0.039–5 µM final in 2-fold steps).
4) Seal the plate with aluminum film (Beckman 538619) and incubate for 10 minutes on ice.
5) Raise the temperature to 37° C. and incubate for 3 to 5 hours (depending on the lot of the peptide).
6) Remove the aluminum film and add 200 µL/well of ice cold assay buffer with urea, collecting the radiolabeled fibrils by vacuum filtration through 0.2 µm pore size GVWP filters in 96-well plates (Millipore MAGV N22, Bedford, Mass.). Determine the radioactivity of the filters using standard methods well-known to those skilled in the art.

BASST (Beta-Amyloid Self-Seeding, Thioflavin T)

An assay for inhibitors of self-seeded amyloid fibril growth

Methods:

Materials:

Stock Solutions:

Assay Buffer—50 mM sodium phosphate, pH 7.5, 100 mM NaCl, 0.02% NaN$_3$, 1 M urea (filter and store at 4° C.)

Soluble Aβ(1–40)—2.2 mg/mL in deionized H$_2$O (store in aliquots at −20° C., keep on ice when thawed) will self-seed after 1 week storage. Typically, the solution should be stored until no lag phase is seen in the assay.

Final assay conditions: 30 µM soluble Aβ(1–40) in deionized water in assay buffer. Compound to be tested is dissolved in DMSO, typically 5 to 50 mM stock, such that the final concentration of DMSO is <1% v/v in the assay.

Assay: Reaction mixture for 50 assays (on ice) comprised of 1 µL of soluble Aβ(1–40)+13.5 µL assay buffer per assay. The following are the amounts of the components of the reaction mixture that result in each of the 50 assay wells:

50 µL soluble Aβ(1–40)

675 µL assay buffer

Assay Method

1) Prepare the reaction mix above by mixing the components and storing on ice.
2) Pipet 14.5 µL of reaction mixture into each of 50 wells of a polystyrene U-bottom 96-well microtiter plate (Corning 25881-96) on ice.
3) Add 1.7 µL of diluted compound to be tested to each well in a column of eight, including solvent control. Serial 3-fold dilutions from 1 mM (100 µM final) in assay buffer–urea=7 dilutions+zero. Each 96-well plate can therefore accommodate 11 samples+1 Congo Red control (0.039–5 µM final in 2-fold steps).
4) Seal the plate with aluminum film and incubate for 10 minutes on ice.
5) Raise the temperature to 37° C. and incubate for 3 to 5 hours (depends on the lot of the peptide).
6) Remove the aluminum film and add 250 µL/well of 5 µM thioflavin T (ThT) [T-3516, Sigma-Aldrich] in 50 mM glycine-NaOH, pH 8.5. Read fluorescence on a plate reader (ex=440 nm/20 nm; em=485 nm/20 nm) within 5 minutes.

BAPA (Beta-Amyloid Peptide Aggregation)

This assay is used to provide a measure of inhibition by a compound against the aggregation behavior of the beta amyloid peptide.

The purpose of this assays is to provide a higher volume method of assaying the amount of beta amyloid aggregation using an endpoint assay based on filtration. In this assay, hexafluoroisopropanol (HFIP) is used to break down the initial amyloid peptide to a monomer state and use a concentration of 33 µM which is high enough so that aggregation will occur at pH 6.0 in several hours.

Methods:

β-Amyloid Peptide Aggregation, DH 6.0 (BAPA)

In a 96-well plate (Costar 3794), we add 25 µL 50 mM Phosphate Buffer, pH 6.0, 10 µL 0.5 mg/mL Aβ (1–40) peptide in 20% HFIP+0.1 µL/assay radioiodinated $^{125}$I Aβ (1–40) [$^{125}$I Aβ(1–40)], and 1 µL of the compound to be tested starting at 50 mM with a concentration of DMSO <1%. Then, we incubate for 2 to 4 hours at room temperature. We stop the reaction with 200 µL of 50 mM phosphate buffer, pH 6.0, and filter it through a 0.2 µm 96-well filter plate (Millipore MAGU N22). We wash the filter plate with 100 µL of the same phosphate buffer. Aggregation was detected on a Microbeta counter after impregnating the filters with Meltilex (1450–441) and is corrected for background.

Batym Assay

Methods:

Required Aβ (1–42) (California Peptide) was dried from its hexafluoroisopropanol (HFIP) stock solution. The Aβ (1–42) was dissolved in dimethylsulfoxide (DMSO) and then mixed with phosphate buffered saline (PBS) (pH 7.4). The mixed Aβ (1–42) solution was filtered with a 0.2 µm Omnipore membrane syringe filter Millipore, Bedford, Mass.). The compound to be tested in DMSO (50 times concentrate) was put into each well (0.5 µL/well) of a 96-well plate. The Aβ (1–42) solution was added into each well (24.5 µL/well). The plate was centrifuged at 1,000 g for 5 minutes and incubated at 37° C. for 1 day (Aβ 1–42; final concentration 100 µM).

After incubation Thioflavin T (ThT) (30 µM) solution in glycine-NaOH buffer (pH 8.5, 50 mM) was added into each well (250 µL/well), fluorescence was measured (ex=440/20 nm, em=485/20 nm) using a fluorescence plate reader. The inhibitory activity was calculated as the reduction of fluorescence with the following formula:

Inhibition (%)={(F(Aβ)−F(Aβ+compound)}/{F(Aβ)−F(solvent+compound)}×100

The IC$_{50}$s were calculated by a curve fitting program using the following equation. The data were obtained from two different experiments in triplicate.

Inhibition(x)=100−100/{1+(x/IC$_{50}$)$^n$}, x=Concentration of tested compound (M),

IC$_{50}$=(A, n=Hill coefficient

Representative compounds of Formula I have exhibited inhibitory activities (IC$_{50}$) ranging from 0.1 µM to greater than 100 µM in the foregoing assays.

The results of these assays for specific and representative compounds of the present invention are shown in Table 1 below.

TABLE 1

β-Amyloid Inhibitory Activity of Compounds of Formula I

| Example No. | BASSR (IC$_{50}$ = μM) | BASST (IC$_{50}$ = μM) | BATYM (IC$_{50}$ = μM) | BAPA (IC$_{50}$ = μM) |
|---|---|---|---|---|
| 1 | 10 (P), >100 (P) (6x), >100 (Q), >100 (R), >100 (S), 52 (T) >100 (Z) | 2, 4, 30, 10 (P) 3 (Q) >100 (R) 11 (S), 11 (T) 6 (Z) | 50, 58.8 (P) 57.8 (Q) >60 (R), | 60 (P), >100 (P) 86 (Q), >60 (S), 11 (T) |
| 2 | 2.2, 4.1, 4.1, 12, 4.5 | 1, 1.5 (P) | 6.52 (P) | 70 (P) |
| 3 | 4.5, 5, 5 (all 3 V-shaped) (P) 15 (ppt), 5 (Q) | 2 (P) 3 (Q) | 11.7 (P) | >60 (P) |
| 4 | 30, >100 (3x) | 3, 4, 8 | 26.3, 30.7 | 67 |
| 5 | 70, >100 | 4.5 | 10 | 74 |
| 6 | 15, 21, 20, 40 | 4, 1, 3 | 21.5 | >60 |
| 7 | 18, 13, 12, 20 | 2 | 8.83 | 39 |
| 8 | 15, 15, 18, 15 | 3, >100 | 7.17 | |
| 9 | 20 (ppt), 30, 52, 40 (P) | 1, 2 (P) | 20.1, 28.2 (P) 38.6 (R) | 75 (P) |
| 10 | 70, 50 | 4 | 75.7 | 67 |
| 11 | 18 (ppt) 20 (ppt), 20 (2x), >100 (P) >100, 21, 30 (Q) | 1, 1, 3 (P) 1, 0.8 (Q) | 5.62 (P) 6.78 (Q) | 23 (P) 9 (Q) |
| 12 | 20 (4x) | 1, 1 | 3.93 | >60 |
| 13 | 21, >100, 20 (ppt), 15 (ppt), >100 | 0.9 | 6.41 | 6 |
| 14 | 18 (ppt), 8, 6 (ppt), 7 (ppt) | 1.0 | 10.9 | >10 (V-shaped) |
| 15 | 100 (3x) P 100, 16 (V-shaped) 12, 15, 11 (Q) | 1 (P) 1.2 (Q) | 8.52 (P) 7.26 (Q) 7.07 (Q) | >60 (P) 7 (Q) |
| 16 | 18, 7.5, 10 (P) 70, 32, 42 (Q) | 3, 0, 3 (P) 1.1, 0.8, 0.6 (Q) | 12 (P) 10.3 (Q) | 13 (P) |
| 17 | >100 (ppt) (3x) | 6.2 | 64.5 | >60 (Q), 41 (R) |
| 18 | >100 (5x) (P) | 30, >100 (P) | >100 (P) | 9, >40, 53 (P), 12 |
| 19 | 3, 4, >100, 2.2 | >100, 1, 1, 1.5 | 31.0, 34.0 | >60, 43 |
| 20 | 4.2 | 6 | 68.6 | 22 |
| 21 | 3 | 4 | 62.7 | 26 |
| 22 | 3 | 9 | >100 | 24 |
| 23 | 20 | 2 | >100 | 17 |
| 24 | >100 | 20 | >100 | 91 |
| 25 | >100 | 4 | 21.1 | 47 |
| 26 | >100 | 1 | >100 | 57 |
| 27 | >100 | 3 | 19.8 | 74 |
| 28 | >100 | 5 | 42.3 | 27 |
| 29 | >100 | 4 | 38.1 | 30 |
| 30 | 30, 20 | 4, 2 | 75.3 | 38 |
| 31 | >100 | 1 | 22.6 | 86 |
| 32 | >100 | 1 | 29.2 | 96 |
| 33 | >100 | >100 | >100 | >10 |
| 34 | 45 | 3 | 45.0 | 48 |
| 35 | >100 | 100 | >100 | 154 |
| 36 | >100 | >100 | >100 | 149 |
| 37 | >100 | 0.8 | 30.2 | 25 |
| 38 | 20, 10 (V) | 3 | 23.4 | 184 |
| 39 | >100 | 20 | >100 | 21 |
| 40 | >100 | 3.0 | >100 | 53 |
| 41 | >100 | 5 | 49.7 | 42 |
| 42 | >100 | 2 | 55.6 | 30 |
| 43 | >100 | 0.3 | 24.2 | 63 |
| 44 | >100 | 1 | 26.5 | 52 |
| 45 | >100 | 1 | 21.5 | 32 |
| 46 | >100 | 6 | 34.3 | |
| 47 | >100 | 2 | 38.2 | |
| 48 | 25 | 10 | >100 | |
| 49 | >100 | >100 | >100 | |
| 50 | >100 | >100 | >100 | |
| 51 | 85 | 0.8 | 39.1 | |
| 52 | 75 | 0.5 | 36.5 | |
| 53 | >100 | 0.3 | 30.0 | |
| 54 | >100 | 0.4 | 43.9 | |
| 55 | 12 | 2 | 5.1 | 101 |
| 56 | >100 | 3 | 11.5 | 30 |
| 57 | 4.8 | 1.5 | 4.0 | 50 |
| 58 | 3.5 | 1 | 5.1 | 60 |
| 59 | >100 | >100 | >100 | 3 |
| 60 | >100 | 3 | 40.7 | 8 |
| 61 | 18, 7.5, 10 | 3, 0.3 | 12 | 13 |
| 62 | >100 | 1.5 | 8.98 | |
| 63 | 15, 15, 18 (ppt) | 1 | 9.43 | 45 |
| 64 | >100 | 5 | 35 | >100 |
| 65 | 60, 80 | 1.5 | 15.9 | >100 (V-shaped) |
| 66 | >100 (ppt), >100 (ppt) | 2.1 | 50.1 | >100 |
| 67 | 41 | 4 | 13.3 | >60 |
| 68 | >100, >100 | 1 | >100 | 110 |
| 69 | 2 (V-shaped), 3.5 (ppt) | 0.8 | 11.7 | 58 |
| 70 | 20, 100 | 10 | >100 | 65 |
| 71 | >100 | 3 | | >60 |
| 72 | 40, 15, 12 | 2, 2.5 | 74.8 | >60, >60 |
| 73 | 25, 35, 40 | 0.3 | 9.43 | >60 |
| 74 | 6, 18, 19, 18 | 0.3, 0.5 | 8.36 | >60 |
| 75 | >100 | 2.2 | 46.2 | >60 |
| 76 | 3 | 0.5 | 8.59 | >60 |
| 77 | 18, 15 | 8, 0.3 | 9.49 | >60 |
| 78 | 70 | 0.1 | >100 | 8 |
| 79 | 3.1, 50, 38, 70, 70, 30, 40 | 1, 0.3, 0.3, 0.3 | 9.14 | 51 |
| 80 | >100 | 4 | 24.8 | >60 |
| 81 | >100 | 15 | 48.4 | 73 |
| 82 | >100, >100, >100 | 2, 0.3, 0.3 | | |
| 83 | >100 | >100 | | 9, 47, 29 |
| 84 | >100 | >100 | | 5, 40, 21 |
| 85 | >100 | 18 | | 8, 77, 45 |
| 86 | 40 | 18 | | >10, 89, 37 |
| 87 | >100 | 50 | | >10, 15, 32 |
| 88 | >100 | 10 | | >10, 37, 27 |
| 116 | >100, >100 | 18, 30 | | 96 |
| 117 | >100 | 3 | 61.3 | >100 |
| 118 | >100, >100 | 6 | | >60 |
| 119 | >100 | 3 | | >60 |
| 120 | >100 | 3 | | >60 |
| 121 | >100, >100 | 1 | | |
| 122 | >100 | 2 | >100 | >60 |
| 123 | >100 (3x), 14 4, 18, >100, >100 (Q) | 3, 3 3.2, 4 (Q) | 70.8 85.2 (Q) | >60 (Q) |
| 124 | >100 | 10 | 62.7 | |
| 125 | 82 | 10 | >100 | 80 |
| 126 | >100, >100 30, 100 (Q) | 4, 5 10, 4 (Q) | 84 73.9 (Q) | 63 >60 (Q) |
| 127 | >100 (ppt) | 10 | >100 | 67 |
| 128 | >100 (ppt) (4x) 11, >100 (3x) 15, 20, 10, 7.5 (Q) 15, >100 (3x) Q | 10, 41, 6 7, 3, 3 (Q) | 75 >60 (Q) | 60 >60 (Q) |
| 129 | 1 (V-shaped) (2x) >100 (ppt) | 10, 3, 2, 2 | >100 | >102 |
| 130 | >100 (3x) | 2, >100, 50 | 47.5 | 238 |
| 131 | >100 | 10 | 93.5 | >60 |
| 132 | >100 | 10 | >100 | 60 |
| 133 | >100 | >100 | >100 | >60 |
| 134 | >100 | 2 | 36.5 | >60 |
| 135 | >100 | 1.2 | 31.2 | >60 |
| 136 | >100 | 3 | >100 | 53 |

TABLE 1-continued

β-Amyloid Inhibitory Activity of Compounds of Formula I

| Example No. | BASSR ($IC_{50} = \mu M$) | BASST ($IC_{50} = \mu M$) | BATYM ($IC_{50} = \mu M$) | BAPA ($IC_{50} = \mu M$) |
|---|---|---|---|---|
| 137 | >100, >100 | 3 | | 52 |
| 141 | >100 | 7 | 56.7 | >50 |
| 142 | >100 | 2.1 | 26.9 | 55 |
| 143 | >100 (4x) | 40, 30 | >100 | 2, >60, >60 |
| 144 | 15, 25 | 40 | >100 | 114 |
| 145 | 10, 40, 30 | 4 | 56.8 | 9 |
| 146 | >100 | 30 | >100 | >60 |
| 147 | >100 | 10 | 93.4 | >60 |
| 148 | >100 | | >100 | |
| 149 | >100 | >100 | >100 | >60 |
| 150 | >100 | 10 | >100 | 76 |
| 151 | >100, >100 | 5, >100 | >100 | 108 |
| 154 | >100 | 3, 30 | 70.8 | |
| 155 | >100 | 3 | 44.6 | |
| 156 | | | 27.8 | |
| 157 | | | 25.9 | |

A letter in parentheses after particular value indicates the particular synthetic lot of the compound tested. The terms "P," "Q," "R," "S," "T," and "Z" designate different lots of the same compound. For example, 10 (P) indicates that compound tested was from Lot P. If no lot is specified, the lot of the compound was Lot P.

The abbreviation "ppt" means precipitate and indicates that a precipitate formed the indicated concentration. In addition, the term "V-shaped" means that inhibition was observed followed by precipitation.

A value followed by a number and x(i.e., 4x) means that the compound was tested four times, and each time the result was the same.

The invention compounds have also shown good activity in standard in vivo assays commonly used to evaluate agents to treat diseases related to aggregation of amyloid proteins, especially Alzheimer's disease and other amyloidoses. In one assay, amyloid protein is induced into the spleen of mice by subcutaneous injections of silver nitrate, Freund's complete adjuvant, and an intravenous injection of amyloid enhancing factor. Silver nitrate is administered each day through Day 11. Test compounds are administered to the mice daily starting on Day 1 through Day 11. On Day 12, the animals are sacrificed, and the spleens are removed, histologically prepared, stained with Congo red, and the percent area of the spleen occupied by birefringent, Congo red-stained amyloid is quantitated microscopically. Invention compounds evaluated in this test have inhibited splenic amyloid deposition by up to 70% relative to untreated controls.

Another in vivo assay in which the invention compounds have been evaluated uses transgenic mice. The mice bear a human β-amyloid precursor protein transgene with a prion promoter and are described by Hsiao et al., "Correlative memory deficits, Aβ elevation, and amyloid plaques in transgenic mice," Science 1966;274:99–102. These transgenic mice develop β-amyloid deposits at about 9 months of age. By 15 months, diffuse and compact senile plaques are abundant, primarily in the neocortex, olfactory bulb, and hippocampus. Invention compounds are administered orally to the mice beginning at the age of 8 months (Oust prior to the onset of amyloid deposits) and continuing for several months (up to about age 14–18 months). The animals are then sacrificed, and the brains are removed. The amount of amyloid in the brain is quantitated both histologically and biochemically. Invention compounds evaluated in this model have inhibited amyloid accumulation in the cortex and hippocampus by up to 49% relative to untreated controls.

The above data establishes that representative invention compounds are active in standard assays used to measure inhibition of protein aggregation. The compounds exhibit excellent specificity, for example, as shown in the BASST assay, as well as the BATYM and BAPA assays. The compounds are thus useful to clinically inhibit amyloid protein aggregation and to image amyloid deposits for diagnostic use. The compounds will be used in the form of pharmaceutical formulations, and the following examples illustrate typical compositions.

Example 164

Tablet Formulation

| Ingredient | Amount |
|---|---|
| Compound of Example 1 | 50 mg |
| Lactose | 80 mg |
| Cornstarch (for mix) | 10 mg |
| Cornstarch (for paste) | 8 mg |
| Magnesium Stearate (1%) | 2 mg |
| | 150 mg |

The compound of Example 1 is mixed with the lactose and cornstarch (for mix) and blended to uniformity to a powder. The cornstarch (for paste) is suspended in 6 mL of water and heated with stirring to form a paste. The paste is added to the mixed powder, and the mixture is granulated. The wet granules are passed through a No. 8 hard screen and dried at 50° C. The mixture is lubricated with 1% magnesium stearate and compressed into a tablet. The tablets are administered to a patient at the rate of 1 to 4 each day for prevention of amyloid protein aggregation and treatment of Alzheimer's disease.

Example 165

Parenteral Solution

In a solution of 700 mL of propylene glycol and 200 mL of water for injection is added 20.0 g of Compound No. 19 (Example 19). The mixture is stirred and the pH is adjusted to 5.5 with hydrochloric acid. The volume is adjusted to 1000 mL with water for injection The solution is sterilized, filled into 5.0 mL ampoules, each containing 2.0 mL (40 mg of Compound No. 19), and sealed under nitrogen. The solution is administered by injection to a patient suffering from medullary carcinoma of the thyroid and in need of treatment.

Example 166

Patch Formulation

Ten milligrams of 2-{4-[3-(3,4-dichlorophenyl)propyl] phenylamino}benzoic acid is mixed with 1 mL of propylene glycol and 2 mg of acrylic-based polymer adhesive containing a resinous cross-linking agent. The mixture is applied to an impermeable backing (30 $cm^2$) and applied to the upper back of a patient for sustained release treatment of amyloid polyneuropathy.

The invention and the manner and process of making and using it, are now described in such full, clear, concise, and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of inhibiting the aggregation of amyloid proteins to form amyloid deposits, the method comprising administering to a patient in need of inhibition of the aggregation of amyloid protein an amyloid protein aggregation inhibiting amount of a compound of Formula I

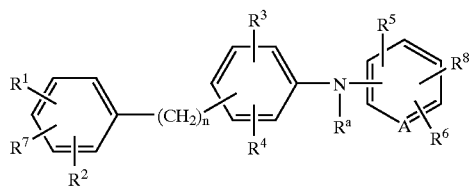

wherein

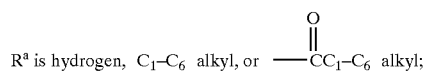

n is 0 to 5 inclusive;

$R^1$, $R^2$, $R^3$, $R^4$, $R^5$, $R^6$, and $R^7$ are independently hydrogen, halogen, —OH, —NH$_2$, NR$^b$R$^c$, —CO$_2$H, —CO$_2$C$_1$–C$_6$ alkyl, —NO$_2$, —OC$_1$–C$_{12}$ alkyl, —C$_1$–C$_8$ alkyl, —CF$_3$, —CN, —OCH$_2$ phenyl, —OCH$_2$-substituted phenyl, —(CH$_2$)$_m$-phenyl, —O-phenyl, —O-substituted phenyl,

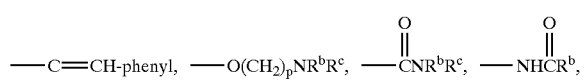

—NH(CH$_2$)$_p$NR$^b$R$^c$, —N(C$_1$–C$_6$alkyl)(CH$_2$)$_p$NR$^b$R$^c$,

$R^8$ is COOH, tetrazolyl, —SO$_2$R$^d$, or —CONHSO$_2$R$^d$;

$R^b$ and $R^c$ are independently hydrogen, —C$_1$–C$_6$ alkyl, —(CH$_2$)$_m$-phenyl, or R$^b$ and R$^c$ taken together with the nitrogen atom to which they are attached form a cyclic ring selected from piperidinyl, pyrrolyl, imidazolyl, piperazinyl, 4-C$_1$–C$_6$ alkylpiperazinyl, morpholino, thiomorpholino, decahydroisoquinoline, or pyrazolyl;

$R^d$ is hydrogen, —C$_1$–C$_6$ alkyl, —CF$_3$, or phenyl;

m is 0 to 5 inclusive;

p is 1 to 5 inclusive;

A is CH;

$R^1$ and $R^2$, when adjacent to one another, can be methylene-dioxy;

or the pharmaceutically acceptable salts thereof.

2. The method of claim 1 wherein
$R^a$ is hydrogen;
n is 2; and
$R^3$ and $R^4$ are hydrogen.

3. The method of claim 1 wherein
$R^a$ is hydrogen;
$R^3$ and $R^4$ are hydrogen; and
n is 2 to 5 inclusive.

4. The method of claim 1 wherein
$R^a$ is hydrogen;
n is 2;
$R^3$ and $R^4$ are hydrogen; and
$R^1$, $R^2$, and $R^7$ are independently chlorine, —N(CH$_2$CH$_3$)$_2$, —OH, CH$_3$—, fluorine, —CF$_3$, phenyl, hydrogen, —OCH$_2$ phenyl, —O(CH$_2$)$_3$N(CH$_3$)$_2$, —O phenyl, —O(CH$_2$)$_7$CH$_3$, —CH(CH$_2$OCH$_2$CH$_3$)$_2$, pyrrolyl, —CH=CH-phenyl,

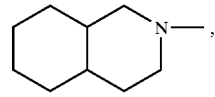

—N[(CH$_2$)$_3$CH$_3$]$_2$, substituted phenyl, —OCH$_2$-substituted
phenyl, pyrazolyl, or —N(phenyl)$_2$.

5. The method of claim 1 wherein
$R^a$ is hydrogen;
n is 3, 4, or 5;
$R^3$ and $R^4$ are hydrogen; and
$R^1$, $R^2$, and $R^7$ are independently chlorine or hydrogen.

6. The method of claim 1 wherein
$R^a$ is hydrogen;
n is 2;
$R^3$ and $R^4$ are hydrogen; and
$R^5$ and $R^6$ are independently hydrogen, —CO$_2$H, —NO$_2$, —OCH$_3$, imidazolyl, —CN, fluorine, —CH$_3$, —CF$_3$, halogen, —NH—C$_1$–C$_6$ alkyl, —N(C$_1$–C$_6$alkyl)$_2$, —NH$_2$, or pyrrolyl.

7. The method of claim 1 wherein
$R^a$ is hydrogen;
n is 2;
$R^3$ and $R^4$ are hydrogen; and
$R^8$ is —CO$_2$H.

8. A method of inhibiting the aggregation of amyloid proteins to form amyloid deposits, the method comprising administering to a patient in need of inhibition of the aggregation of amyloid protein an amyloid protein aggregation inhibiting amount of a compound of Formula I

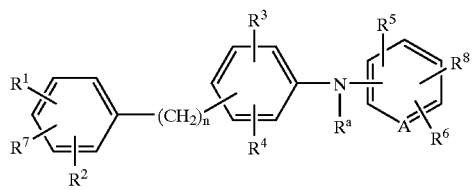

wherein
$R^a$ is hydrogen;
n is 1 to 5 inclusive;
$R^3$ and $R^4$ are hydrogen;

R¹, R⁷, and R² are independently chlorine, —N(CH₂CH₃)₂, —OH, CH₃—, fluorine, —CF₃, phenyl, hydrogen, —OCH₂ phenyl, —O(CH₂)₃N(CH₃)₂, —O phenyl, —O(CH₂)₇CH₃, —CH(CH₂OCH₂CH₃)₂, pyrrolyl, —CH=CH-phenyl, —N[(CH₂)₃CH₃]₂, substituted phenyl, —OCH₂-substituted phenyl, pyrazolyl, or —N(phenyl)₂;

R⁵ and R⁶ are independently hydrogen, —CO₂H, —NO₂, —OCH₃, imidazolyl, —CN, fluorine, —CH₃, —CF₃, or pyrrolyl;

R⁸ is COOH or tetrazolyl;

A is CH;

R¹ and R², when adjacent to one another, can be methylene-dioxy;

or the pharmaceutically acceptable salts thereof.

9. The method of claim 8 wherein the compound of Formula I is:

2-[[4-[2-(3,4-Dichlorophenyl)ethyl]phenyl]amino-benzoic acid;

2-{4-[2-(3,4-Dichloro-phenyl)-ethyl]phenylamino}-5-nitrobenzoic acid;

2-{4-[4-(3,4-Dichloro-phenyl)-ethyl]phenylamino}-4-methoxy-5-nitrobenzoic acid;

2-{4-[2-(3,4-Dihydroxy-phenyl)-ethyl]-phenylamino}benzoic acid;

2-{4-[2-(4-Dibutylamino-phenyl)-ethyl]phenylanino}benzoic acid;

2-{4-[2-(3,4,5-Trihydroxy-phenyl)-ethyl]phenylamino}benzoic acid;

2-{4-[3-(3,4-Dichlorophenyl)propyl]phenylamino}-4-methoxy-5-nitrobenzoic acid;

2-{4-[3-(3,4-Dichlorophenyl)propyl]phenylamino}-4-imidazo-1-yl-5-nitrobenzoic acid;

2-{4-[3-(3,4-Dichlorophenyl)-propyl]phenylamino}benzoic acid;

2-{4-[4-(3,4-Dichlorophenyl)butyl]phenylamino}benzoic acid;

2-{4-[4-(3,4-Dichloro-phenyl)-butyl]-phenylamino}-5-nitro-benzoic acid;

2-{4-[4-(3,4-Dichlorophenyl)-butyl]phenylamino}-3,5-dinitrobenzoic acid;

2-{4-[5-(3,4-Dichlorophenyl)pentyl]phenylamino}-5-nitrobenzoic acid;

2-{4-[5-(3,4-Dichloro-phenyl)pentyl]phenylamino}-4-methoxy-5-nitrobenzoic acid;

2-[4-(3,4-Dichloro-benzyl)-phenylamino]-benzoic acid;

2-{4-[2-(3,4-Dimethyl-phenyl)-ethyl]-phenylamino}-5-nitro-benzoic acid;

2-{4-[2-(3,4-Difluoro-phenyl)-ethyl]-phenylamino}-5-nitro-benzoic acid;

2-{4-[2-(4-Chloro-3-trifluoromethyl-phenyl)-ethyl]-phenylamino}-benzoic acid;

2-[4-(2-Biphenyl-4-yl-ethyl)phenylamino]-5-nitro-benzoic acid;

5-Nitro-2-(4-phenethyl-phenylamino)-benzoic acid;

2-(4-Phenethyl-phenylamino)-benzoic acid;

2-{4-[2-(3,4-Dichloro-phenyl)-ethyl]-phenylamino}-5-methoxy-benzoic acid;

2-{4-[2-(3,4-Dichloro-phenyl)-ethyl]-phenylamino}-terephthalic acid;

2-{4-[2-(3,4-Dichloro-phenyl)-ethyl]-phenylamino}-5-methyl-benzoic acid;

4-{4-[2-(3,4-Dichloro-phenyl)-ethyl]-phenylamino}-isophthalic acid;

2-{4-[2-3,4-Dichloro-phenyl)-ethyl]-phenylamino}-5-methanesulfonyl-benzoic acid;

2-{4-[2-(3,4-Dichloro-phenyl)-ethyl]-phenylamino}-5-imidazol-1-yl-benzoic acid;

2-{4-[2-(3,4-Dichloro-phenyl)-ethyl]-phenylamino}-6-nitro-benzoic acid;

2-{4-[2-(3,4-Dichloro-phenyl)-ethyl]-phenylamino}-4-nitro-benzoic acid;

2-{4-[2-(3,4-Dichloro-phenyl)-ethyl]-phenylamino}-3-nitro-benzoic acid;

5-Cyano-2-{4-[2-(3,4-dichloro-phenyl)-ethyl]-phenylamino}-benzoic acid;

2-{4-[2-(3,4-Dichloro-phenyl)-ethyl]-phenylamino}-4,6-difluoro-benzoic acid;

6-{4-[2-(3,4-Dichloro-phenyl)-ethyl]-phenylamino}-2,3-difluoro-benzoic acid;

2-{4-[2-(3,4-Dichloro-phenyl)-ethyl]-phenylamino}-6-fluoro-benzoic acid;

2-{4-[2-(3,4-Dichloro-phenyl)-ethyl]-phenylanino }-3-fluoro-benzoic acid;

2-{4-[2-(3,4-Dichloro-phenyl)-ethyl]-phenylamino}-3-methyl-benzoic acid;

2-{4-[2-(3,4-Dichloro-phenyl)-ethyl]-phenylamino}-4-fluoro-benzoic acid;

2-{4-[2-(3,4-Dichloro-phenyl)-ethyl]-phenylamino}-3,5-difluoro-benzoic acid;

2-{4-[2-(3,4-Dichloro-phenyl)-ethyl]-phenylamino}-3-trifluoromethyl-benzoic acid;

2-{4-[2-(3,4-Dichloro-phenyl)-ethyl]-phenylamino}-6-trifluoromethyl-benzoic acid;

2-{4-[2-(3,4-Dichloro-phenyl)-ethyl]-phenylamino}-5-trifluoromethyl-benzoic acid;

2-{4-[2-(3,4-Dichloro-phenyl)-ethyl]-phenylamino}-5-pyrrol-1-yl-benzoic acid;

2-{4-[2-(4-Benzyloxy-phenyl)-ethyl]-phenylamino)}-benzoic acid;

2-(4-{2-[4-(3-Dimethylamino-propoxy)-phenyl]-ethyl}-phenylamino)-benzoic acid;

2-{4-[2-(4-Diethylamino-phenyl)-ethyl]-phenylamino}-benzoic acid;

2-{4-[2-(4-Phenoxy-phenyl)-ethyl]-phenylamino}-benzoic acid;

2-{4-[2-(4-Octyloxy-phenyl)-ethyl]-phenylamino}-benzoic acid;

2-(4-{2-[4-(2-Ethoxy-1-ethoxymethyl-ethyl)-phenyl]-ethyl}-phenylamino)-benzoic acid;

2-{4-[2-(4-Pyrrol-1-yl-phenyl)-ethyl]-phenylamino}-benzoic acid;

2-{4-[2-(4-Styryl-phenyl)-ethyl]-phenylamino}-benzoic acid;

2-{4-[2-(4-Dibutylamino-phenyl)-ethyl]-phenylamino}-benzoic acid;

2-{4-[2-(4'-Ethyl-biphenyl-4-yl)-ethyl]-phenylamino}-benzoic acid;

2-{4-[2-(4-Octyl-phenyl)-ethyl]-phenylamino}-benzoic acid;

2-(4-{2-[3-(3,5-Dichloro-phenoxy)-phenyl]-ethyl}-phenylamino)-benzoic acid;

2-(4-{2-[4-(2-Chloro-6-fluoro-benzyloxy)-phenyl]-ethyl}-phenylamino)-benzoic acid;

2-{4-[2-(4-Pyrazol-1-yl-phenyl)-ethyl]-phenylamino}-benzoic acid;
2-{4-[2-(4-Diphenylamino-phenyl)-ethyl]-phenylamino}-benzoic acid;
2-(4-{2-[4-(3,4-Dichloro-benzyloxy)-phenyl]-ethyl}-phenylamino)-benzoic acid;
2-{4-[2-[(3,4-Dichlorophenyl)propyl]phenylamino}-5-nitrobenzoic acid;
2-{4-[2-(3,4-Dimethyl-phenyl)-ethyl]phenylamino}-5-nitrobenzoic acid;
2-[[4-[2-(4-Chloro-3-trifluoromethylphenyl)ethyl]phenyl]amino-benzoic acid; or
2-[4-(3,4-Dichlorophenyl)phenyl]aminobenzoic acid.

10. The compounds:
2-{4-[4-(3,4-Dichloro-phenyl)-ethyl]phenylamino}-4-methoxy-5-nitrobenzoic acid;
2-{4-[2-(3,4-Dihydroxy-phenyl)-ethyl]-phenylamino}benzoic acid;
2-{4-[2-(4-Dibutylamino-phenyl)-ethyl]phenylamino}benzoic acid;
2-{4-[2-(3,4,5-Trihydroxy-phenyl)-ethyl]phenylamino}benzoic acid;
2-{4-[3-(3,4-Dichlorophenyl)propyl]phenylamino}-4-methoxy-5-nitrobenzoic acid;
2-{4-[3-(3,4-Dichlorophenyl)propyl]phenylamino)}-imidazo-1-yl-5-nitrobenzoic acid; or
2-{4-[4-(3,4-Dichlorophenyl)butyl]phenylamino}benzoic acid.

11. The compounds:
2-{4-[4-(3,4-Dichloro-phenyl)-butyl]-phenylamino}-5-nitro-benzoic acid;
2-{4-[4-(3,4-Dichlorophenyl)-butyl]phenylamino}-3,5-dinitrobenzoic acid;
2-{4-[5-(3,4-Dichlorophenyl)pentyl]phenylamino}-5-nitrobenzoic acid;
2-{4-[5-(3,4-Dichloro-phenyl)pentyl]phenylamino}-methoxy-5-nitrobenzoic acid;
2-[4-(3,4-Dichloro-benzyl)-phenylamino]-benzoic acid;
2-{4-[2-(3,4-Dimethyl-phenyl)-ethyl]-phenylamino}-5-nitro-benzoic acid;
2-{4-[2-(3,4-Difluoro-phenyl)-ethyl]-phenylamino}-5-nitro-benzoic acid;
2-{4-[2-(4-Chloro-3-trifluoromethyl-phenyl)-ethyl]-phenylamino}-benzoic acid;
2-[4(2-Biphenylyl-ethyl)-phenylamino]-S-nitro-benzoic acid;
5-Nitro-2-(4-phenethyl-phenylamino)-benzoic acid.
2-{4-[2-(3,4-Dichloro-phenylethyl]-phenylamino}-5-amino-benzoic acid;
2-{4-[2-(3,4-Dichloro-phenyl)-ethyl]-phenylamino}-5-trifluoromethyl-benzoic acid; or
2-{4-[2-(3,4-Dichlorophenyl)]phenylamino}-5-nitrobenzoic acid.

12. The compounds:
2-(4-Phenethyl-phenylamino}benzoic acid;
2-{4-[2-(3,4-Dichloro-phenyl)-ethyl]-phenylamino}-5-methoxy-benzoic acid;
2-{4-[2-(3,4-Dichloro-phenyl)-ethyl]-phenylamino}-terephthalic acid;
2-{4-[2-(3,4-Dichloro-phenyl)-ethyl]-phenylamino}-5-methyl-benzoic acid;
4-{4-[2-(3,4-Dichloro-phenyl)-ethyl]-phenylamino}-isophthalic acid;
2-{4-[2-(3,4-Dichloro-phenyl)-ethyl]-phenylamino}-5-methanesulfonyl-benzoic acid;
2-{4-[2-(3,4-Dichloro-phenyl)-ethyl]-phenylamino}-5-imidazol-1-yl-benzoic acid;
2-{4-[2-(3,4-Dichloro-phenyl)-ethyl]-phenylamino}-6-nitro-benzoic acid;
2-{4-[2-(3,4-Dichloro-phenyl)-ethyl]-phenylamino}-4-nitro-benzoic acid; or
2-{4-[2-(3,4-Dichloro-phenyl)-ethyl]-phenylamino}-3-nitro-benzoic acid.

13. The compounds:
5-Cyano-2-{4-[2-(3,4-dichloro-phenyl)-ethyl]-phenylamino}-benzoic acid;
2-{4-[2-(3,4-Dichloro-phenyl)-ethyl]-phenylamino}-4,6-difluoro-benzoic acid;
6-{4-[2-(3,4-Dichloro-phenyl)-ethyl]-phenylamino}-2,3-difluoro-benzoic acid;
2-{4-[2-(3,4-Dichloro-phenyl)-ethyl]-phenylamino}-6-fluoro-benzoic acid;
2-{4-[2-(3,4-Dichloro-phenyl)-ethyl]-phenylamino}-3-fluoro-benzoic acid;
2-{4-[2-(3,4-Dichloro-phenyl)-ethyl]-phenylamino}-3-methyl-benzoic acid;
2-{4-[2-(3,4-Dichloro-phenyl)-ethyl]-phenylamino}-4-fluoro-benzoic acid;
2-{4-[2-(3,4-Dichloro-phenyl)-ethyl]-phenylamino}-3,5-difluoro-benzoic acid;
2-{4-[2-(3,4-Dichloro-phenyl)-ethyl]-phenylamino}-3-trifluoromethyl-benzoic acid;
2-{4-[2-(3,4-Dichloro-phenyl)-ethyl]-phenylamino}-6-trifluoromethyl-benzoic acid;
2-{4-[3-(4-Diethylaminophenyl)propyl]phenylamino}benzoic acid;
2-{4-[3-(4-Nitrophenyl)propyl]phenylamino}benzoic acid;
2-{4-[3-(3-Nitrophenyl)propyl]phenylamino}benzoic acid;
2-{4-[3-(4-Aminophenyl)propyl]phenylamino}benzoic acid;
2-{1-[3-(3-Aminophenyl)propyl]phenylamino}benzoic acid;
2-{4-[2-(4-Aminophenyl)phenylamino}benzoic acid;
2-{4-[2-(4-Dipropylaminophenyl)ethyl]phenylamino}benzoic acid monohydrochloride;
2-{4-[2-(4-Diethylaminophenyl)ethyl]phenylamino}benzoic acid monohydrochloride monohydrate;
2-{4-[3-(3-Dipropylaminophenyl)propyl]phenylamino}benzoic acid;
2-{4-[3-(3-Dimethylaminophenyl)propyl]phenylanino}benzoic acid;
2-{4-[3-(4-Ethylaminophenyl)propyl]phenylamino}benzoic acid;
2-(N-{4-[3-(4-Diethylaminophenyl)propyl]phenyl}-N-ethylamino)benzoic acid;
2-{4-[2-(3-Dibenzylaminophenyl)ethyl]phenylamino}benzoic acid;
2-{4-[3-(3-Diethylaminophenyl)propyl]phenylamino}benzoic acid;
2-{4-[2-(3-Aminophenyl)ethyl]phenylamino}benzoic acid;

2-{4-[3-(4-Dimethylaminophenyl)propyl]phenylamino}benzoic acid;
2-{4-[2-(4-Acetylaminophenyl)ethyl]phenylamino}benzoic acid;
2-{4-[2-(3-Acetylaminophenyl)ethyl]phenylamino}benzoic acid;
2-{4-[2-(3-Dipropylaminophenyl)ethyl]phenylamino}benzoic acid monohydrochloride;
2-{4-[2-(3-Dibutylaminophenyl)ethyl]phenylanino}benzoic acid monohydrochloride;
2-{4-[3-(4-Acetylaminophenyl)propyl]phenylamino}benzoic acid;
2-{4-[3-(3-Acetylaminophenyl)propyl]phenylamino}benzoic acid;
2-{4-[2-(3-Diethylaminophenyl)ethyl]phenylamino}benzoic acid monohydrochloride;
2-{4-[2-(3-Piperidin-1-ylphenyl)ethyl]phenylamino}benzoic acid monohydrochloride;
2-{4-[3-(4-Dipropylaminophenyl)propyl]phenylamino}benzoic acid;
2-{4-[3-(4-Dibutylaminophenyl)propyl]phenylamino}benzoic acid;
2-{4-[3-(3-Dibutylaminophenyl)propyl]phenylamino}benzoic acid;
2-(4-{3-[4-(1H-Pyrrol-1-yl)phenyl]propyl}phenylamino}benzoic acid;
2-{4-[3-(4-Piperidin-1-ylphenyl)propyl]phenylamino}benzoic acid;
2-{4-[3-(4-Diethylcarbamoylphenyl)propyl]phenylamino}benzoic acid;
2-{4-[3-(4-Carboxyphenyl)propyl]phenylamino}benzoic acid;
2-{4-[3-(4-Diethylaminomethylphenyl)propyl]phenylamino}benzoic acid;
2-{4-[3-(4-Propylaminophenyl)propyl]phenylamino}benzoic acid;
2-{4-[3-(3-Propylaminophenyl)propyl]phenylamino}benzoic acid;
2-{4-[3-(4-Pyrrolidin-1-yl-phenyl)-propyl]-phenylamino}-benzoic acid;
2-{4-[3-(3-Piperidin-1yl-phenyl)-propyl]-phenylamino}-benzoic acid;
{5-[(1-Butyl-1,2,3,4-tetrahydro-6-quinolyl)methylidene]-4-oxo-2-thioxothiazolidin-3-yl}acetic acid;
{5-[(1-Butyl-2,3-dihydro-1H-indol-5-yl)methylidene]-4oxo-2-thioxothiazolidin-3-yl}acetic acid;
3-{5-[(1-Butyl-1,2,3,4-tetrahydroquinolin-6-yl)methylidene]-4-oxo-2-thioxo-thiazolidin-3-yl}propanoic acid;
4-{5-[(1-Butyl-1,2,3,4-tetrahydroquinolin-6-yl)methylidene]-4-oxo-2-thioxo-thiazolidin-3-yl}butanoic acid;
2-{4-[3-(3,4-Dichloro-phenyl)-propyl]phenylamino}-5-methyl-benzoic acid;
N-(2-{4-[3-(3,4-Dichloro-phenyl)-propyl]-phenylamino}-benzoyl)-methanesulfonamide;
2-{4-[2-(3,4-Dimethyl-phenyl)-ethyl]phenylamino}-5-nitro-benzoic acid;
2-[4-(2-Biphenyl-4-yl-ethyl)-phenylamino]-5-nitro-benzoic acid;
2-{4-[2-(4-Chloro-3-trifluoromethyl-phenyl)-ethyl]-phenylamino}-5-nitro-benzoic acid;
5-Amino-2-{4-[2-(3,4-Dichloro-phenyl)-ethyl]-phenylamino}-benzoic acid;
5-Nitro-2-(4-phenethyl-phenylamino)-benzoic acid;
2-{4-[2-(4-Fluoro-3-trifluoromethyl-phenyl)-ethyl]-phenylamino}-benzoic acid;
2-{4-[2-(3,4-Difluoro-phenyl)-ethyl]-phenylamino}-5-nitro-benzoic acid;
{4-[2-(3,4-Dichloro-phenyl)-ethyl]-phenyl}-[2-(1H-tetrazol-5-yl)-phenyl]-amine;
2-{4-[2-(4-Fluoro-3-trifluoromethyl-phenyl)-ethyl]-phenylamino}-5-nitro-benzoic acid;
2-(4-Phenethyl-phenylamino)-benzoic acid;
2-{4-[2-(3,4-Dichloro-phenyl)-ethyl]-phenylamino}-5-fluoro-benzoic acid;
2-{4-[2-(3-Chloro-phenyl)-ethyl]-phenylamino}-5-nitro-benzoic acid;
2-{4-[2-(4-Chloro-phenyl)-ethyl]-phenylamino}-5-nitro-benzoic acid;
2-{4-[2-(3,4-Dichloro-phenyl)-ethyl]-phenylamino}-5-methyl-benzoic acid;
2-{4-(2-Chloro-phenyl)-ethyl]-phenylamino}-5-nitro-benzoic acid;
2-{4-[2-(2,4-Dichloro-phenyl)-ethyl]-phenylamino}-5-nitro-benzoic acid;
2-{4-[2-(3,4-Dichloro-phenyl)-ethyl]-phenylamino}-6-trifluoromethyl-benzoic acid;
2-{4-[2-(4-Dibutylamino-phenyl)-ethyl]-phenylamino}-5-nitro-benzoic acid;
2-{4-[2-(3,4-Dichloro-phenyl)-ethyl]-phenylamino}-5dimethylamino-benzoic acid;
2-{4-[2-(3,5-Dichloro-phenyl)-ethyl]-phenylamino}-benzoic acid;
2-(4-{2-[(4aS,8aR)4-(Octahydro-isoquinolin-2-yl)-phenyl]-ethyl}-phenylamino)-benzoic acid;
2-(3',5'-Dichloro-3-methyl-biphenyl-4-ylamino)-benzoic acid;
2-(3',5'-Dibromo-3-methyl-biphenyl-4-ylamino)-benzoic acid;
2-(4-1,3-Benzodioxol-5-yl-2-methyl-phenylamino)-benzoic acid;
2-(2,2',4'-Trichloro-biphenyl-4-ylamino)-benzoic acid;
2-(2-Chloro-3',4'-difluoro-biphenyl-4-ylamino)-benzoic acid;
2-(3'-Bromo-2-chloro-biphenyl-4-ylamino)-benzoic acid;
2-{4-[2-(3,4-Dichloro-phenyl)-ethyl]-phenylamino}-5-nitro-benzoic acid;
3-{4-[2-(3,4-Dichloro-phenyl)-ethyl]-phenylamino}-benzoic acid;
5-{4-[2-(3,4-Dichloro-phenyl)-ethyl]-phenylamino}-isophthalic acid;
2-{4-[2-(3,4-Dichloro-phenyl)-ethyl]-phenylamino}-benzoic acid;
2-{4-[2-(3,4-Dichloro-phenyl)-ethyl]-phenylamino}-4,5-dimethoxy-benzoic acid;
2-{4-[2-(3-Chloro-4-methyl-phenyl)-ethyl]-phenylamino}-3-nitro-benzoic acid;
3-{4-[2-(3-Chloro-4-methyl-phenyl)-ethyl]-phenylamino}-benzoic acid;
5-{4-[2-(3-Chloro-4-methyl-phenyl)-ethyl]-phenylamino}-isophthalic acid;
2-{4-[2-(3-Chloro-4-methyl-phenyl)-ethyl]-phenylamino}-benzoic acid;

4-(4-{2-[(4aS,8aR)-4-(Octahydro-isoquinolin-2-ylphenyl]-ethyl}-phenylamino)-benzoic acid;
2-{4-[3-(4-Diethylamino-phenyl)propyl]-phenylamino}-5-methoxy-benzoic acid;
2-{4-[2-(3-Methoxy-phenyl)-ethyl]-phenylamino}-benzoic acid;
2-{4-[2-(3-Bromo-phenyl)-ethyl]-phenylamino}-benzoic acid;
2-{4-[2-(3-Fluoro-phenyl)-ethyl]-phenylamino}-benzoic acid;
2-{4-[2-(3,4-Dichloro-phenyl)-ethyl]-phenylamino}-5-methoxy-benzoic acid;
2-[2-(4-Fluoro-3-trifluoromethyl-phenyl)-2,3-dihydro-1H-isoindol-5-ylamino]-benzoic acid; or
2-{4-[2-(3-Fluoro4-methyl-phenyl)-ethyl]-phenylamino}-benzoic acid.

14. The compounds:
2-{4-[2-(3,4-Dichloro-phenyl)-ethyl]-phenylamino}-5-trifluoromethyl-benzoic acid;
2-{4-[2-(3,4-Dichloro-phenyl)-ethyl]-phenylamino}-5-pyrrol-1-yl-benzoic acid;
2-{4-[2-(4-Benzyloxy-phenyl)-ethyl]-phenylamino}-benzoic acid;
2-(4-{2-[4-(3-Dimethylamino-propoxy)-phenyl]-ethyl}-phenylamino)-benzoic acid;
2-{4-[2-(4-Diethylamino-phenyl)-ethyl]-phenylamino}-benzoic acid;
2-{4-[2-(4-Phenoxy-phenyl)-ethyl]-phenylamino}-benzoic acid;
2-{4-[2-(4-Octyloxy-phenyl)-ethyl]-phenylamino}-benzoic acid;
2-(4-{2-[4(2-Ethoxy-1-ethoxymethyl-ethyl)phenyl]-ethyl}-phenylamino)-benzoic acid;
2-{4-[2-(4-Pyrrol-1-yl-phenyl)-ethyl]-phenylamino}-benzoic acid; or
2-{4-[2-(4Styryl-phenyl)-ethyl]-phenylamino}-benzoic acid.

15. The compounds:
2-{4-[2-(4-Dibutylamino-phenyl)-ethyl]-phenylamino}-benzoic acid;
2-{4-[2-(4'-Ethyl-biphenyl-4-yl)-ethyl]-phenylamino}-benzoic acid;
2-{4-[2-(4-Octyl-phenyl)-ethyl]-phenylamino}-benzoic acid;
2-(4-{2-[3-(3,5-Dichloro-phenoxy)phenyl]-ethyl}-phenylamino)-benzoic acid;
2-(4-{2-[4-(2-Chloro-6-fluoro-benzyloxy)-phenyl]-ethyl}-phenylamino)-benzoic acid;
2-{4-[2-(4-Pyrazol-1-yl-phenyl)-ethyl]-phenylamino}-benzoic acid;
2-{4-[2-(4-Diphenylamino-phenyl)-ethyl]-phenylamino}-benzoic acid;
2-(4-{2-[4-(3,4-Dichloro-benzyloxy)-phenyl]-ethyl}-phenylamino)-benzoic acid;
2-{4-[2-(3,4-Dichloro-phenyl)-ethyl]-phenylamino}-5-amino-benzoic acid;
2-{4-[2-(3,4-Dichloro-phenyl)-ethyl]-phenylamino}-5-trifluoromethyl-benzoic acid;
2-{4-[2-(3,4-Dichlorophenyl)]phenylamino}-5-nitrobenzoic acid;
2-{4-[2-[(3,4-Dichlorophenyl)propyl]phenylamino}-5-nitrobenzoic acid;
2-{4-[2-(3,4-Dimethyl-phenyl)-ethyl]phenylamino}-5-nitrobenzoic acid;
2-[4-(3,4-Dichlorophenyl)phenyl]aminobenzoic acid.

16. 2-[4-[2-(3,4-Dichlorophenyl)ethyl]phenyl]aminobenzoic acid or a pharmaceutically acceptable salt thereof.

17. 2-{4-[3-(3,4-Dichlorophenyl)propyl]phenylamino}benzoic acid or a pharmaceutically acceptable salt thereof.

18. A compound which is selected from:
2-{4-[3-(4-Diethylamino-phenyl)-propyl]-phenylamino}-5-nitro-benzoic acid;
4-{4-[3-(4-Diethylamino-phenyl)-propyl]-phenylamino}-benzoic acid;
4-{4-[3-(4-Diethylamino-phenyl)-propyl]-phenylamino}-3-methoxy-benzoic acid;
2-{4-[2-(3-Chloro-4-methyl-phenyl)-ethyl]-phenylamino}-5-methoxy-benzoic acid;
{4-[2-(3-Chloro-4-methyl-phenyl)-ethyl]-phenyl}-(2-methoxy-5-nitro-phenyl)-amine;
2-{4-[3-(4-Diethylamino-phenyl)-propyl]-phenylamino}-3-nitro-benzoic acid;
3-{4-[3-(4-Diethylamino-phenyl)-propyl]-phenylamino}-benzoic acid;
2-{4-[2-(3,4-Dimethoxy-phenyl)-ethyl]-phenylamino}-benzoic acid;
2-{4-[2-(3,4-Dichloro-phenyl)-ethyl]-phenylamino}-benzoic acid monosodium;
2-{4-[2-(3,4-Dichloro-phenyl)-ethyl]-phenylamino}-benzoic acid monopotassium;
2-{[2-(3,4-Dichloro-phenyl)-ethyl]-phenylamino}-benzoic acid calcium salt (1:1);
2-{4-[2-(3,4-Dichloro-phenyl)-ethyl]-phenylamino}-benzoate-2-hydroxy-1,1-bis-hydroxymethyl-ethyl-ammonium;
2-{4-[4-(3,4-Dichloro-phenyl)-butyl]-phenylamino}-5-methoxy-benzoic acid;
2-{4-[2-(3,4-Difluoro-phenyl)-ethyl]-phenylamino}-benzoic acid;
2-{3-[2-(4-Chloro-phenyl)-ethyl]-phenylamino}-benzoic acid;
2-{3-[2-(3,4-Dimethyl-phenyl)-ethyl]-phenylamino}-benzoic acid;
2-{4-[2-(2,4-Dimethoxy-phenyl)-ethyl]-phenylamino}-benzoic acid;
2-{4-[2-(2-Chloro-phenyl)-ethyl]-phenylamino}-benzoic acid;
2-{4-[2-(2-Hydroxy-phenyl)-ethyl]-phenylamino}-benzoic acid;
2-{4-[2-(3-Chloro-phenyl)-ethyl]-phenylamino}-benzoic acid;
2-[4-(2-Biphenyl-4-yl-ethyl)-phenylamino]-benzoic acid;
2-{4-[2-(2,4-Dichloro-phenyl)-ethyl]-phenylamino}-benzoic acid;
3-{4-[2-(3,4-Dichloro-phenyl)-ethyl]-phenylamino}-benzoic acid;
4-{4-[2-(3,4-Dichloro-phenyl)-ethyl]-phenylamino}-benzoic acid;
2-{4-[2-(3,4,5-Trimethoxy-phenyl)-ethyl]-phenylamino}-benzoic acid;
2-{4-[2-(4-Phenoxy-phenyl)-ethyl]-phenylamino}-benzoic acid;
2-{4-[5-(3,4-Dichloro-phenyl)-pentyl]-phenylamino}-benzoic acid;

2-(3',5'-Dichloro-biphenyl-4-ylamino)-benzoic acid;
4-{4-[3-(3,4-Dichloro-phenyl)-propyl]-phenylamino}-2-methoxy-5-nitro-benzoic acid;
2-{4-[3-(3,4-Dichloro-phenyl)-propyl]-phenylamino}-5-fluoro-benzoic acid;
5-Amino-2-{4-[5-(3,4-dichloro-phenyl)-pentyl]-phenylamino}-benzoic acid;
N-(2-{4-[3-(3,4-Dichloro-phenyl)-propyl]-phenylamino}-benzoyl)-C,C,C-trifluoro-methanesulfonamide;
N-(2-{4-[3-(3,4-Dichloro-phenyl)-propyl]-phenylamino}-benzoyl)-benzenesulfonamide;
2-{4-[2-(3,4-Dichloro-phenyl)-ethyl]-phenylamino}-5-trifluoromethyl-benzoic acid;
4-{4-[2-(3,4-Dichloro-phenyl)-ethyl]-phenylamino}-isophthalic acid;
2-{4-[2-(3,4-Dichloro-phenyl)-ethyl]-phenylamino}-4-trifluoromethyl-benzoic acid;
2-{4-[2-(3,4-Dichloro-phenyl)-ethyl]-phenylamino}-3-trifluoromethyl-benzoic acid;
2-({4-[2-(3,4-Dichloro-phenyl)-ethyl]-phenyl}-methyl-amino)-5-dimethylamino-benzoic acid;
2-({4-[2-(3,4-Dichloro-phenyl)-ethyl]-phenyl}-methyl-amino)-benzoic acid;
2-{4-[2-(3,4-Dichloro-phenyl)-ethyl]-phenylamino}-5-dipropylamino-benzoic acid;
5-Dibutylamino-2-{4-[2-(3,4-dichloro-phenyl)-ethyl]-phenylamino}-benzoic acid;
2-{4-[2-(3,4-Dichloro-phenyl)-ethyl]-phenylamino}-5-diethylamino-benzoic acid;
2,2'-[1,2-Ethanediylbis(4,1-phenyleneimino)]bis-benzoic acid; and
4-[3-[4-(Diethylamino)phenyl]propyl]-N-(2-methoxy-5-nitrophenyl)-benzinamine.

19. The compounds:
2-[4-[2-(3,4-Dichlorophenyl)ethyl]phenyl]amino-benzoic acid;
2-{4-[2-(3,4-Dichloro-phenyl)-ethyl]phenylamino}-5-nitrobenzoic acid;
2-{4-[3-(3,4-Dichlorophenyl)-propyl]phenylamino}benzoic acid;
2-[4-[2-(4-Chloro-3-trifluoromethylphenyl)ethyl]phenyl]amino-benzoic acid; and
2-{[3-(4-Diethylaminophenyl)propyl]phenylamino}benzoic acid.

20. A pharmaceutical formulation comprising a compound of claim 10 admixed with a pharmaceutically acceptable diluent, excipient, or carrier therefor.

21. A pharmaceutical formulation comprising a compound of claim 11 admixed with a pharmaceutically acceptable diluent, excipient, or carrier therefor.

22. A pharmaceutical formulation comprising a compound of claim 12 admixed with a pharmaceutically acceptable diluent, excipient, or carrier therefor.

23. A pharmaceutical formulation comprising a compound of claim 13 admixed with a pharmaceutically acceptable diluent, excipient, or carrier therefor.

24. A pharmaceutical formulation comprising a compound of claim 14 admixed with a pharmaceutically acceptable diluent, excipient, or carrier therefor.

25. A pharmaceutical formulation comprising a compound of claim 15 admixed with a pharmaceutically acceptable diluent, excipient, or carrier therefor.

26. A pharmaceutical formulation comprising a compound of claim 16 admixed with a pharmaceutically acceptable diluent, excipient, or carrier therefor.

27. A pharmaceutical formulation comprising a compound of claim 17 admixed with a pharmaceutically acceptable diluent, excipient, or carrier therefor.

28. A pharmaceutical formulation comprising a compound of claim 19 admixed with a pharmaceutically acceptable diluent, excipient, or carrier therefor.

* * * * *